(12) United States Patent
Kanamori et al.

(10) Patent No.: US 9,293,491 B2
(45) Date of Patent: Mar. 22, 2016

(54) POLARIZATION IMAGE SENSOR AND ENDOSCOPE

(71) Applicant: Panasonic Corporation, Osaka (JP)

(72) Inventors: Katsuhiro Kanamori, Nara (JP); Brahm Pal Singh, Osaka (JP); Kunio Nobori, Osaka (JP); Hiroyoshi Komobuchi, Kyoto (JP); Mikiya Nakata, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 330 days.

(21) Appl. No.: 13/911,656

(22) Filed: Jun. 6, 2013

(65) Prior Publication Data

US 2013/0270421 A1 Oct. 17, 2013

Related U.S. Application Data

(63) Continuation of application No. PCT/JP2012/005018, filed on Aug. 7, 2012.

(30) Foreign Application Priority Data

Sep. 2, 2011 (JP) .................................. 2011-191703

(51) Int. Cl.
*H01L 27/00* (2006.01)
*H01L 27/146* (2006.01)
(Continued)

(52) U.S. Cl.
CPC ...... *H01L 27/14625* (2013.01); *A61B 1/00186* (2013.01); *G01J 3/0205* (2013.01);
(Continued)

(58) Field of Classification Search
CPC .................. H01L 27/14625; H01L 27/14621; H01L 27/14627; H01L 27/14629; G01J 3/0224; G01J 3/513; G01J 4/04; G01J 3/36; G01J 3/0205; G01J 3/0262; G01J 3/0297; G02B 5/3083; G02B 23/24; G02B 5/201; G02B 5/3025; H04N 9/45
USPC ................................ 250/208.1; 348/272–273
See application file for complete search history.

(56) References Cited

U.S. PATENT DOCUMENTS 5,007,719 A * 4/1991 Hasegawa ............ G02B 15/173
359/679
6,025,873 A * 2/2000 Nishioka et al. ................ 348/72
(Continued)

FOREIGN PATENT DOCUMENTS

JP 59-011085 A 1/1984
JP 09-130818 A 5/1997
(Continued)

OTHER PUBLICATIONS

Notice of Reasons for Rejection for corresponding Japanese Application No. 2013-531025 mailed on Jun. 3, 2014 and English translation.
(Continued)

*Primary Examiner* — Georgia Y Epps
*Assistant Examiner* — Kevin Wyatt
(74) *Attorney, Agent, or Firm* — Renner, Otto, Boisselle & Sklar, LLP

(57) ABSTRACT

A polarization image sensor includes: photodiodes arranged on an image capturing plane; a color mosaic filter in which color filters in multiple different colors are arranged to face the photodiodes; an optical low-pass filter which covers the color mosaic filter; and polarization optical elements located closer to a light source than the optical low-pass filter is. Each polarization optical element covers an associated one of the photodiodes and makes light which is polarized in a predetermined direction in a plane that is parallel to the image capturing plane incident onto the optical low-pass filter. The color filters are arranged so that light that has passed through polarization optical elements is transmitted through an associated one of the color filters in a single color. Each color filter covers multiple photodiodes.

11 Claims, 47 Drawing Sheets

(51) Int. Cl.
*G02B 23/24* (2006.01)
*A61B 1/00* (2006.01)
*H04N 9/04* (2006.01)
*G01J 3/36* (2006.01)
*G01J 3/02* (2006.01)
*G01J 3/51* (2006.01)
*G01J 4/04* (2006.01)
*G02B 5/20* (2006.01)
*G02B 5/30* (2006.01)
*H04N 5/225* (2006.01)
*G01J 3/12* (2006.01)

(52) U.S. Cl.
CPC ............ *G01J 3/0224* (2013.01); *G01J 3/0262* (2013.01); *G01J 3/0297* (2013.01); *G01J 3/36* (2013.01); *G01J 3/513* (2013.01); *G01J 4/04* (2013.01); *G02B 5/201* (2013.01); *G02B 5/3025* (2013.01); *G02B 5/3083* (2013.01); *G02B 23/24* (2013.01); *H01L 27/14621* (2013.01); *H01L 27/14627* (2013.01); *H01L 27/14629* (2013.01); *H04N 9/045* (2013.01); *G01J 2003/1213* (2013.01); *H04N 2005/2255* (2013.01)

(56) References Cited

U.S. PATENT DOCUMENTS

| | | | | |
|---|---|---|---|---|
| 6,049,367 A * | 4/2000 | Sharp et al. | ........ | G02B 5/3083 348/E5.133 |
| 2001/0005283 A1 * | 6/2001 | Osawa et al. | ................ | 359/497 |
| 2008/0267562 A1 * | 10/2008 | Wang et al. | ................... | 385/31 |
| 2009/0244339 A1 | 10/2009 | Murooka et al. | | |
| 2009/0244537 A1 | 10/2009 | Murooka et al. | | |
| 2009/0278954 A1 | 11/2009 | Kanamori et al. | | |
| 2009/0322970 A1 * | 12/2009 | Iwane | ................... | G02B 27/46 349/1 |
| 2010/0253820 A1 * | 10/2010 | Kanamori et al. | ................ | H01L 27/14621 348/280 |
| 2012/0075513 A1 * | 3/2012 | Chipman et al. | ............. | 348/302 |

FOREIGN PATENT DOCUMENTS

| | | |
|---|---|---|
| JP | 11-146406 A | 5/1999 |
| JP | 2005-286034 A | 10/2005 |
| JP | 2009-240676 A | 10/2009 |
| JP | 2009-246770 A | 10/2009 |
| JP | 2009-246840 A | 10/2009 |
| JP | 2011-097288 A | 5/2011 |
| JP | 2011-145343 A | 7/2011 |

OTHER PUBLICATIONS

International Search Report for corresponding International Application No. PCT/JP2012/005018 mailed Nov. 13, 2012.

Form PCT/ISA/237 for corresponding International Application No. PCT/JP2012/005018 dated Nov. 13, 2012 and partial English translation.

Imae et al., "Optimum Design of Wide-band Quarter Wave Plates (QWPs) Utilizing Form Birefringence", Konica Minolta Technology Report vol. 3 (2006), pp. 62-67 and English Abstract.

* cited by examiner

ELEMENT'S AZIMUTH ANGLE (°)

*FIG.43*
VIEWED IN DIRECTION 1604
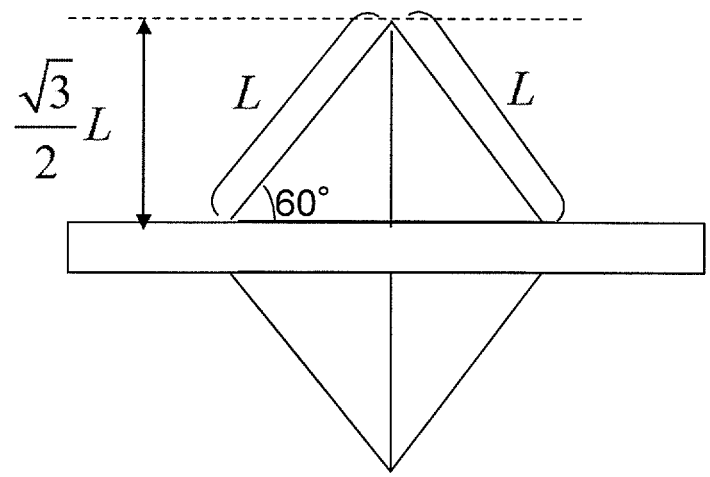
VIEWED IN DIRECTION 1605
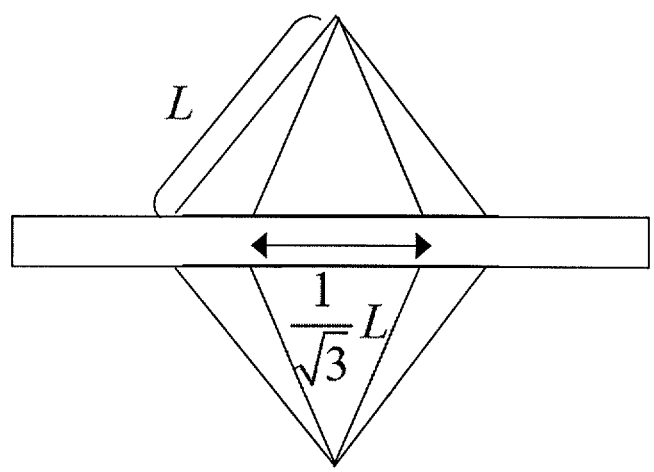

*FIG.52*
(A)
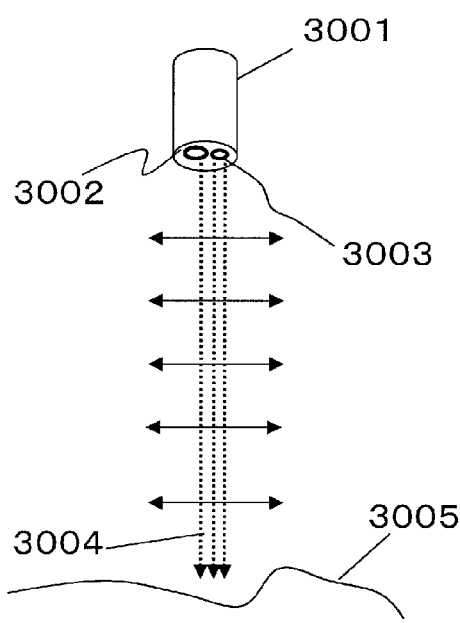
(B)
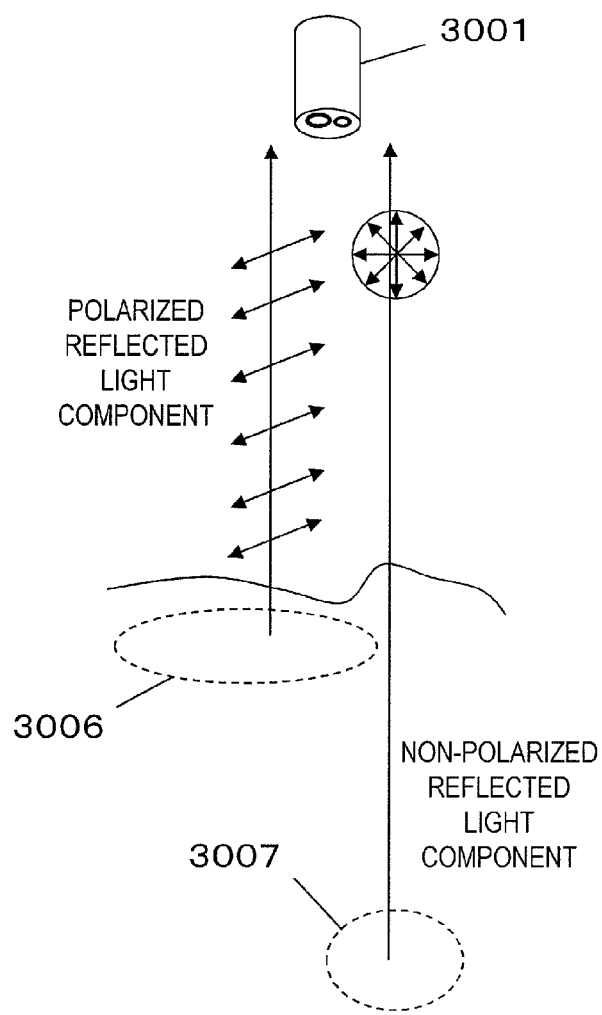

POLARIZATION IMAGE SENSOR AND ENDOSCOPE

This is a continuation of International Application No. PCT/JP2012/005018, with an international filing date of Aug. 7, 2012, which claims priority of Japanese Patent Application No. 2011-191703, filed on Sep. 2, 2011, the contents of which are hereby incorporated by reference.

BACKGROUND

1. Technical Field

The present disclosure relates to a polarization image sensor which can obtain the polarization information of light coming from an object.

2. Description of the Related Art

There are some technologies that use polarized light in an image sensing method for an endoscope.

For example, in order to get the surface topography of a viscera wall by polarization technologies, the endoscopes disclosed in Japanese Laid-Open Patent Publication No. 2009-240676, Japanese Laid-Open Patent Publication No. 2009-246770, and Japanese Laid-Open Patent Publication No. 2009-246840 irradiate the object with linearly or circularly polarized light and images the returning polarized light. An image sensor with a polarization mosaic structure is used as a polarization image sensor and is applied to only color filters representing one of the three primary colors of R, G and B (e.g., to only B pixels). The polarization mosaic structure is realized by arranging fine patterned polarizers so that their polarized light transmission axes face three or more different directions.

SUMMARY

In an ordinary single-panel color image sensor, to make a single light ray incident on multiple color mosaics, the light ray is split through an optical low-pass filter. The optical low-pass filter is typically made of a material with birefringence such as quartz. That is why such an optical low-pass filter is often called a "quartz low-pass filter". However, the optical low-pass filter may also be made of any birefringent material other than quartz. Even though a quartz LPF (low-pass filter) is supposed to be a representative birefringent low-pass filter according to the present disclosure, the low-pass filter may also be made of any natural material other than quartz or any artificial structure birefringent material as well. In any case, the optical low-pass filter has the function of decreasing the spatial resolution and is designed so that a single light ray is split into two light rays to be incident on two different photodiodes.

Such a quartz low-pass filter uses the birefringence phenomenon to split a light ray. That is why the polarization state of a light ray collapses by being transmitted through a quartz low-pass filter. Although there have been some technologies that use color mosaic filters and polarization filters in combination, nobody has ever used color mosaic filters, polarization filters AND a quartz low-pass filter in combination.

In one general aspect, a polarization image sensor disclosed herein comprises: a plurality of photodiodes which are arranged on an image capturing plane and each of which converts light into an electrical signal; a color mosaic filter in which color filters in multiple different colors are arranged so as to face the photodiodes; an optical low-pass filter which covers the color mosaic filter; and a plurality of polarization optical elements which are located closer to a light source than the optical low-pass filter is. Each of the polarization optical elements covers an associated one of the photodiodes and makes light which is polarized in a predetermined direction in a plane that is parallel to the image capturing plane incident onto the optical low-pass filter. The color mosaic filter has a structure in which a plurality of color filters in multiple different colors are arranged two-dimensionally. The color filters are arranged so that light that has passed through a plurality of polarization optical elements is transmitted through an associated one of the color filters in a single color. Each color filter covers a plurality of photodiodes.

In another aspect, a polarization image sensor disclosed herein comprises: a plurality of photodiodes which are arranged on an image capturing plane and each of which converts light into an electrical signal; a color mosaic filter in which color filters in multiple different colors are arranged so as to face the photodiodes; an optical low-pass filter which is located closer to a light source than the color mosaic filter is; and a plurality of polarization optical elements which are located closer to the light source than the optical low-pass filter is. Each of the polarization optical elements covers associated ones of the photodiodes and makes light which is polarized in predetermined direction in a plane that is parallel to the image capturing plane incident onto the optical low-pass filter. The color mosaic filter has a structure in which a plurality of color filters in multiple different colors are arranged two-dimensionally. The color filters are arranged so that light that has passed through each polarization optical element is transmitted through associated ones of the color filters in multiple different colors.

According to the present disclosure, a polarization image sensor which can obtain a color image and polarization image of improved quality is provided.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 43 illustrates the shape of a single prism optical element according to the second embodiment of the present disclosure as viewed from two different directions.

FIG. 52 illustrates the function of separating light scattered from the surface of an organ's mucosa from light scattered from the depth, wherein (A) illustrates the light emitting end and (B) illustrates the light receiving end.

DETAILED DESCRIPTION

Figure 1:
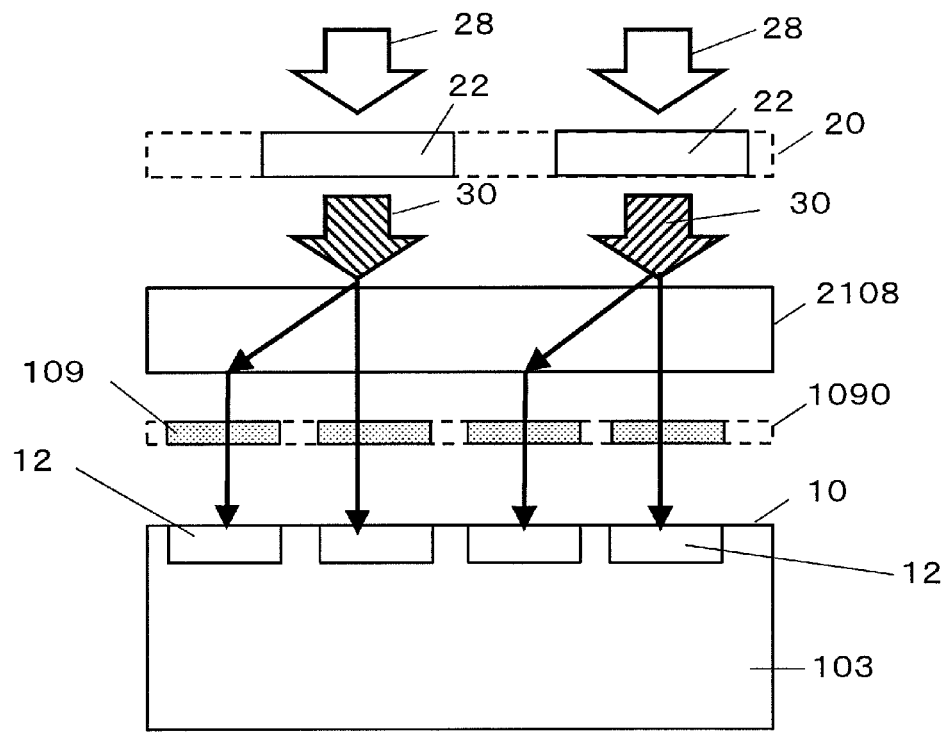
FIG. 1 shows a cross-sectional view illustrating a configuration for a polarization image sensor according to the present disclosure.

According to the embodiments to be described below, the problems described above are overcome by using a quartz low-pass filter and a polarization filter in an appropriate combination.

A polarization image sensor according to the present disclosure includes: a plurality of photodiodes which are arranged on an image capturing plane and each of which converts light into an electrical signal; a color mosaic filter in which color filters in multiple different colors are arranged so as to face the photodiodes; an optical low-pass filter which covers the color mosaic filter; and a plurality of polarization optical elements which are located closer to a light source than the optical low-pass filter is. Each of the polarization optical elements covers an associated one of the photodiodes and makes light which is polarized in a predetermined direction in a plane that is parallel to the image capturing plane incident onto the optical low-pass filter. The color mosaic filter has a structure in which a plurality of color filters in multiple different colors are arranged two-dimensionally. The color filters are arranged so that light that has passed through a plurality of polarization optical elements is transmitted through an associated one of the color filters in a single color. Each color filter covers a plurality of photodiodes.

In one embodiment, the optical low-pass filter is configured to shift at least a part of a light ray that has been transmitted through each of the polarization optical elements parallel to the image capturing plane by at least the arrangement pitch of the color filters in the color mosaic filter.

In one embodiment, one period of the two-dimensional arrangements of the polarization optical elements and the photodiodes has a spatial frequency which is an integral number of times as high as the cutoff frequency of the optical low-pass filter.

In one embodiment, the optical low-pass filter has a uniform optical property in a plane that is parallel to the image capturing plane.

In one embodiment, the optical low-pass filter includes: a first quarter wave plate; a first birefringent low-pass filter layer; a second quarter wave plate; and a second birefringent low-pass filter layer, which are stacked in this order so that the first quarter wave plate is closer to the light source than any other member of the optical low-pass filter.

In one embodiment, the optical low-pass filter further includes, between the second birefringent low-pass filter layer and the color mosaic filter, a third quarter wave plate, and a third birefringent low-pass filter layer, which are stacked in this order.

In one embodiment, the polarization optical elements form an array of polarizers in which a plurality of basic units, each being comprised of four polarization optical elements, are arranged in columns and rows. The four polarization optical elements included in each basic unit have mutually different polarized light transmission axis directions. And the basic units are arranged so that a color filter in a single color in the color mosaic filter is covered with a single basic unit.

In one embodiment, four of the basic units which are arranged in two columns and two rows cover four of the color filters which are arranged in two columns and two rows in the color mosaic filter.

In one embodiment, the four color filters that are arranged in two columns and two rows in the color mosaic filter form a Bayer arrangement.

In one embodiment, the optical low-pass filter further includes, between the third birefringent low-pass filter layer and the color mosaic filter, a fourth quarter wave plate, and a fourth birefringent low-pass filter layer, which are stacked in this order.

Another polarization image sensor according to the present disclosure includes: a plurality of photodiodes which are arranged on an image capturing plane and each of which converts light into an electrical signal; a color mosaic filter in which color filters in multiple different colors are arranged so as to face the photodiodes; an optical low-pass filter which is located closer to a light source than the color mosaic filter is; and a plurality of polarization optical elements which are located closer to the light source than the optical low-pass filter is. Each of the polarization optical elements covers associated ones of the photodiodes and makes light which is polarized in a predetermined direction in a plane that is parallel to the image capturing plane incident onto the optical low-pass filter. The color mosaic filter has a structure in which a plurality of color filters in multiple different colors are arranged two-dimensionally. The color filters are arranged so that light that has passed through each polarization optical element is transmitted through associated ones of the color filters in multiple different colors.

In one embodiment, the optical low-pass filter includes: a first quarter wave plate; a first birefringent low-pass filter; a second quarter wave plate; and a second birefringent low-pass filter, which are stacked in this order so that the first quarter wave plate is closer to the light source than any other member of the optical low-pass filter. The first quarter wave plate has a pattern in which the directions of slow and fast axes are adjusted so as to change the polarization state of light that has been transmitted through each of the polarization optical elements into the polarization state of circularly polarized light.

In one embodiment, the color mosaic filter has a structure in which basic units with a Bayer arrangement are arranged two-dimensionally so that one photodiode is associated with one color filter. The polarization optical elements have a first striped array in which two kinds of polarization optical elements, of which the polarized light transmission axes are different from each other by 90 degrees, are alternately arranged in one direction, and a second striped array in which two kinds of polarization optical elements, of which the polarized light transmission axes are different from each other by 90 degrees, are alternately arranged in one direction. The polarized light transmission axes of the polarization optical elements in the second striped array intersect at an angle of 45 degrees with the polarized light transmission axes of the polarization optical elements in the first striped array.

In one embodiment, the first quarter wave plate has a first set of striped portions which faces the first striped array of the polarization optical elements, and a second set of striped portions which faces the second striped array of the polarization optical elements. The slow and fast axes of the first and second sets of striped portions intersect with each other at an angle of 45 degrees.

(Embodiment 1)

FIG. 1 illustrates an exemplary cross-sectional structure for a polarization image sensor as a first embodiment of the present disclosure.

The polarization image sensor of this embodiment includes a plurality of photodiodes 12 which are arranged on an image capturing plane 10 and each of which converts light into an electrical signal and an optical element array 20 which covers these photodiodes 12. In FIG. 1, only four of those photodiodes 12 are illustrated. Actually, however, a much larger number of photodiodes 12 are arranged two-dimensionally on the image capturing plane 10.

The optical element array 20 includes a plurality of optical elements 22 which are arranged two-dimensionally in a plane that faces the image capturing plane 10. In FIG. 1, only two of the optical elements 22 included in the optical element array 22 are illustrated. Actually, however, a much larger number of optical elements 22 are included in the optical element array 20. A light ray 28 is incident on each optical element 22, of which a light ray 30 goes out. Thanks to the function of the optical element 22, the degree of polarization of the light ray 30 becomes higher than that of the light ray 28. The light ray 30 that has been transmitted through the optical element 22 then passes through a quartz low-pass filter 2108 to be split into two light rays. Those two split light rays are transmitted through color filters in multiple different colors in a mosaic color filter 1090 and then incident on photodiodes 12, which are arranged on a sensor substrate 103.

Figure 2:
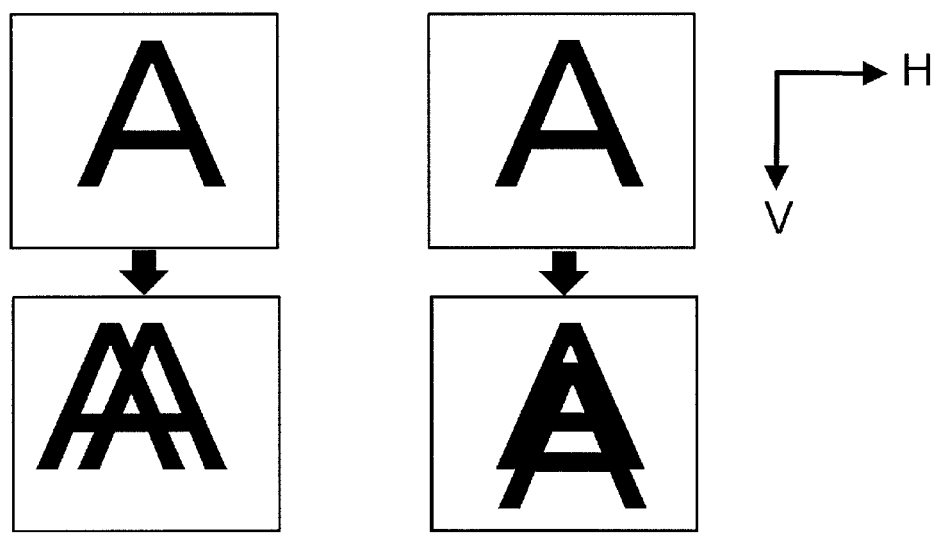
FIG. 2 illustrates how an image is shifted horizontally by a quartz low-pass filter.

The light ray is split by the quartz low-pass filter 2108. As a result, if an image representing a letter A is looked at through the quartz low-pass filter 2108, then the resultant image will look to the viewer's eyes as if two letters A were superposed one upon the other as schematically shown in FIG. 2. In FIG. 2, shown are two arrows respectively indicating a horizontal direction (H direction) and a vertical direction (V direction) in a plane which is parallel to the image capturing plane. In the following description, the horizontal direction (i.e., a direction parallel to scan lines) and vertical direction (i.e., a direction perpendicular to the scan lines) on the plane that is parallel to the image capturing plane will be sometimes referred to herein as just "H" and "V", respectively, for the sake of simplicity. These "H" and "V" directions are determined with respect to the image capturing plane, irrespective of the orientation of the image capture device.

In the example illustrated on the left-hand side of FIG. 2, the image has shifted horizontally. On the other hand, in the example illustrated on the right-hand side of FIG. 2, the image has shifted vertically. The magnitude of shift of an image depends on the thickness and refractive index anisotropy of the quartz low-pass filter. Even though the light ray is supposed to be split using a quartz low-pass filter in this embodiment of the present disclosure, a low-pass filter made of any birefringent material other than quartz may also be used.

In the exemplary arrangement shown in FIG. 1, the quartz low-pass filter is set up so as to produce a shift that is as long as the distance between the respective centers of two adjacent photodiodes. The distance between the respective centers of photodiodes will be sometimes referred to herein as a "pixel pitch". Also, in this description, each photodiode will be sometimes referred to herein as a "subpixel", instead of a "pixel". If the quartz low-pass filter is rotated 90 degrees within the plane, then the image shifting direction will also rotate 90 degrees. Thus, if two quartz low-pass filters are stacked one upon the other so that their shift directions intersect with each other at right angles, then the image will be split into four. And if an image is shifted by a distance that is an integral number of times as long as the arrangement pitch of color filters, then it is possible to prevent the color mosaic filter from producing moiré.

The optical elements 22 shown in FIG. 1 are polarization optical elements. In recent years, microscopic polarizers that have no wavelength dependence in the visible radiation range have been developed. Examples of such polarization optical elements include polarizers made of a polymer, polarizers made of a photonic crystal, form-birefringent micro retarders made of a dielectric and metallic wire grids made of aluminum. If such polarization optical elements are used, a color polarization image can be captured.

Hereinafter, embodiments of a polarization image sensor which obtains color information using white light will be described. As it is easy to obtain a color polarization image sensor of a frame sequential type by modifying those embodiments, a detailed description thereof will be omitted herein.

Figure 3:
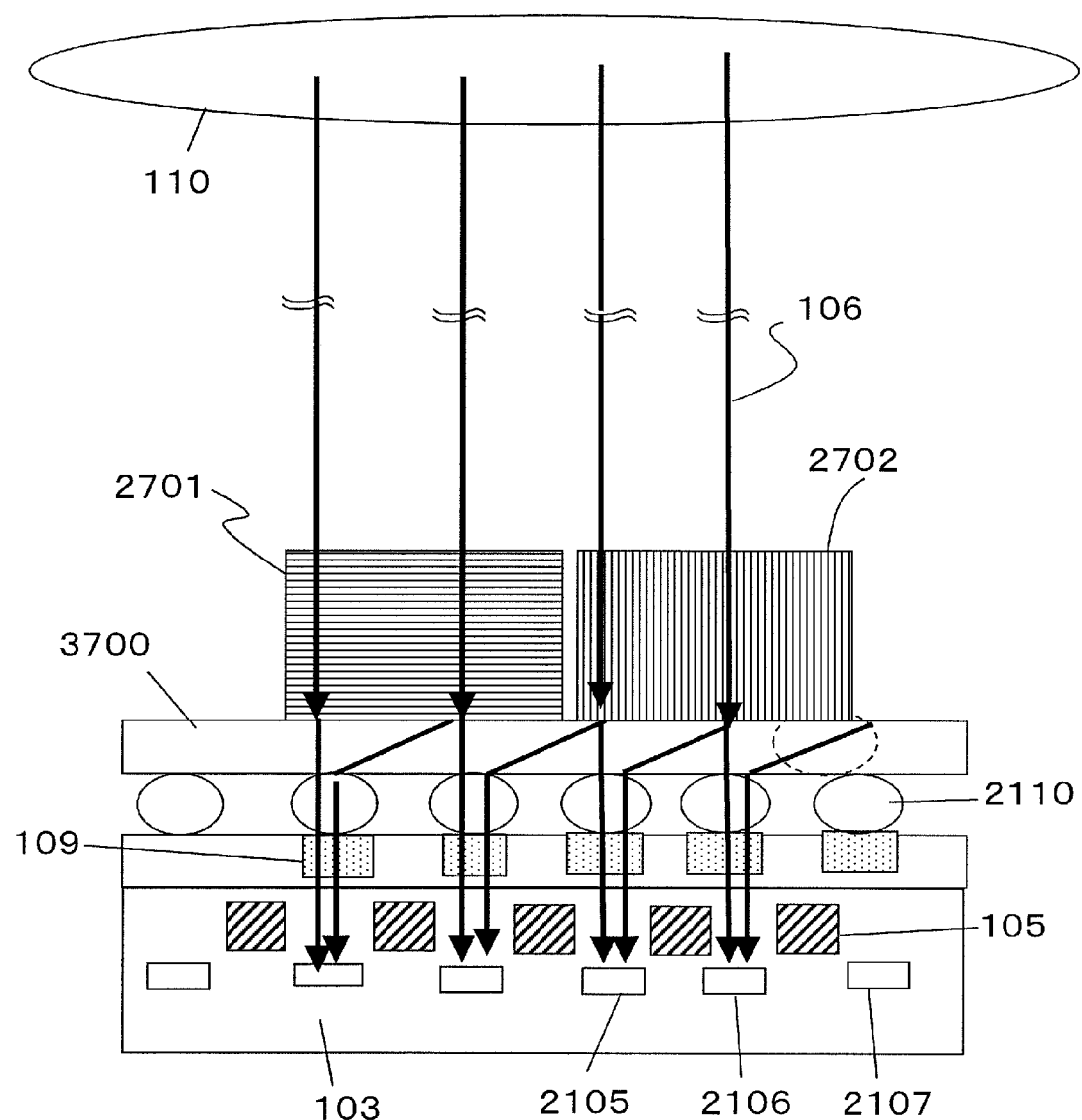
FIG. 3 shows a cross-sectional view illustrating a first embodiment of the present disclosure.

Next, look at FIG. 3, which illustrates a more specific cross-sectional structure for the polarization image sensor of this embodiment. In the exemplary configuration shown in FIG. 3, light that has come from an object (not shown) is transmitted through an objective lens 110, polarization optical elements 2701, 2702, a quartz LPF (low-pass filter) 3700, micro lenses 2110, and a color mosaic filter 109 and then incident on photodiodes 2105 to 2107. The polarization optical elements 2701 and 2702 correspond to the optical elements 22 shown in FIG. 1.

By adopting such a configuration, not only a polarization image but also a color image through the color mosaic can be captured with the influence of the birefringence of the quartz LPF 3700 on the polarization eliminated. The quartz LPF 3700 is used to eliminate moiré and false colors by making split light rays incident on the color mosaic filter 109. In this embodiment, the arrangement of respective color filters in the color mosaic filter and the multilayer structure of the quartz LPF are improved.

Figure 4:
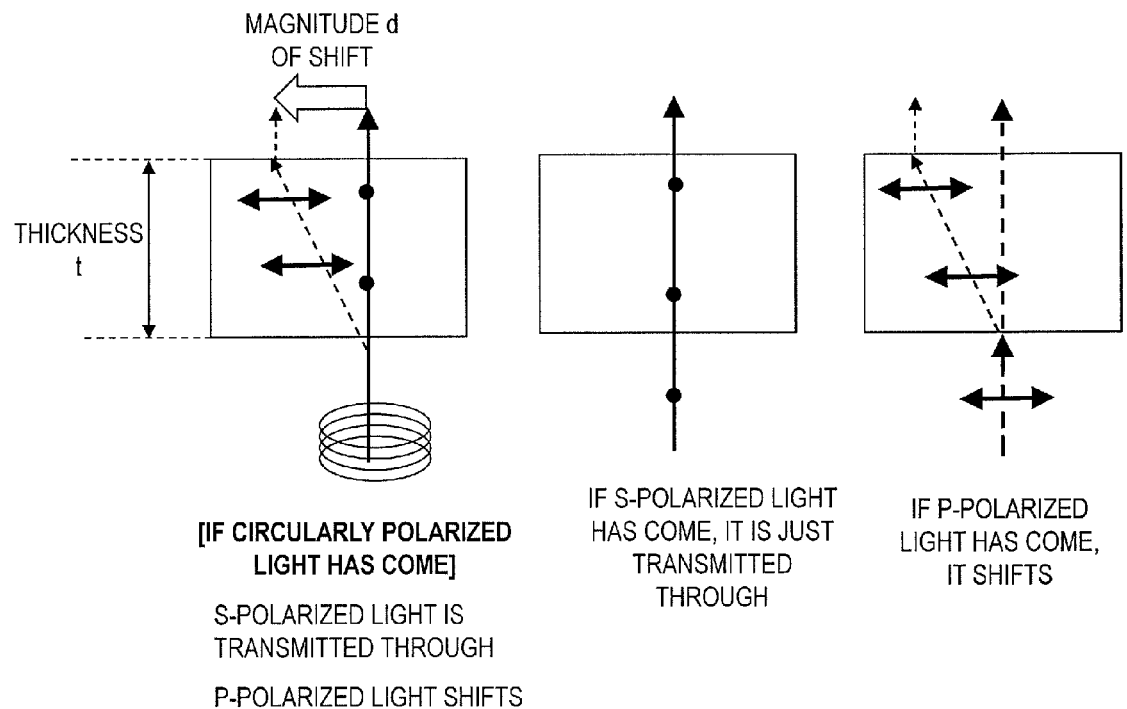
FIG. 4 illustrates the operating principle of a quartz LPF.

FIG. 4 illustrates the principle on which the quartz LPF operates. In FIG. 4, illustrated is a cross section of the quartz LPF. Specifically, on the left-hand side of FIG. 4, illustrated is how a circularly polarized light ray that has come from under the quartz LPF is incident on the quartz LPF. At the center of FIG. 4, illustrated is how a linearly polarized (S-polarized) light ray that has come from under the quartz LPF is incident on the quartz LPF. And on the right-hand side of FIG. 4, illustrated is how a linearly polarized (P-polarized) light ray that has come from under the quartz LPF is incident on the quartz LPF. In the example illustrated in FIG. 4, the polarization direction of the S-polarized light ray is the direction coming out of the paper, while the polarization direction of the P-polarized light ray is parallel to the paper. Also, in FIG. 4, the optic axes of crystals of the quartz LPF are present on the paper.

If a circularly polarized light ray or a non-polarized (i.e., random) light ray is incident on a quartz LPF, the incident light ray is split into an ordinary ray (which is an S-polarized light ray in this example) and an extraordinary ray (which is a P-polarized light ray in this example), which will follow mutually different optical paths. As a result, one of these two light rays passes through the output plane of the quartz LPF at a position that has shifted from the other one. Thus, as the shifted images will be superposed one upon the other when viewed through the quartz LPF, the spatial frequencies of the images will have a low range. As a result, the moiré, false colors and other artifacts by the color mosaic filter can be reduced.

The direction of the light ray shift caused by the quartz LPF is determined by the direction of the optic axis of single-axis crystals of the quartz LPF. The magnitude of that shift is determined by the thickness t and ordinary and extraordinary ray refractive indices of the quartz LPF.

If polarization optical elements are arranged closer to the light source than a quartz LPF is as is done in this embodiment, the light entering the quartz LPF is polarized light. That is why if the polarization optical elements are just arranged before the quartz LPF, some polarized light ray, which cannot be split by the quartz LPF, may be incident on the quartz LPF. In that case, the quartz LPF cannot achieve the effect of reducing the spatial frequency of the image. Specifically, if a linearly polarized light ray is incident on the quartz LPF and if the light ray is an S-polarized light ray, then the light ray will be just transmitted through the quartz LPF. On the other hand, if the incident light is a P-polarized light ray, then the light ray will be just obliquely transmitted and shifted. In those cases, the spatial frequency of the image cannot be reduced.

Figure 5:
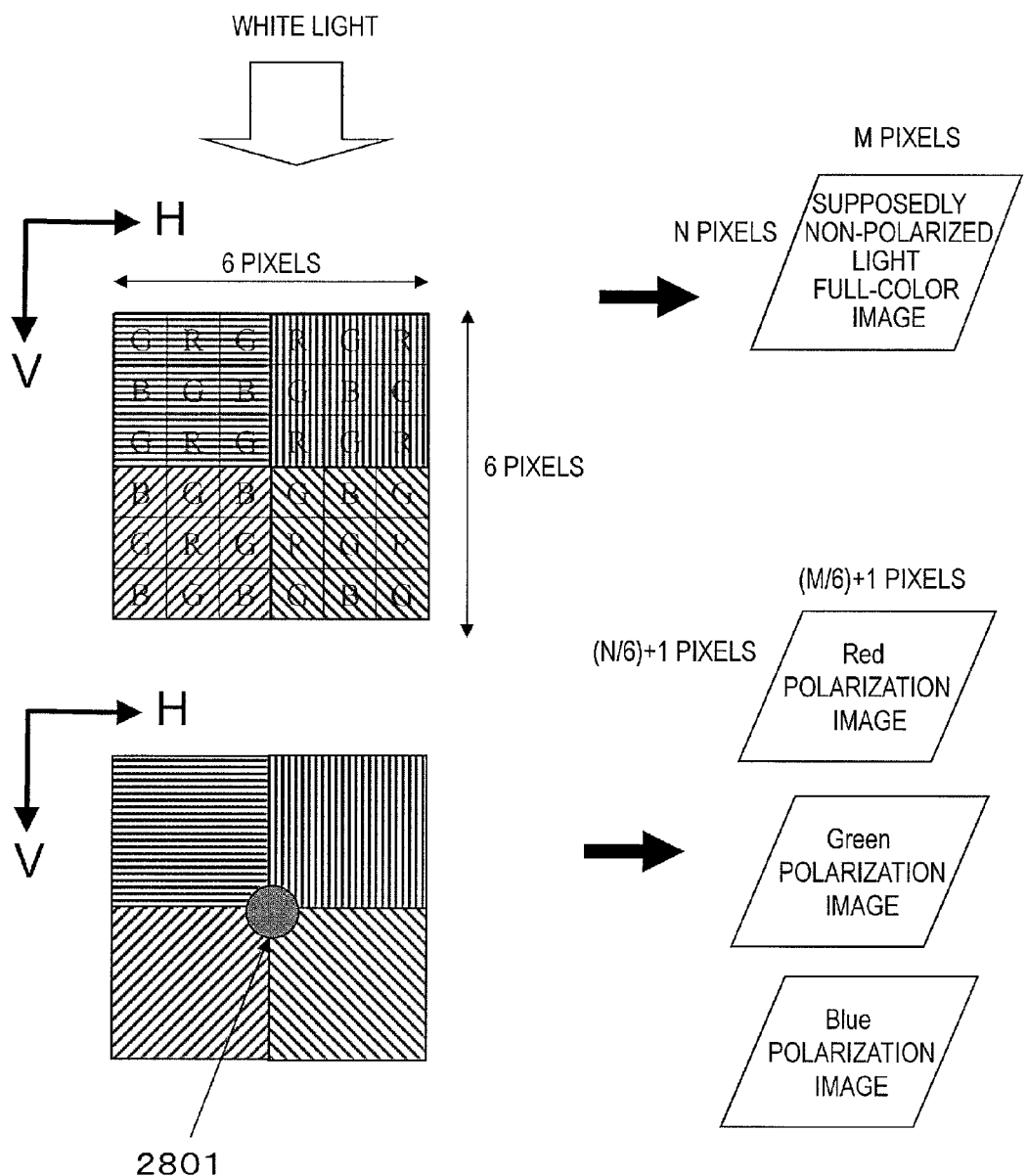
FIG. 5 shows a plan view illustrating the first embodiment of the present disclosure.

FIG. 5 is a plan view illustrating an exemplary arrangement of pixels in the device shown in FIG. 3. In this embodiment, four kinds of polarization optical elements, two of which have polarized light transmission axes that are different from each other by an azimuth angle of 45 degrees, are arranged adjacent to each other. Also, two different kinds of polarization optical elements, which are adjacent to each other along the H axis of the image, have polarized light transmission axes that define an angle of 90 degrees between them. In the example illustrated in FIG. 5, in each 2×2 pixel region in the polarization optical element array, the upper left and upper right areas have polarized light transmission axes of 0 and 90 degrees, respectively, and the lower left and lower right areas have polarized light transmission axes of 135 and 45 degrees, respectively.

As can be seen, in the polarization image sensor of this embodiment, each of these polarization optical elements covers a plurality of photodiodes and makes light which is polarized in a predetermined direction in a plane that is parallel to the image capturing plane incident onto the optical low-pass filter. The color mosaic filter has a structure in which a plurality of color filters in multiple different colors are arranged two-dimensionally, and the color filters are arranged so that light that has passed through each polarization optical element is transmitted through associated ones of the color filters in multiple different colors.

Specifically, in this embodiment, each single polarization optical element covers 3×3 pixels of a Bayer color mosaic filter. That is why each unit polarization pixel including four different kinds of polarization optical elements corresponds to a 6×6 pixel region of the Bayer color mosaic filter. This corresponding pixel region may be made up of any other number of pixels, too. Thanks to the function of the quartz LPF, the maximum spatial frequency of the pixels decreases to one half. That is why in one pixel in the vicinity of the boundary between adjacent polarization optical elements, the light rays are highly likely to mingle together. For example, if the 3×3 pixels are reduced to 2×2 pixels, then the polarized light detection ability could decline.

In this description, the "Bayer arrangement" refers to an arrangement in which color filters in the three colors of R (red), G (green) and B (blue) are separately arranged in two columns and two rows to form four regions. In two diagonal ones of those four regions, arranged are G (green) color filters. However, the arrangement of the color mosaic filter does not have to be such a Bayer arrangement but may also be any other arrangement as long as a number of units, each of which is comprised of at least three color filters, are arranged periodically. The same statement will apply to each of the other embodiments to be described later.

Next, the resolution of the output image will be described.

First of all, a non-polarized presumptive full-color image is generated as an image consisting of M×N pixels through Bayer mosaic interpolation processing. Meanwhile, a polarization image is obtained using four different kinds of polarization optical elements as one unit and using the center pixel as a point 2801. Since the number of pixels included in this one unit is 6×6, the resolution of the color polarization image becomes ((M/6) 1)×((N/6) 1).

As can be seen, if a non-polarized presumptive full-color image is generated, then a color image, of which the resolution is as high as the maximum resolution of the original image sensor, can be obtained. On the other hand, in the case of a polarization image, the resolution decreases somewhat, but polarization images can be obtained on a color-by-color basis, which is beneficial.

Figure 6:
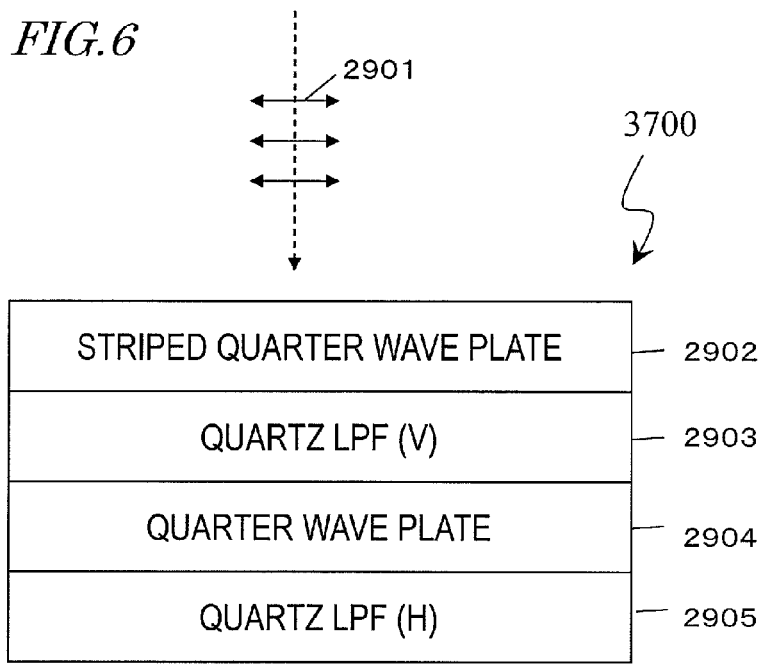
FIG. 6 shows a cross-sectional view illustrating the structure of a quartz LPF for use in the first embodiment of the present disclosure.

FIG. 6 illustrates an optical LPF 3700 for use in the embodiment shown in FIG. 3. This optical LPF 3700 has been formed by stacking quarter wave plates and quartz LPFs one upon the other in multiple layers. Since the incoming light 2901 that has been transmitted through the polarization optical elements is a bundle of linearly polarized light rays, first of all, the incoming light is transformed into a circularly polarized light ray by a striped quarter wave plate 2902. The polarization direction of the linearly polarized light is defined by the directions of the polarized light transmission axes of the polarization optical elements. In this embodiment, the directions of the polarized light transmission axes of the polarization optical elements that have transmitted the incoming light define four different angles of 0, 45, 90 and 135 degrees with respect to the reference axis. Thus, the linearly polarized light that has been incident on the quartz LPF 3700 has four different polarization directions.

Figure 7:
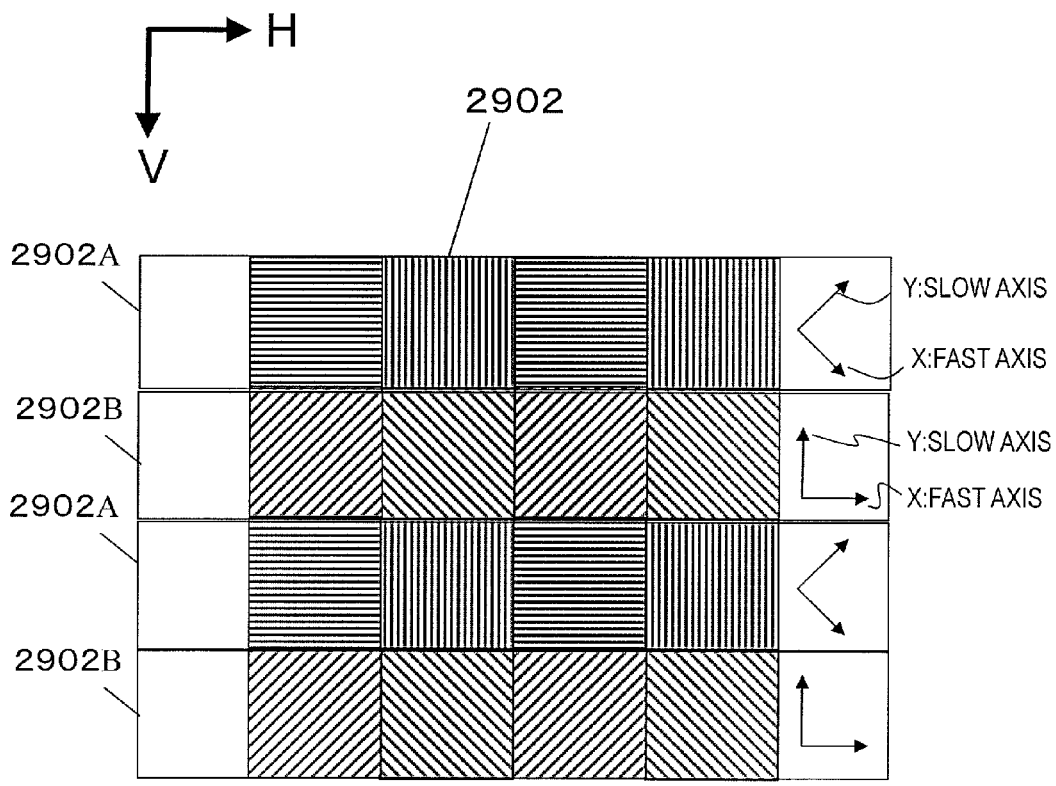
FIG. 7 shows a plan view illustrating a striped quarter wave plate of the quartz LPF for use in the first embodiment of the present disclosure.

FIG. 7 illustrates the two-dimensional structure of this striped quarter wave plate 2902, which plays the role of producing a circularly polarized light ray based on the four different kinds of linearly polarized light rays. This striped quarter wave plate 2902 has a structure in which two kinds of stripes 2902A and 2902B that run in the direction H shown in FIG. 7 are alternately arranged in the direction V shown in FIG. 7. For your reference, polarization optical elements are also shown in FIG. 7.

Each stripe 2902A is associated with a row of polarization optical elements that have two different azimuth angles of 0 and 90 degrees. In the stripe 2902A, the X (fast) and Y (slow) axes of the quarter wave plate are arranged to define a tilt angle of 45 degrees with respect to the direction in which the stripe 2902A runs. In this description, the "fast axis" is an axis, of which the refractive index becomes minimum with respect to light that is polarized parallel to its axial direction, while the "slow axis" is an axis, of which the refractive index becomes maximum with respect to the light that is polarized parallel to its axial direction. In other words, the light polarized in the fast axis direction propagates through a birefringent material at a relatively high phase velocity, while the light polarized in the slow axis direction propagates through a birefringent material at a relatively low phase velocity.

Each stripe 2902B is associated with a row of polarization optical elements that have two different azimuth angles of 45 and 135 degrees. In the stripe 2902B, the X (fast) and Y (slow) axes of the quarter wave plate are arranged to define an angle of 0 or 90 degrees with respect to the direction in which the stripe 2902B runs.

As can be seen, according to this embodiment, an arrangement in which the polarized light transmission axes of the polarization optical elements intersect with the X (fast) and Y (slow) axes of the striped quarter wave plate 2902 at an angle of 45 degrees is realized between the polarization optical elements and the stripe 2902A or 2902B that face each other. As a result, every one of the four different kinds of linearly polarized light rays can be transformed into circularly polarized light ray. By alternately arranging, in the column direction, rows in which the polarized light transmission axes of the polarization optical elements have azimuth angles of 0 and 90 degrees and rows in which the polarized light transmission axes of the polarization optical elements have azimuth angles of 45 and 135 degrees, the configuration and effects of the embodiment described above are realized. The striped quarter wave plate may be made by a resin fine line patterning technique as disclosed in Makiko Imae et al., Optimum Design of Wide-band Quarter Wave Plates (QWPs) Utilizing Form Birefringence, KONICA MINOLTA TECHNOLOGY REPORT VOL. 3 (2006), pp. 62-67, for example.

Now take a look at FIG. 6 again. After having been transmitted through the striped quarter wave plate 2902, the incoming light is split in the vertical (V) direction by a quartz LPF (V) 2903 into two light rays. Next, those two light rays are transformed into circularly polarized light rays through another quarter wave plate 2904. Then, each of those light rays is split into two in the horizontal (H) direction through a quartz LPF (H) 2905 in turn, thereby splitting the incoming light into four light rays to be incident on their associated four pixels of the Bayer color mosaic filter.

(Embodiment 2)

Figure 8:
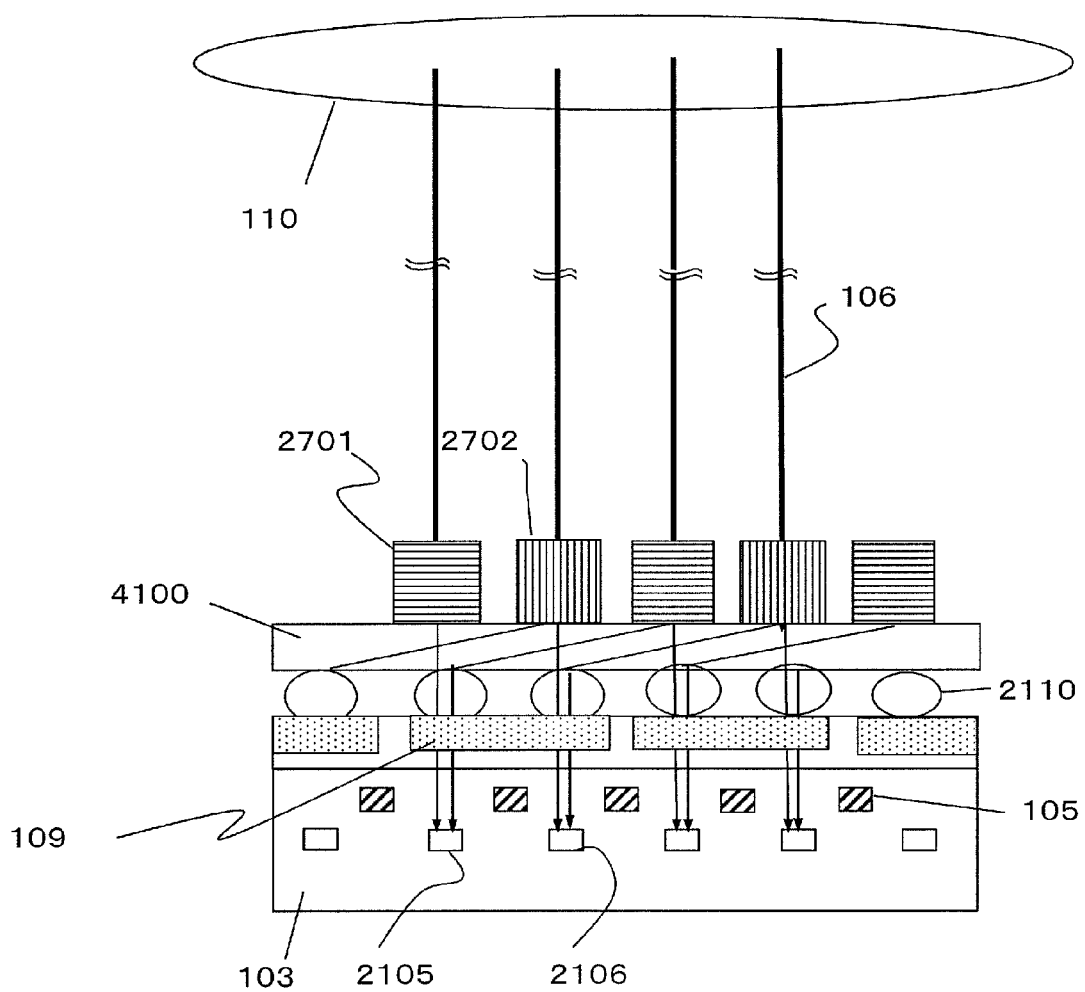
FIG. 8 shows a cross-sectional view illustrating a second embodiment of the present disclosure.

FIG. 8 illustrates an exemplary cross-sectional structure for a polarization image sensor as a second embodiment of the present disclosure. In this embodiment, the intensities of polarization pixels are averaged in a single color of the color mosaic. As a result, an ordinary intensity can be obtained, and therefore, an ordinary full color image and a color polarization image can be both obtained. In that case, the resolution of the color polarization image will decrease less than that of the full color image, which is advantageous, too.

In the cross-sectional view shown in FIG. 8, the incoming light is transmitted through an objective lens 110, polarization optical elements 2701, 2702, an optical LPF (low-pass filter) 4100, micro lenses 2110, and a color mosaic filter 109 and then incident on photodiodes 2105 and 2106.

In the first embodiment described above, a single polarization optical element is associated with a plurality of pixels in multiple different colors in the Bayer color mosaic filter. On the other hand, according to this embodiment, a region covered by a single-color unit 109 of the color mosaic filter is associated with a plurality of polarization optical elements 2701, 2702 and a plurality of photodiodes (pixels) 2105, 2106.

According to such a configuration, when polarization images are obtained on a color-by-color basis, the resolution does not decrease substantially, which is beneficial. The optical LPF 4100 makes split light rays incident on the color mosaic filter, thereby achieving the effect of eliminating the moiré and false colors. To achieve these effects, in this embodiment, either non-polarized light rays or circularly polarized light rays are made to be incident on the quartz LPF included in the optical LPF 4100. If polarized light rays with four different polarization directions are coming in combination as in this embodiment, the effect of eliminating the moiré and false colors cannot be achieved just by using a known optical LPF. According to this embodiment, a stack of quartz LPFs and quarter wave plates is used with the spatial frequencies of the color and polarization mosaics in combination and the cutoff frequency of the optical LPF taken into account, thereby achieving the effect of eliminating the moiré and false colors.

Figure 9:
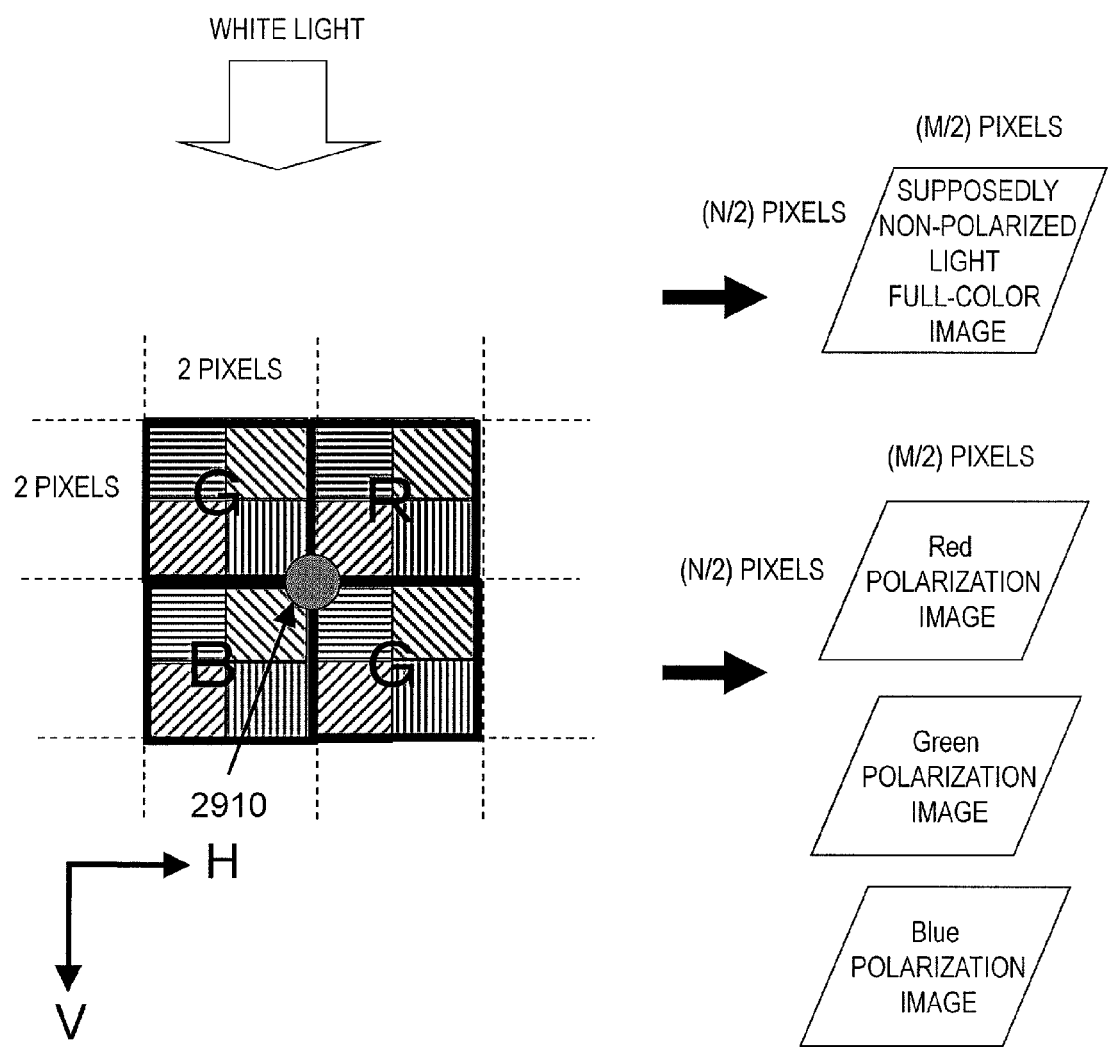
FIG. 9 shows a plan view illustrating the second embodiment of the present disclosure.

FIG. 9 is a plan view illustrating an exemplary arrangement of color filters and polarization optical elements according to this embodiment. In the example illustrated in FIG. 9, color filters in the three primary colors of R (red), G (green) and B (blue) form a Bayer arrangement. The color filters in these three colors are arranged in two columns and two rows to form four regions. In two out of those four regions, G (green) color filters are arranged. However, this is not the only arrangement of color filters according to this embodiment.

In this embodiment, one color filter in a single color is associated with four different polarization optical elements with mutually different polarized light transmission axis directions. That is to say, each single-color region of the Bayer color mosaic filter is associated with a basic unit of the polarization optical element array. Each basic unit is made up of four polarization optical elements which are arranged in two columns and two rows. Also, in each basic unit, two adjacent ones of the polarization optical elements have polarized light transmission axes that are different from each other by an azimuth angle of 45 degrees. Meanwhile, photodiodes are arranged so as to face polarization optical elements one to one. For example, one R (red) color filter is associated with four polarization optical elements and four photodiodes. That is why when a non-polarized color image is going to be output, a light intensity signal is generated for a single pixel by subjecting four different polarization pixels to averaging processing. Consequently, the pixel resolution decreases to (M/2)×(N/2). However, even when a color polarization image is output, the pixel center of the polarization image is also located at the point 2910, and therefore, the same resolution of (M/2)×(N/2) pixels can be maintained. In this description, the respective photodiodes that are associated with one color filter in a single color and that are arranged in two columns and two rows will be sometimes referred to herein as "sub-pixels".

Figure 10:
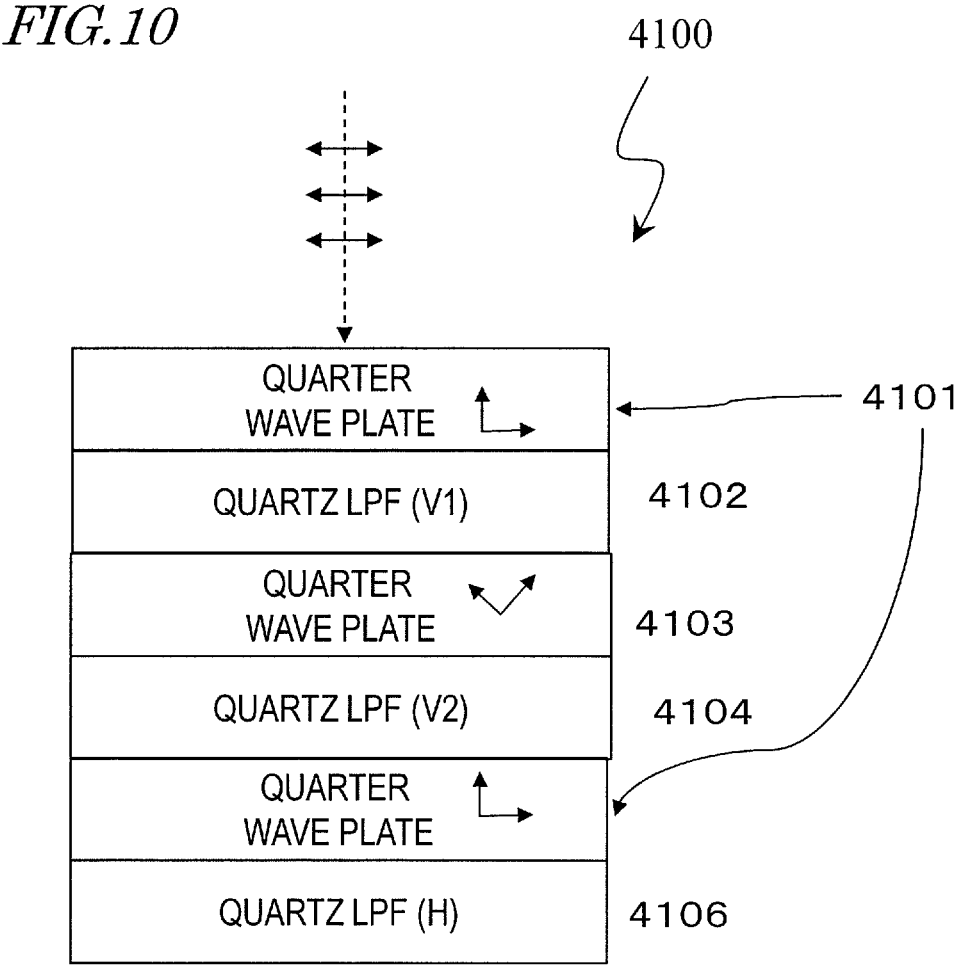
FIG. 10 shows a cross-sectional view illustrating the structure of a multilayer optical LPF for use in the second embodiment of the present disclosure.

FIG. 10 illustrates an exemplary cross-sectional structure for a multilayer optical LPF 4100 for use in the configuration shown in FIG. 8. The optical LPF for use in this embodiment is configured to shift at least a part of light ray that has been transmitted through each of the polarization optical elements parallel to the image capturing plane by at least the arrangement pitch of the color filters in the color mosaic filter. More specifically, one period of the two-dimensional arrangements of the polarization optical elements and the photodiodes has a spatial frequency which is an integral number of times as high as the cutoff frequency of the optical low-pass filter. And the optical low-pass filter has a uniform optical property in a plane that is parallel to the image capturing plane.

As described above, the optical LPF 4100 has been formed by stacking quarter wave plates and quartz LPFs one upon the other in multiple layers. More specifically, the optical LPF plate 4100 includes a quarter wave plate 4101, of which the fast and slow axes are defined in the horizontal and vertical directions, respectively, a quartz LPF (V1) 4102 which has a birefringent property to shift light by two pixels vertically downward (i.e., in the positive direction along the Y-axis), another quarter wave plate 4103, of which the fast and slow axes are arranged to define a tilt angle of 45 degrees with respect to the horizontal and vertical directions, respectively, a quartz LPF (V2) 4104 which has a birefringent property to shift light by two pixels vertically upward (i.e., in the negative direction along the Y-axis), another quarter wave plate 4101, of which the fast and slow axes are defined in the horizontal and vertical directions, respectively, and a quartz LPF (H)

4106 which has a birefringent property to shift light by two pixels in the horizontal (H) direction. These quarter wave plates and quartz LPFs are stacked one upon the other in this order so that the quarter wave plate 4101 is closer to the light source than any other member of this multilayer structure.

Each quarter wave plate plays the role of transforming a linearly polarized light ray into a circularly polarized light ray. That is why this optical LPF 4100 is configured so that the optic axis of each of the multiple quarter wave plates stacked defines a tilt angle of 45 degrees with respect to the linearly polarized light ray that has been incident on the quarter wave plate.

Figure 11:
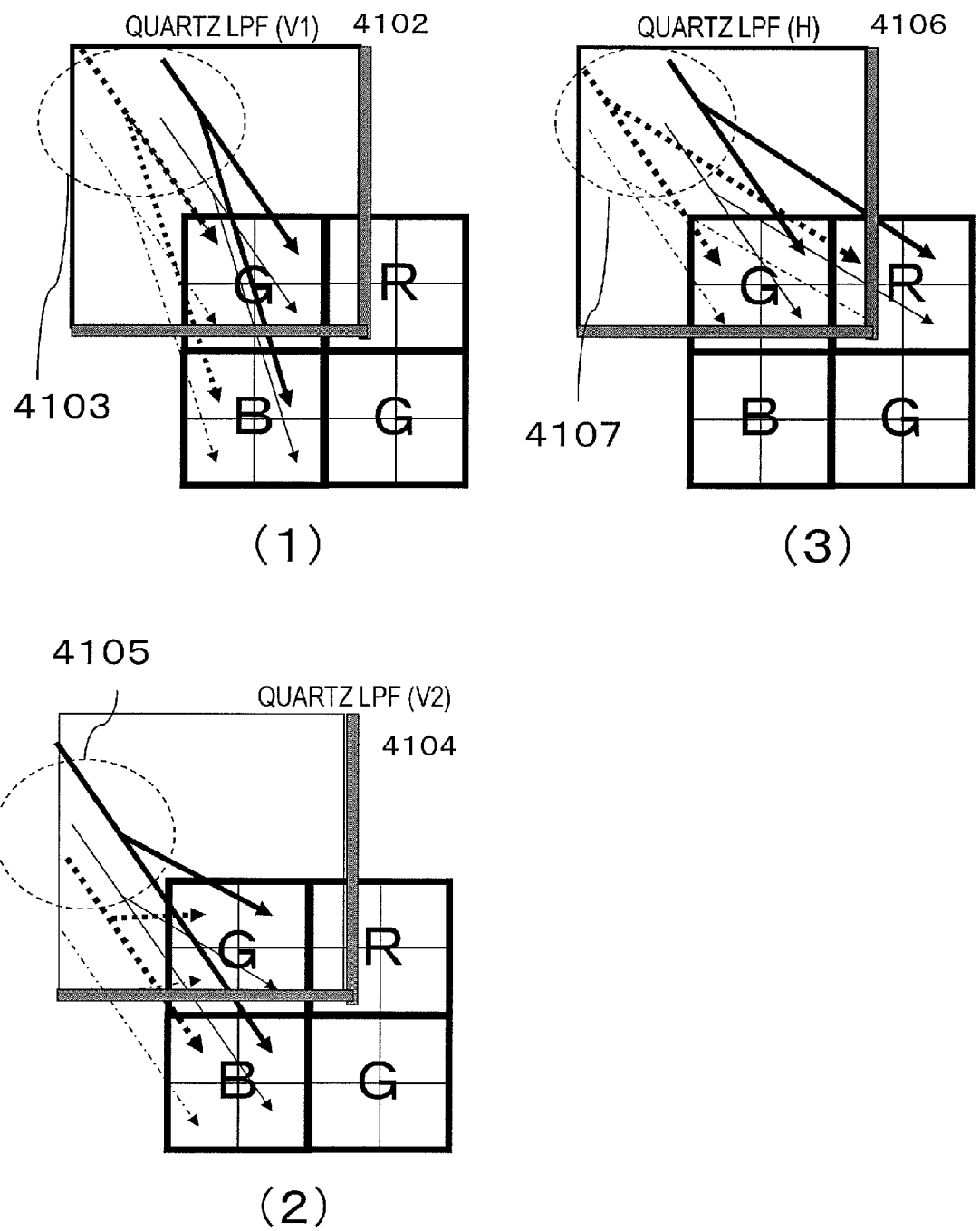
FIG. 11 shows the relation between the magnitudes of light ray shifts caused by quartz LPFs and a color mosaic and a polarization mosaic.

FIG. 11 shows the relation between the magnitudes of light ray shifts caused by the quartz LPFs in the optical LPF 4100 and the color mosaic and polarization mosaic. Portion (1) of FIG. 11 illustrates how light rays that have been transmitted through the quartz LPF (V1) 4102 are incident on the color mosaic that is located under the optical LPF 4100. On the drawings, those light rays are illustrated as coming from obliquely over the optical LPF 4100 for convenience sake. Each quartz LPF plays the role of eliminating moiré and false colors from the color mosaic, and therefore, shifts the light rays by one color (i.e., by two pixels) vertically downward.

For example, a group of non-polarized light rays 4103 that are going to enter the four subpixels of a G pixel is split by the quartz LPF (V1) 4102 into light rays to be incident on the target subpixels of the G pixel and light rays to be incident on subpixels of a B pixel that have the same polarized light transmission axes as their counterparts of the G pixel. And those light rays superpose one upon the other.

Likewise, portion (2) of FIG. 11 illustrates how non-polarized light rays that have been transmitted through the quartz LPF (V2) 4104 are incident on the color mosaic that is located under the optical LPF 4100. The light rays are shifted by one color (i.e., by two subpixels) of the color mosaic vertically upward. For example, a group of non-polarized light rays 4105 that are going to enter the subpixels of a B pixel is split into light rays to be incident on the target subpixels of the B pixel and light rays to be incident on subpixels of a G pixel that have the same polarized light transmission axes as their counterparts of the B pixel. And those light rays superpose one upon the other.

Likewise, portion (3) of FIG. 11 illustrates how non-polarized light rays that have been transmitted through the quartz LPF (H) 4106 are incident on the color mosaic that is located under the optical LPF 4100. The light rays are shifted by one color (i.e., by two pixels) of the color mosaic horizontally rightward. For example, a group of non-polarized light rays 4107 that are going to enter the subpixels of a G pixel is split into light rays to be incident on the target subpixels of the G pixel and light rays to be incident on subpixels of an R pixel that have the same polarized light transmission axes as their counterparts of the G pixel. And those light rays superpose one upon the other.

Figure 12:
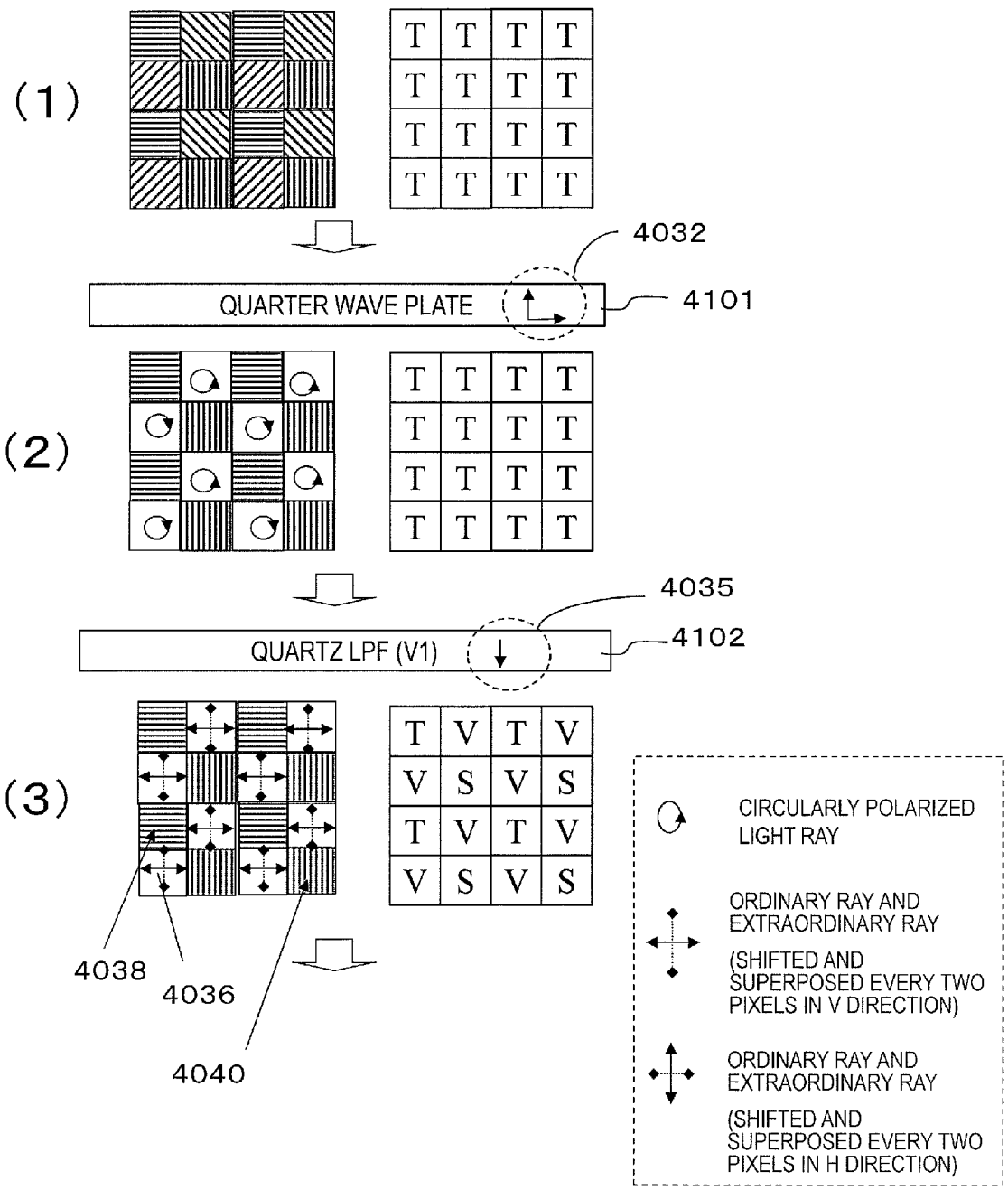
FIG. 12 illustrates sequentially a process through which the light that has been transmitted through a multilayer optical LPF turns into pixel values on color mosaic pixels (Part 1).
Figure 13A:
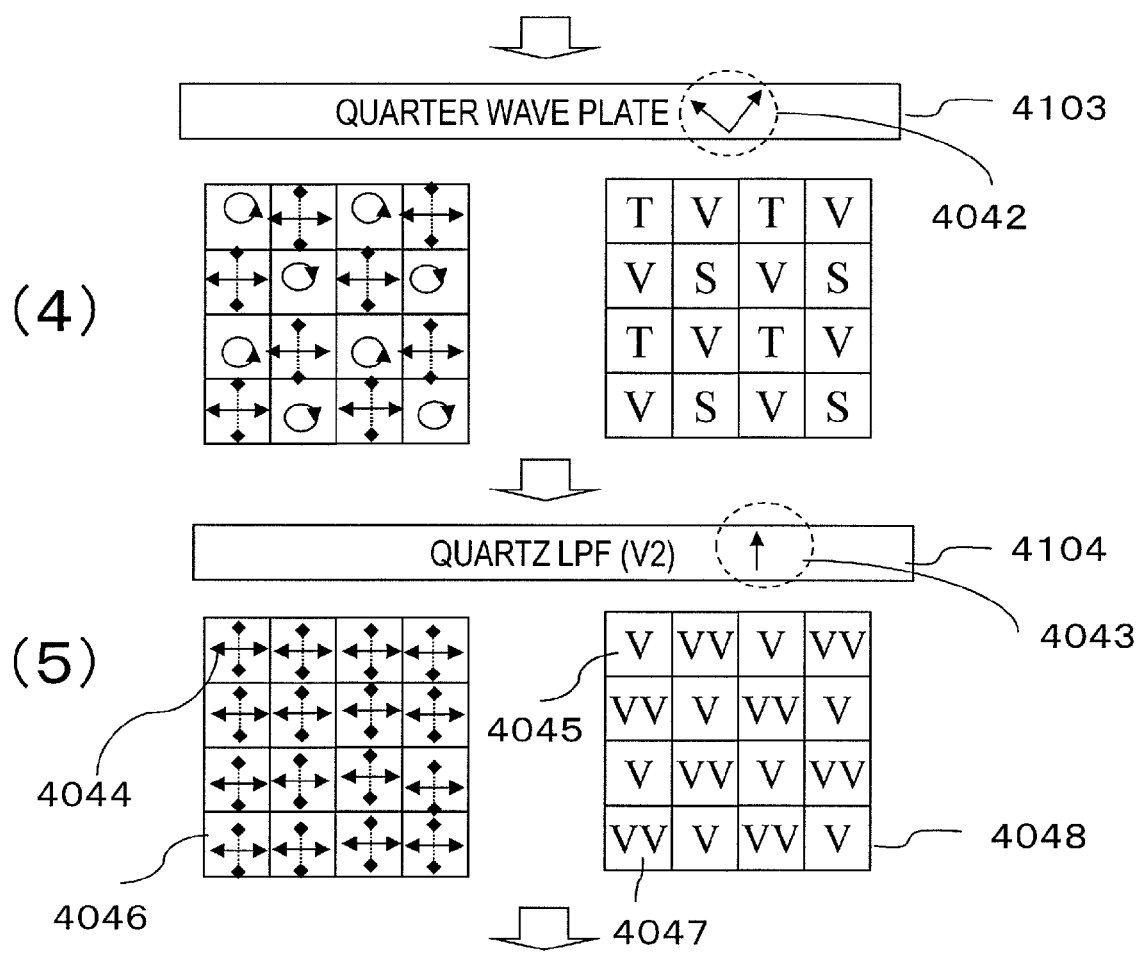
FIG. 13A illustrates sequentially a process through which the light that has been transmitted through a multilayer optical LPF turns into pixel values on color mosaic pixels (Part 2).
Figure 13B:
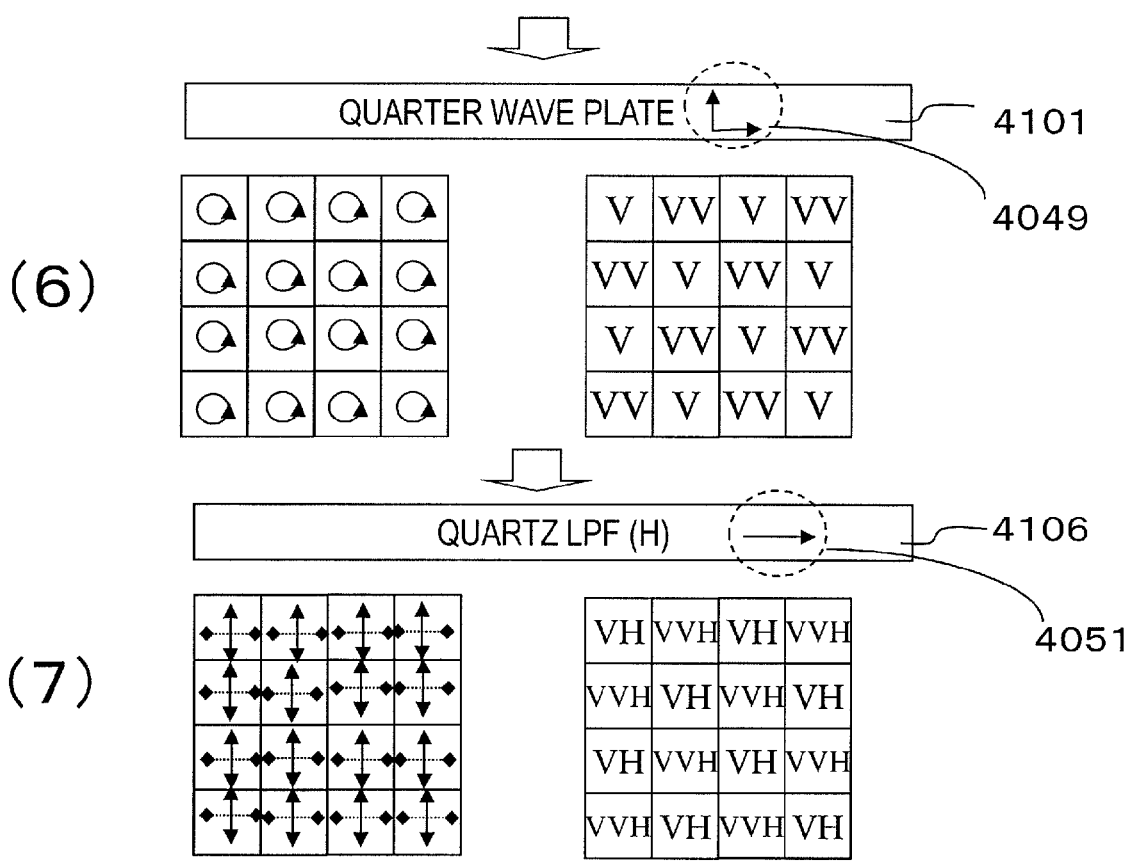
FIG. 13B illustrates sequentially a process through which the light that has been transmitted through a multilayer optical LPF turns into pixel values on color mosaic pixels (Part 3).

Next, it will be described with reference to FIGS. 12, 13A and 13B how the incoming light has its polarization state changed and is shifted while being transmitted through the multilayer optical LPF 4100 shown in FIG. 10. In FIGS. 12, 13A and 13B, schematically shown are polarization states on the left-hand side and the pixel values of the light on the right-hand side, respectively. In this description, the "pixel value" represents the quantity of energy to be observed with the light shifting and superposing states at the subpixels taken into consideration. In FIGS. 12, 13A and 13B, illustrated are 4×4 subpixels to be included in 2×2 color pixels (G, R, B, G) that form a basic unit of the Bayer mosaic arrangement.

First of all, look at portion (1) of FIG. 12, which illustrates the states of light rays that have just been transmitted through 4×4 polarization optical elements and incident on the 4×4 subpixel regions. The polarization optical elements produce linearly polarized light rays, any two of which have polarization directions that are different from each other by 45 degrees, for the respective subpixels, and those linearly polarized light rays are incident on the quarter wave plate 4101 shown in FIG. 10. The light rays that have been transmitted through the polarization optical elements maintain their original quantity of energy. Such a state is indicated by T (=through) in FIG. 12.

Portion (2) of FIG. 12 illustrates the states of the light rays that have just been transmitted through the quarter wave plate 4101. In portion (2) of FIG. 12, the closed circle arrow indicates a circularly polarized light ray. In the quarter wave plate 4101, the directions 4032 of the fast and slow axes are either parallel or perpendicular to the reference direction (which is either the horizontal direction H or the vertical direction V shown in FIG. 9). That is why pixels in which the light rays transmitted through the quarter wave plate 4101 are circularly polarized and pixels in which the light rays transmitted through the quarter wave plate 4101 are linearly polarized light form a checkerboard pattern. However, the pixel values remain the same as shown on the right-hand side of portion (2) of FIG. 12.

Portion (3) of FIG. 12 illustrates the states of the light rays that have just been transmitted through the quartz LPF (V1) 4102. Some of the subpixel regions have a horizontal solid arrow and a line segment which crosses the arrow at right angles. The horizontal solid arrow indicates the polarization direction of an ordinary ray that does not shift. On the other hand, the line segment indicates the polarization direction of an extraordinary ray that does shift. In each of these subpixel regions with these signs, the light ray (extraordinary ray) shifts every two pixels in the V direction and gets superposed on an ordinary ray. As already described with reference to FIG. 11, the light ray shifts by two subpixels vertically downward in the direction 4035 of the optic axis of this quartz LPF. In this case, in a subpixel through which a circularly polarized light ray is supposed to pass originally, the light ray is split into an ordinary ray and an extraordinary ray, which are superposed one upon the other. That is why in the subpixel region 4036 on which a circularly polarized light ray is incident as shown in portion (2) of FIG. 12, the pixel value has been obtained by averaging the sum of the subpixel values in the V direction. On the other hand, the subpixel regions 4038 and 4040 on which a linearly polarized light ray with a 0 degree polarization direction and a linearly polarized light ray with a 90 degree polarization direction are incident come to have the no change (through) state and a state S in which the light ray has been shifted by two subpixels in the V direction, respectively.

Portion (4) of FIG. 13A illustrates the states of the light rays that have just been transmitted through the quarter wave plate 4103. Since the directions 4042 of the fast and slow axes define a tilt angle of 45 degrees with respect to the reference direction, subpixels in which the light rays transmitted are circularly polarized and subpixels in which ordinary and extraordinary rays superpose one upon the other form a checkerboard pattern. However, even if the light rays are transmitted through a phase plate such as the quarter wave plate 4103, the pixel values remain unchanged from the ones shown in portion (3) of FIG. 12.

Portion (5) of FIG. 13A illustrates the states of the light rays that have just been transmitted through the quartz LPF (V2) 4104. Each light ray shifts by two subpixels vertically upward in the direction 4043 of the optic axis of this quartz LPF. In this case, in the subpixel region 4044 on which a circularly polarized light ray has been incident on the quartz LPF (V2) 4104, the circularly polarized light ray is split into an ordinary ray and an extraordinary ray, which are superposed one upon the other as shown on the left-hand side of portion (5) of FIG. 13A. That is why its pixel value 4045 has been obtained by averaging the sum of the pixel values in the V direction. On the other hand, in the subpixel region 4046 in which an ordinary ray and an extraordinary ray that have been split superpose one upon the other before being incident on the quartz LPF (V2) 4104, the ordinary ray is just transmitted through the subpixel region 4046 but the extraordinary ray shifts. Consequently, such a subpixel region 4046 comes to have a pixel value 4047 that is obtained by averaging the sum of the pixel values in the V direction again. Such a pixel value 4047 will be identified herein by VV. In the subpixel region 4048 identified by S at the stage shown in portion (4) of FIG. 13A, the light ray has shifted by two subpixels vertically downward in the V direction. However, as a result of this averaging, the light ray shifts upward. Consequently, the shift can be canceled and averaging can get done in the V direction at the same time.

Portion (6) of FIG. 13B illustrates the states of the light rays that have just been transmitted through the quarter wave plate 4101. In the quarter wave plate 4101, the directions 4049 of the fast and slow axes are either parallel or perpendicular to the reference direction. That is why the light ray turns into a circularly polarized light ray in every subpixel region. The pixel values remain unchanged from the ones shown in portion (5) of FIG. 13A.

Portion (7) of FIG. 13B illustrates the states of the light rays that have just been transmitted through the quartz LPF (H) 4106. Every subpixel region has a vertical solid arrow and a line segment which crosses the arrow at right angles. The vertical solid arrow indicates the polarization direction of an ordinary ray that does not shift. On the other hand, the line segment indicates the polarization direction of an extraordinary ray that does shift. In each subpixel region, the light ray (extraordinary ray) shifts every two pixels in the H direction and gets superposed on an ordinary ray. The light ray shifts by two pixels horizontally rightward in the direction 4051 of the optic axis of this quartz LPF 4106. In every subpixel region, the circularly polarized light ray is split into an ordinary ray and an extraordinary ray, which are superposed one upon the other. And their pixel values are added together and averaged in the H direction. In portion (7) of FIG. 13B, such a state is identified by either VH or VVH.

In this manner, the light rays that have been transmitted through the polarization optical elements 2701 and 2702 shown in FIG. 8 and have entered the multilayer optical LPF 4100 (i.e., linearly polarized light rays of which the polarization directions change from one subpixel to another) go through the process steps shown in FIG. 12 and portion (1) of FIG. 13A through portion (7) of FIG. 13B to be incident on the color mosaic filter. Thereafter, those light rays are converted into pixel signals by photodiodes associated with the respective subpixels. Since light rays that have been transmitted through the respective polarization optical elements are incident on the color mosaic filter after having shifted by two subpixels vertically and horizontally (i.e., in the V and H directions) and having been added together and averaged, no moiré or false colors will be produced there.

In the embodiment described above, an optical LPF (low-pass filter) 4100 in which three quarter wave plates and three quartz LPFs are stacked one upon the other is supposed to be used. However, any other optical LPF (low-pass filter) may also be used. For example, even if an optical low-pass filter, including a first quarter wave plate, a first birefringent low-pass filter layer, a second quarter wave plate and a second birefringent low-pass filter layer that are stacked in this order so that the first quarter wave plate is closer to the light source than any other member of the low-pass filter, is used, the moiré pattern can also be reduced to a certain degree, albeit less effectively than with the optical LPF described above. If a third quarter wave plate and a third birefringent low-pass filter are further stacked in this order between the second birefringent low-pass filter layer and the color mosaic filter, the effect of reducing the moiré pattern can be achieved more significantly.

Figure 14:
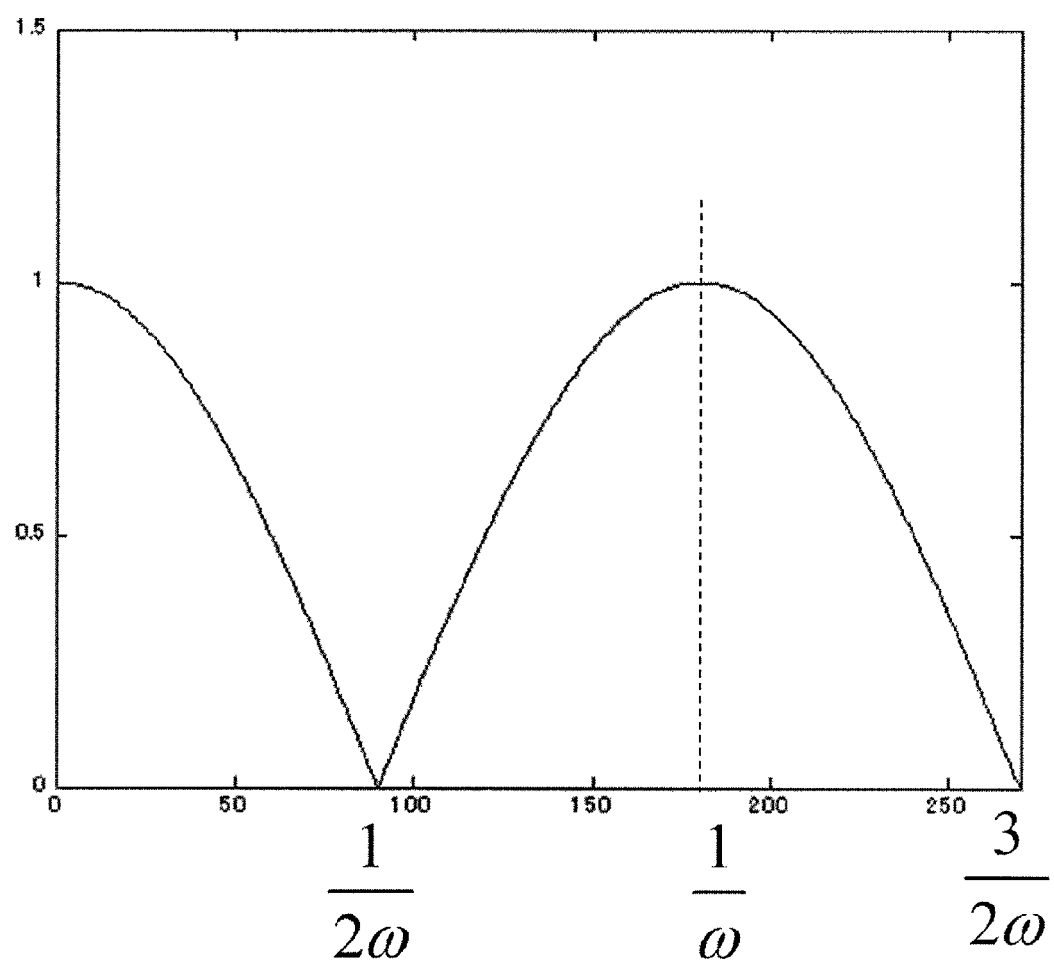
FIG. 14 shows a graph showing the frequency characteristic of a multilayer optical LPF for use in the second embodiment of the present disclosure.

FIG. 14 shows the spatial frequency characteristic of a quartz LPF according to this embodiment. The same quartz LPF as the one adopted in the first embodiment described above may also be used. Supposing the pixel to pixel distance is ω, the cutoff frequency of the quartz LPF is ½ω, which corresponds to the frequency of a Bayer color mosaic filter.

As can be seen from FIG. 14, 1/ω which is twice as high as the cutoff frequency falls within the transmission frequency range again. And this frequency 1/ω agrees with the frequency of the polarization optical elements with four polarization directions. Thanks to this property, even if a quartz LPF is used, a light intensity distribution with a high spatial frequency, which is generated by polarization optical elements with four polarization directions that are covered by a single-color pixel, can be received as it is according to this embodiment by photodiodes without being affected by the LPF. Since the transmission frequency range of the optical low-pass filter is an even number of times as high as the cutoff frequency, the spatial frequency of the arrangement of polarization optical elements or photodiodes may also be an even number of times as high as the cutoff frequency of the optical low-pass filter.

In this description, every exemplary configuration that includes a quartz LPF is supposed to be a single-panel color image sensor that uses a Bayer color mosaic. However, this embodiment is also applicable to any color mosaic arrangement other than the Bayer one. In addition, this embodiment is also applicable effectively to even a monochrome image sensor that does not use any color filter, because a quartz LPF is sometimes used for a monochrome image sensor to eliminate a moiré pattern during pixel sampling.

Generally speaking, if an endoscope tries to obtain a color image and a polarization image at a time, then a significant quantity of light will be lost and the sensitivity of the resultant image will decrease significantly.

An endoscope can obtain color information either by frame sequential method or synchronous method. In any case, RGB images are generated using only one-third of the total quantity of energy of white light, and the rest of the energy is absorbed into color filters. That is to say, the quantity of light that can be used effectively to generate a color image is only one-third of the total quantity of the incoming light. And if a polarization filter is operated, an ordinary polarization filter with a extinction ratio of approximately 1000 to 1 will absorb a P wave or an S wave entirely, and therefore, the quantity of light that can be used will further decrease to one half. That is to say, in order to obtain both color information and polarization information, the quantity of light that can be converted into an electrical signal by a photodiode of an image sensor will decrease to just one-sixth of the quantity of the incoming light.

In the field of endoscopes, there are great demands for a high-sensitivity image. Even though an image captured with a narrow-band spectroscopic color illumination has been used recently, the resultant image will be darker (i.e., the sensitivity will drop) in that case, which is a serious problem. In this case, if such a spectroscopic image is replaced with a polarization image, then there is a chance that a bright color image can be obtained. Actually, however, only a dark image can be obtained, and it is difficult to capture a polarization image using an endoscope in practice.

A conventional polarization image sensor uses an existent polarization filter element which usually has as high a extinction ratio as 100 or more. That is why if non-polarized light that has come from an ordinary light source is incident on such a polarization image sensor, the quantity of the light that can be transmitted through the polarization filter element will be one-half, and therefore, a dark, low-sensitivity image will be obtained in the end.

The present disclosure provides a polarization image sensor which can obtain a bright image and polarization information at the same time and which can be used effectively in an endoscope.

Figure 15:
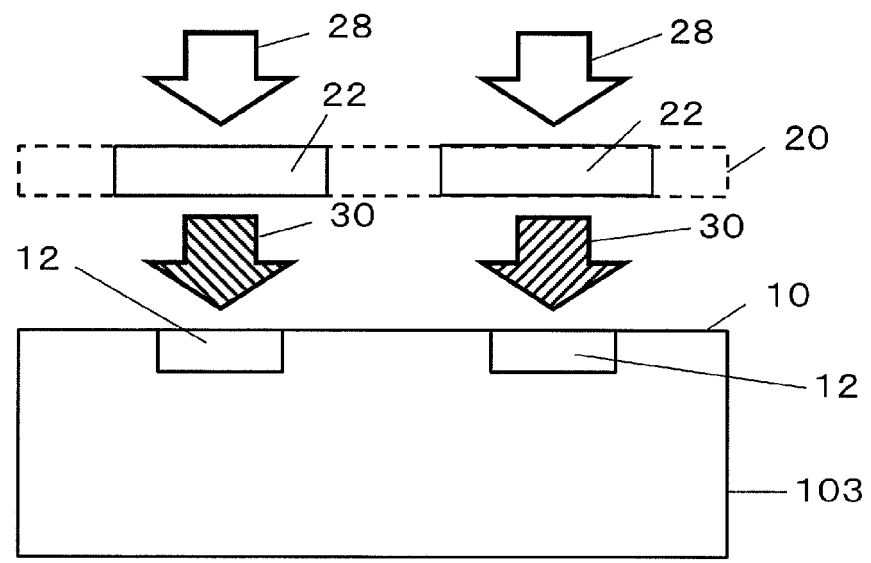
FIG. 15 shows a cross-sectional view schematically illustrating an exemplary basic configuration for a polarization image sensor according to the present disclosure.

FIG. 15 is a cross-sectional view schematically illustrating an exemplary basic configuration for polarization image sensor according to the present disclosure. The polarization image sensor of the present disclosure includes a plurality of photodiodes 12 which are arranged on an image capturing plane 10 and each of which converts light into an electrical signal, and an optical element array 20 which covers these photodiodes 12. The optical element array includes a plurality of optical elements 22 which are arranged two-dimensionally in a plane that faces the image capturing plane 10. In FIG. 15, only two of those photodiodes 12 are shown. Actually, however, a much greater number of photodiodes 12 are arranged two-dimensionally on the image capturing plane 10. Likewise, only two of those optical elements 22 included in the optical element array 20 are shown in FIG. 15. Actually, however, a far greater number of optical elements 22 are included in the optical element array 20.

A light ray 28 is incident on each optical element 22, of which a light ray 30 goes out. Thanks to the function of the optical element 22, the degree of polarization of the light ray 30 becomes higher than that of the light ray 28. The degree of polarization is increased due to the refraction caused by the optical element 22. That is why the optical element 22 may be called a "refractive polarizer".

Figure 16:
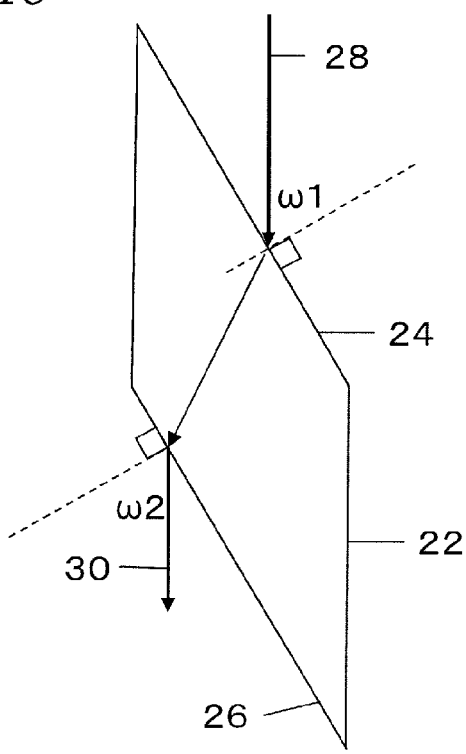
FIG. 16 shows a cross-sectional view illustrating an exemplary optical element which may be used in a polarization image sensor according to the present disclosure.

In FIG. 15, each optical element 22 is illustrated simply as having a rectangular cross section. Actually, however, the optical element 22 has at least one surface that refracts light. As shown in FIG. 16, such an optical element 22 may be implemented as a prism with a parallelogram cross section, which has a first surface 24 on which the light ray 28 is incident and a second surface 26 through which the light ray 30 goes out. In the example illustrated in FIG. 16, the angle of incidence ω1 defined by the light ray 28 with respect to the first surface 24 falls within the range of 55 to 80 degrees, so does the angle of emittance ω2 defined by the light ray 30 with respect to the second surface 26. In this case, the angle of incidence ω1 is the angle formed between a normal (indicated by the dashed line) to the first surface 24 and the incoming light ray 28. On the other hand, the angle of emittance ω2 is the angle formed between a normal (indicated by the dashed line) to the second surface 26 and the outgoing light ray 30. As will be described later, if at least one of the angle of incidence ω1 and the angle of emittance ω2 falls within the range of 55 to 80 degrees, the degree of polarization can be increased due to refraction. In the example illustrated in FIG. 16, the degree of polarization is increased by utilizing the phenomenon that polarized light components become uneven when the light ray 28 is incident on the first surface 24 and when the light ray 30 goes out through the second surface 26. Such a phenomenon will be described in detail later.

Figure 17:
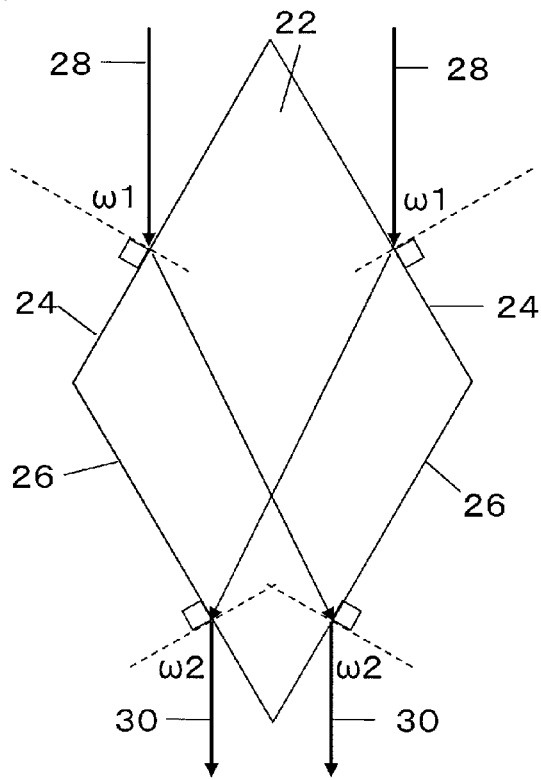
FIG. 17 shows a cross-sectional view illustrating another exemplary optical element which may also be used in a polarization image sensor according to the present disclosure.
Figure 18:
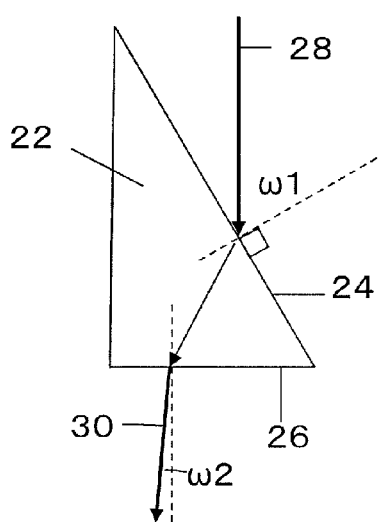
FIG. 18 shows a cross-sectional view illustrating still another exemplary optical element which may also be used in a polarization image sensor according to the present disclosure.
Figure 19:
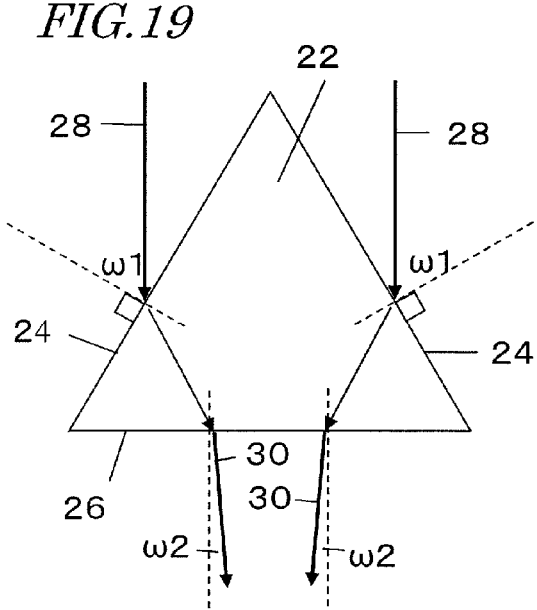
FIG. 19 shows a cross-sectional view illustrating yet another exemplary optical element which may also be used in a polarization image sensor according to the present disclosure.

The optical element 22 may have any of various other shapes. FIGS. 17, 18 and 19 schematically illustrate cross-sectional shapes of some other exemplary optical elements 22 which may be used in the polarization image sensor of the present disclosure. Specifically, in the optical element 22 shown in FIG. 17, the first surface 24 on which the light ray 28 is incident is divided into two light incoming plane portions that tilt in mutually opposite directions. Likewise, the second surface 26 through which the light ray 30 goes out is also divided into two light outgoing plane portions that tilt in mutually opposite directions. In the optical elements 22 shown in FIGS. 18 and 19, the angle of incidence ω1 defined by the light ray 28 with respect to the first surface 24 falls within the range of 55 to 80 degrees, but the angle of emittance ω2 defined by the light ray 30 with respect to the second surface 26 is outside of the range of 55 to 80 degrees. It should be noted that the shapes of the optical elements illustrated in these drawings are just examples of embodiments according to the present disclosure and any other shape may be used as well.

Figure 20A:
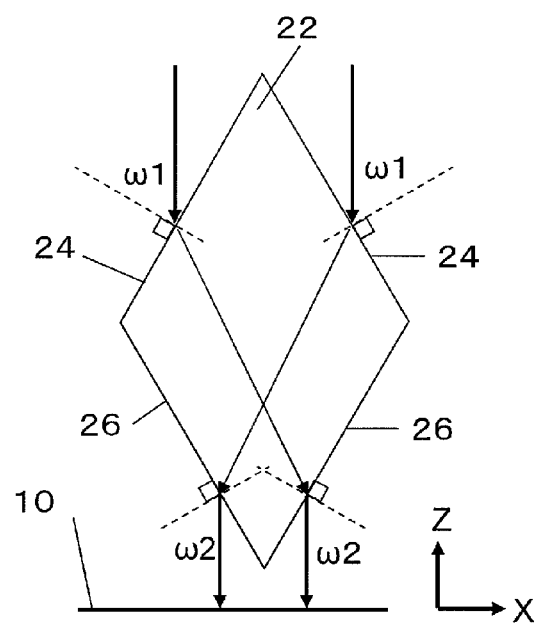
FIG. 20A shows a cross-sectional view of the optical element 22 shown in FIG. 2A.
Figure 20B:
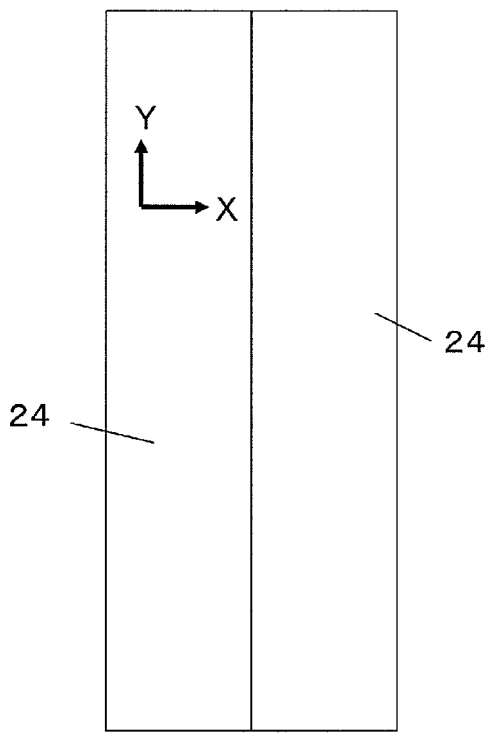
FIG. 20B shows a top view of the optical element 22 shown in FIG. 2A.
Figure 20C:
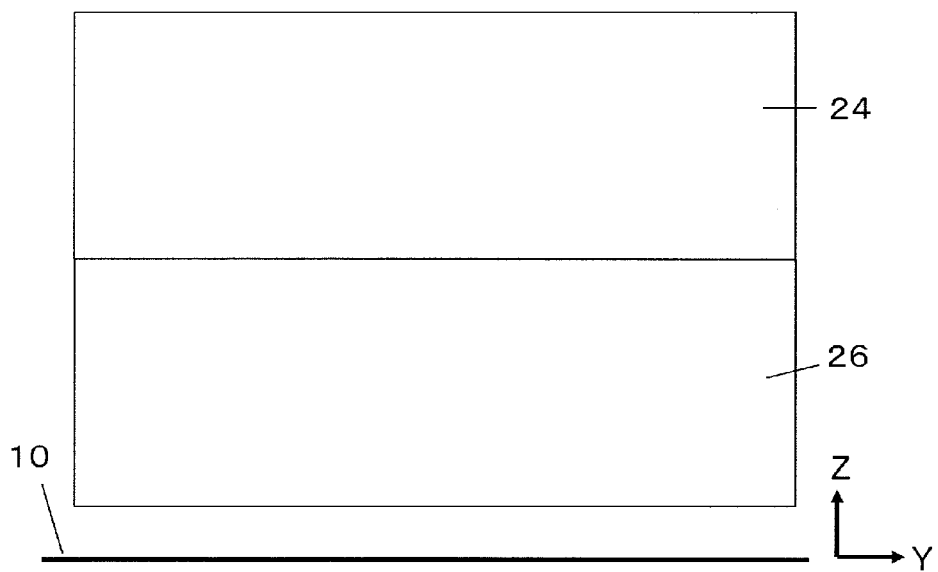
FIG. 20C shows a side view of the optical element 22 shown in FIG. 2A.

FIGS. 20A, 20B and 20C respectively illustrate a cross section, the upper surface and a side surface of the optical element 22 shown in FIG. 17. In this case, an XY plane is supposed to be a plane that is parallel to the image capturing plane 10 and a Z-axis is defined so as to intersect with the image capturing plane 10 at right angles. Then, this optical element 22 has a structure in which two triangular prisms running in the Y-axis direction are combined together. When the optical element 22 is viewed perpendicularly to the image capturing plane 10 (i.e., in the Z-axis direction), a normal (indicated by the dashed line) to the first surface 24 or the second surface 26 of the optical element 22 agrees with the X-axis direction in the coordinate system shown in these drawings. As will be described in detail later, the optical elements 22 included in a single optical element array 20 have three or more azimuths within the XY plane. To determine the azimuth of an optical element 22 within the XY plane, it is convenient to define an "azimuth angle". In this description, the angle formed between the azimuth of a normal (indicated by the dashed line) to the first surface 24 or the second surface 26 of the optical element 22 and the Y-axis when the optical element 22 is viewed perpendicularly to the image capturing plane 10 is defined herein to be the "azimuth angle of the optical element". In FIG. 20B, the azimuth angle of the optical element is 90 degrees.

According to the present disclosure, the optical elements 22 are arranged so as to have at least three different azimuth angles. In this manner, light rays, of which the polarization directions are at least three different directions, can be incident on respective photodiodes 12. As a result, image with mutually different polarization directions can be obtained either in each pixel or on the basis of multiple pixels. Such a polarization image sensor can be used effectively in an image capture device such as an endoscope.

The optical element array has a structure in which a plurality of optical units, each being comprised of X optical elements (where X is an integer that is equal to or greater than three), are arranged two-dimensionally. In each optical unit, those X optical elements are arranged so that a normal to the first or second surface of each optical element has at least three different azimuth angles.

Hereinafter, an embodiment of a polarization image sensor according to the present disclosure will be described in further detail with reference to the accompanying drawings.

(Embodiment 3)

Figure 21:
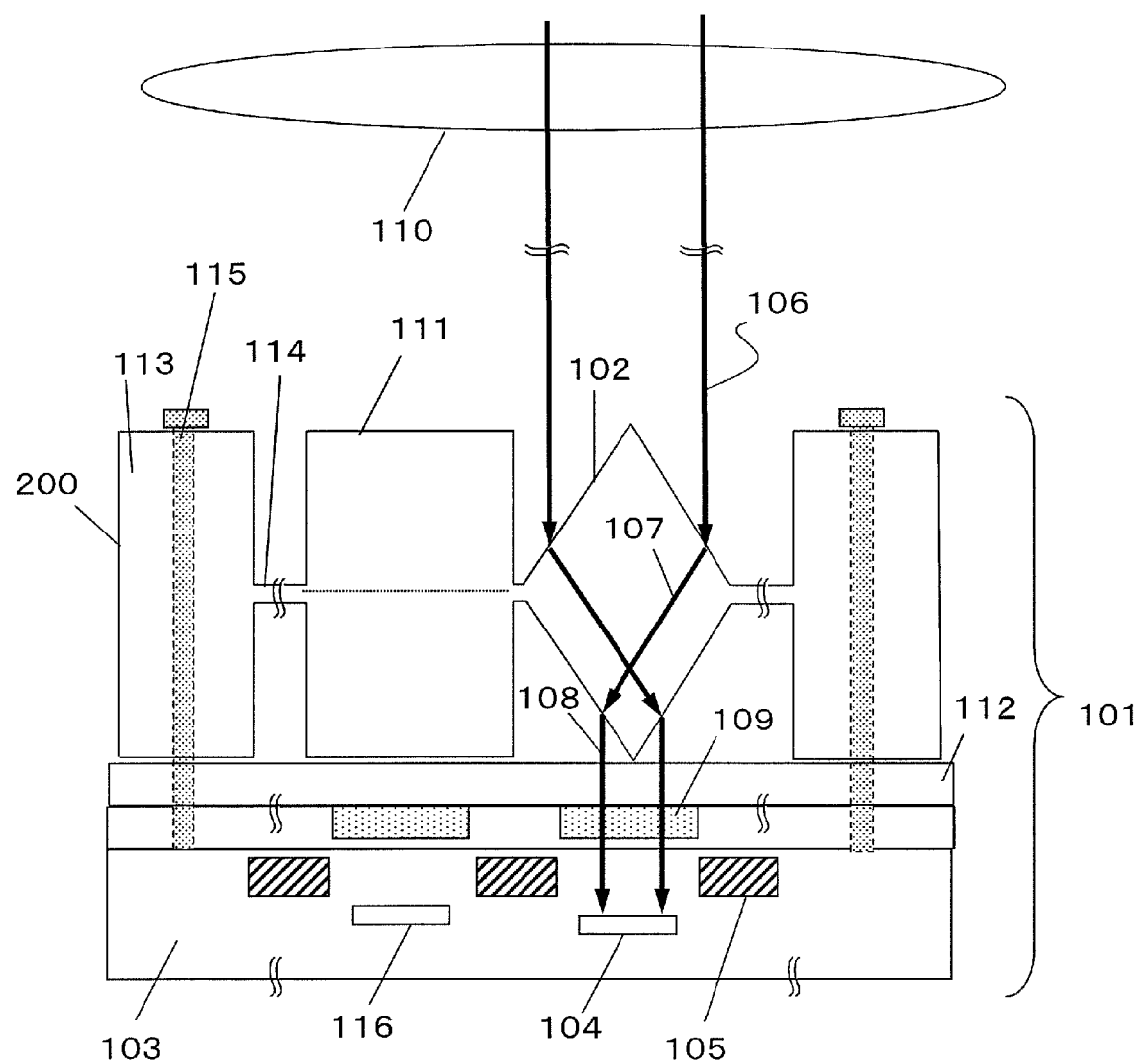
FIG. 21 shows a cross-sectional view illustrating a polarization image sensor according to the third embodiment of the present disclosure.

FIG. 21 is a cross-sectional view illustrating a configuration for a part of a polarization image sensor as a third embodiment of the present disclosure. The polarization image sensor 101 according to this embodiment includes a sensor substrate 103 in which photodiodes 104 and 116 functioning as photosensitive elements are arranged two-dimensionally on the image capturing plane 10 and an optical element array 200 which is supported on the sensor substrate 103.

On the sensor substrate 103, arranged are an opaque film 105, color filters 109 and a quartz LPF (low-pass filter) 112. As will be described later, the color filters 109 and the quartz LPF 112 are used in a synchronous type illumination but are not used in a sequential type illumination.

The optical element array 200 is made up of a plurality of optical elements including optical elements 102 and 111 with multiple different azimuth angles. Each of these optical elements has the configuration shown in FIGS. 20A, 20B and 20C and functions as a polarizer. Such an optical element that increases the degree of polarization through refraction will be referred to herein as a "prism optical element". Each of these prism optical elements 102 and 111 is arranged so as to cover one or multiple photodiodes 104, 116. Each incoming light ray 106 that has been transmitted through an objective lens 110 gets refracted by the slope (i.e., the first surface) of the prism optical element 102 and enters the prism optical element 102 to turn into a refracted light ray 107, which gets refracted by another surface (i.e., the second surface) of the prism optical element 102 to be an outgoing light ray 108. The outgoing light ray 108 is transmitted through the quartz LPF 112 and color filter 109 to reach the photodiode 104.

Over the photodiode 116 which is adjacent to the photodiode 104, arranged is another prism optical element 111. These two prism optical elements 102 and 111 are arranged so as to face mutually different directions around the axis of the incoming light ray 106. FIG. 21 illustrates how the prism optical elements 102 and 111 are arranged so as to face two directions that are different from each other by 90 degrees. On the sensor substrate 103 of the polarization image sensor 101, a lot more photodiodes are actually arranged on the image capturing plane 10.

Adjacent prism optical elements including the prism optical elements 102 and 111 are connected together with flat plate portion 114, thereby forming a single optical element array 200. The entire optical element array 200 is secured to the sensor substrate 103 with a supporting member 113. In the example illustrated in FIG. 21, the supporting member 113 and the sensor substrate 103 are connected together with fixing screws 115. Optionally, the supporting member 113 may form an integral part of the optical element array 200. For example, the optical element array 200 may be made by cutting a transparent substrate with a certain thickness. Alternatively, the optical element array 200 and the sensor substrate 103 may be fixed together with any other fixing member or an adhesive instead of using the fixing screws 115.

Figure 22:
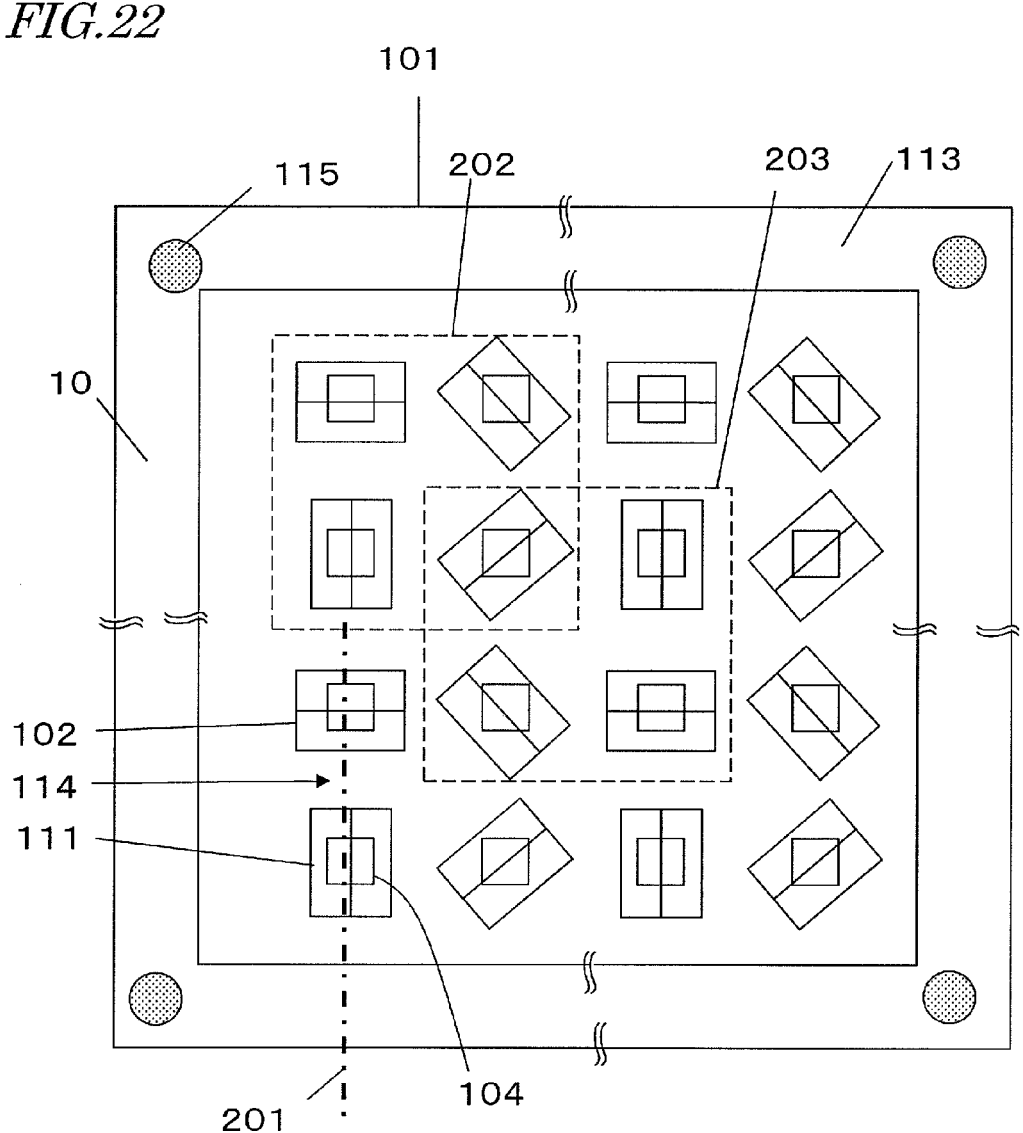
FIG. 22 shows a plan view illustrating a polarization image sensor according to the first embodiment of the present disclosure as viewed from over the objective lens.

FIG. 22 is a plan view illustrating the polarization image sensor 101 as viewed from the light source. A cross section as viewed on the plane indicated by the one-dot chain 201 shown in FIG. 22 is illustrated in FIG. 21. In FIG. 22, the fixing screws 115 are located around the four corners of the polarization image sensor 101. In the example illustrated in FIG. 22, the rectangular area surrounded with the supporting member 113 is the image capturing plane. Even though 16 photodiodes for 16 pixels are arranged in four columns and four rows on this image capturing plane for the sake of simplicity, actually a lot more photodiodes are arranged there. For example, the photodiodes may be arranged to form more than one million pixels. In this description, a single pixel will be sometimes referred to herein as a "single cell". In this embodiment, one prism optical element is allocated to each photodiode and the light that has been transmitted through each prism optical element is incident on its associated photodiode.

The prism optical elements that cover respective photodiodes are arranged so as to have four different azimuth angles, and the optical elements allocated to each pair of adjacent pixels have azimuth angles that are different from each other by 45 degrees. According to such an arrangement, any set of 2×2 cells selected from this plane is always covered with prism optical elements with four different azimuths. Specifically, on this image capturing plane 10, each of the units 202 and 203 indicated by the dashed squares in FIG. 22 includes four photodiodes that are arranged in two columns and two rows and is covered with four prism optical elements that are also arranged in two columns and two rows. In this description, such photodiodes (pixels) that are arranged in two columns and two rows will be referred to herein as "2×2 cells". On each of these units 202 and 203, four different kinds of light rays with mutually different polarization directions are incident. By performing processing using the 2×2 cells are a unit, the plane of vibration of the polarized light can be estimated.

Figure 23:
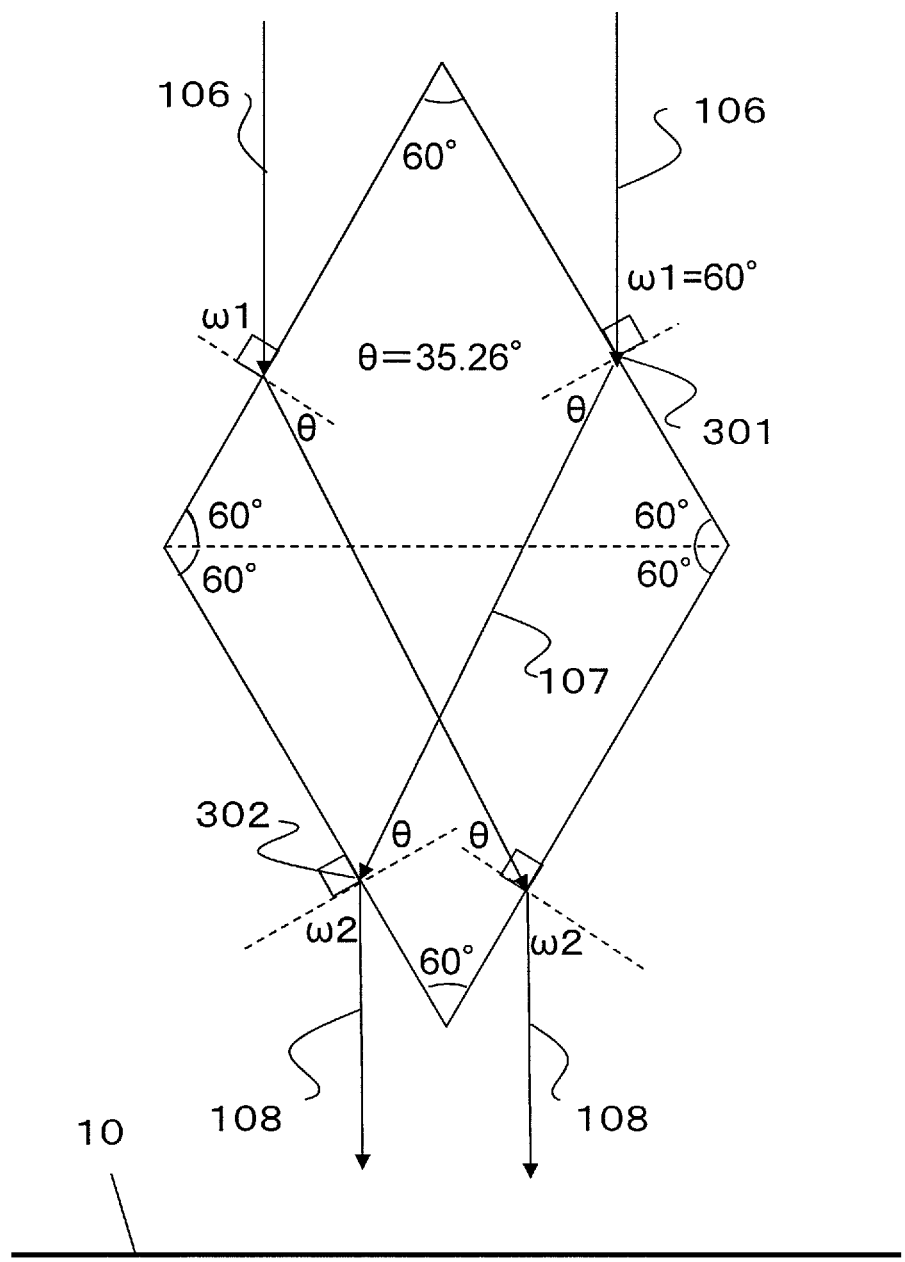
FIG. 23 shows exactly how the path of a light ray changes according to the shape of a single prism optical element.

FIG. 23 illustrates the shape of a single prism optical element and the paths of light rays being transmitted through it. A prism optical element generally has an isosceles triangular cross section. On the other hand, a prism optical element for use in this embodiment has a shape in which two prisms with an equilateral triangular cross section are bonded together on their bottom. More specifically, a prism optical element according to this embodiment has a structure in which two prisms with an equilateral triangular cross section are combined together, and those two prisms are made of the same material and are continuous with each other with no other material interposed between them.

Every vertex of this equilateral triangular cross section has an angle of 60 degrees. If an incoming light ray that has come from right over the optical element perpendicularly to the image capturing plane 10 reaches a point of incidence 301, the angle of incidence $\omega 1$ at the slope (first surface) of the prism optical element becomes 60 degrees. If this prism optical element is made of an acrylic plate or quartz glass, for example, then its refractive index will be approximately 1.5. As a result, the angle of emittance $\theta$ when the incoming light ray 106 enters the prism optical element from the air becomes approximately 35.26 degrees. And this refracted light ray 107 becomes a light ray 108 that goes out of this prism optical element into the air through a point of emittance 302 at an angle $\omega 2$ $(=\omega 1)$. These two light rays 106 and 108 are parallel to each other. This prism optical element does not change the traveling direction of the incoming light but does change its polarization state.

Figure 24:
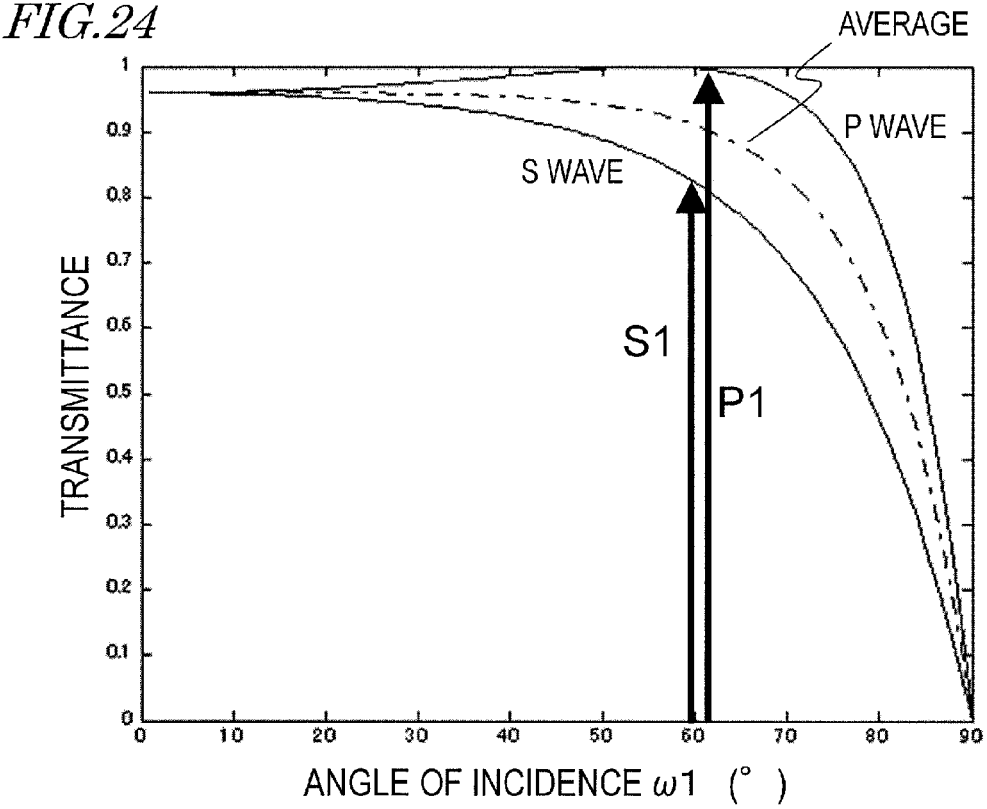
FIG. 24 shows a graph showing relations between the angle of incidence and the transmittance of light (at the time of incidence).
Figure 25:
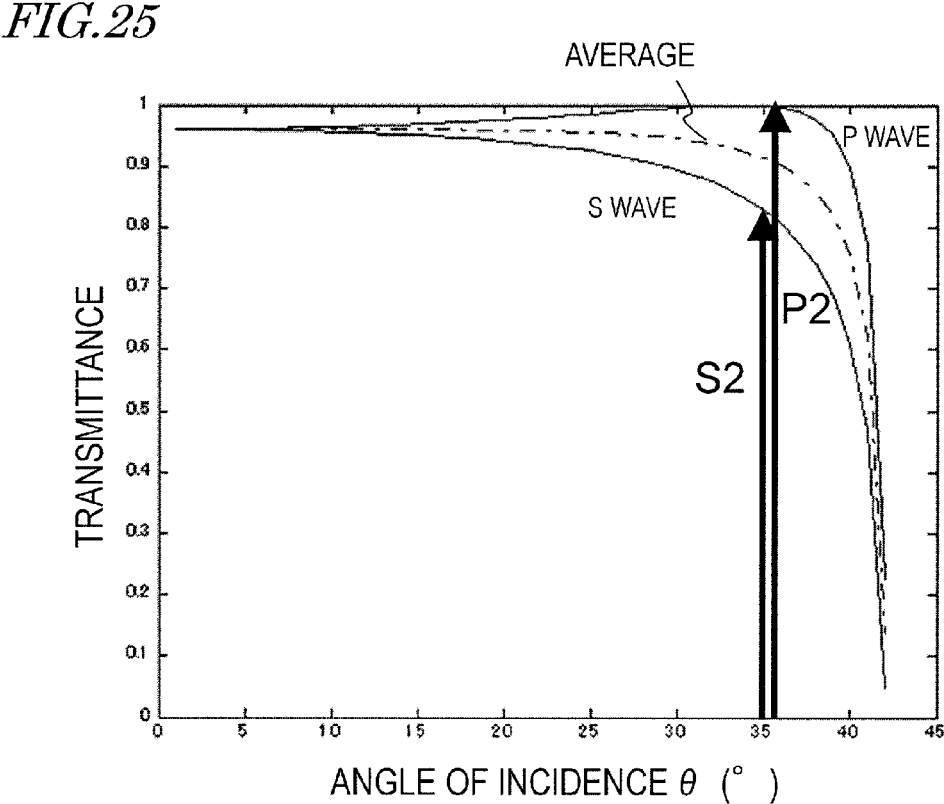
FIG. 25 shows a graph showing relations between the angle of incidence and the transmittance of light (at the time of emittance).
Figure 26:
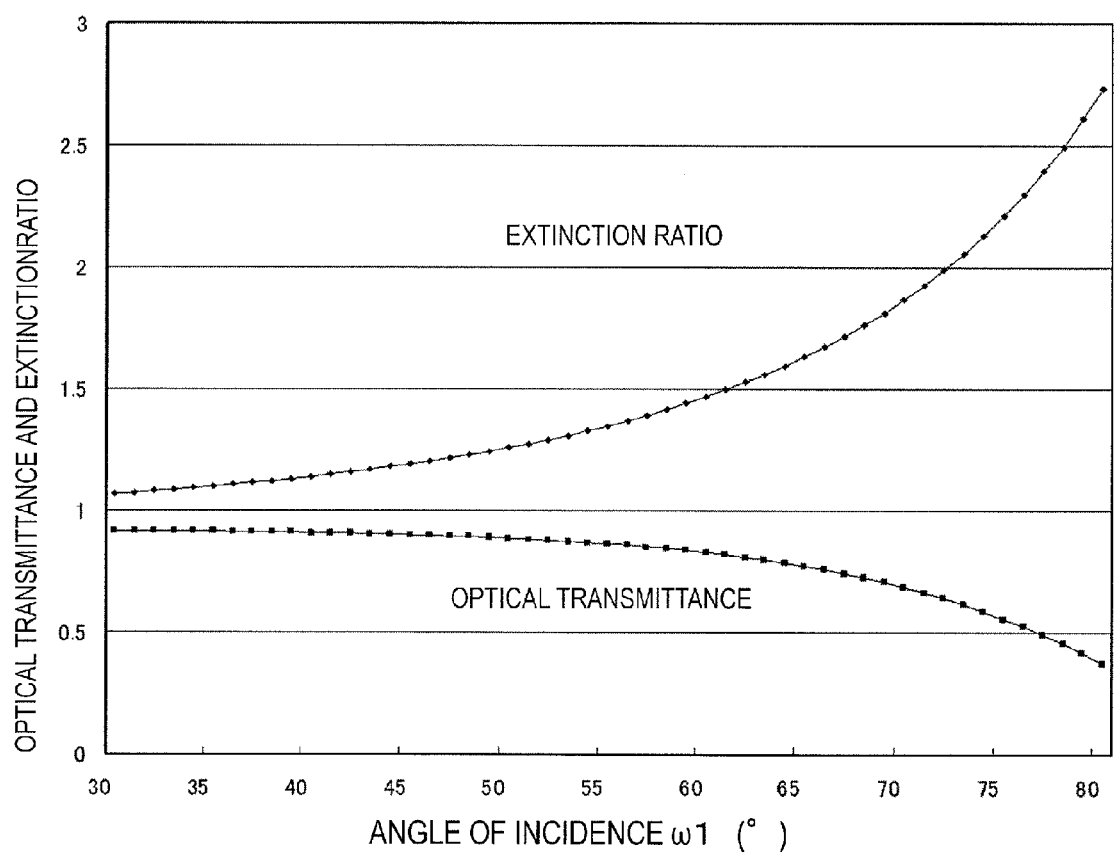
FIG. 26 shows a graph showing the relation between the angle of incidence, the transmittance of light, and the polarized light selectivity from the time of incidence through the time of emittance combined.

FIGS. 24, 25 and 26 are graphs showing how the polarization state changes. In FIG. 24, the abscissa represents the angle of incidence $\omega 1$ and the ordinate represents the transmittance of light. And FIG. 24 shows how the polarization state changes when the light that has traveled through the air is incident on the prism optical element. In the prism optical element shown in FIG. 23, the surface on which the incoming light is incident (i.e., the first surface) is made up of two slopes that tilt toward two opposite directions, and those two slopes define an angle of 60 degrees between them. Thus, the angle of incidence $\omega 1$ is fixed at 60 degrees. But if the cross-sectional shape of the prism optical element is changed, then the angle of incidence ω1 will also change.

If the transmittances of P and S waves are calculated with respect to the cross section of the prism by substituting a refractive index of 1.5 into the Fresnel's reflection and refraction theoretical formula, the two P- and S-wave curves shown in FIG. 24 can be obtained as a function of the angle of incidence w1. If non-polarized light is incident on the prism optical element, an outgoing light ray in which the P and S waves are mixed together will be obtained. The transmittance of such an outgoing light ray is represented by the one-dot chain curve that says "average" in FIG. 24. As shown in FIG. 23, if the angle of incidence ω1=60 degrees, the P-wave transmittance is P1 (=approximately 99%) and the S-wave transmittance is S1 (=approximately 80%). The transmittance of non-polarized light is equal to the transmittance of light in which P and S waves are included evenly. That is why if non-polarized light is incident on the slope of the prism optical element at an angle of incidence of 60 degrees, approximately 90% of the incident light enters the prism optical element. At this point in time, the P-wave component included in the incident light prevails over the S-wave component. In other words, when transmitted through the first surface of the prism optical element, the P-wave component of the light dominates the S-wave component, thus increasing the degree of polarization.

FIG. 25 shows how the light ray that has entered the prism optical element has its polarization state changed when going out of the prism optical element into the air. Specifically, the transmittance of a light ray that was going out of a prism optical element with a refractive index of 1.5 through its second surface into the air was calculated based on the Fresnel's reflection and refraction theory. FIG. 25 shows the P wave, S wave and average curves obtained by making this calculation. In FIG. 25, the angle of incidence θ is shown only up to the vicinity of 45 degrees. This is because if the angle of incidence were greater than about 45 degrees, the incoming light ray would be totally reflected and there would be no outgoing light ray at all. If the angle of incidence θ from inside of the prism optical element into the air is supposed to be 35.26 degrees, the transmittance of the P wave is P2 (=approximately 100%) and the transmittance of the S wave is S2 (=approximately 80%). If a perfectly non-polarized light ray is incident from inside of the prism optical element onto the second surface, then approximately 90% of the non-polarized light will go out of the prism optical element into the air. In that case, more P waves will go out than S waves.

FIG. 26 is a graph showing how the polarized light selectivity and optical transmittance change with the angle of incidence ω1. In this case, the extinction ratio y and optical transmittance were calculated both when the light ray was incident on the prism optical element and when the light ray left the prism optical element.

The extinction ratio increases as the angle of incidence ω1 increases. On the other hand, the optical transmittance decreases as the angle of incidence ω1 increases. That is why when this polarization image sensor is designed, an angle of incidence ω1 at which a target extinction ratio and a target optical transmittance are both achieved may be selected. Such an angle of incidence ω1 falls within the range of 55 to 80 degrees. For example, if the angle of incidence ω1 is set to be around 60 degrees, a polarized light selectivity of approximately 1.5 and an optical transmittance of approximately 0.8 (=80%) are achieved. This performance is as high as when a parallel light ray is incident on the equilateral triangular prism shown in FIG. 23. It should be noted that the "extinction ratio" refers herein to the ratio Q of the maximum intensity MAX of a P wave to the minimum intensity MIN of an S wave (i.e., Q=(MAX/MIN)). Optionally, the polarized light selectivity may also be represented by the degree of polarization DP as in the following Equation (1):

$$DP=(MAX-MIN)/(MAX-MIN) \quad (1)$$

According to this Equation (1), when the polarized light selectivity Q=1.5, a degree of polarization DP=20% is obtained. If the angle formed between the axis of polarization of an incoming linearly polarized light ray and the polarized light transmission axis of a normal polarizer is changed by 180 degrees, then the intensity of the light ray transmitted through the polarizer will change as a sine wave. In that case, if the maximum value MAX and minimum value MIN of the light being transmitted through the polarizer is obtained by measurement, the DP value can be obtained by Equation (1). Since the minimum value MIN is approximately equal to zero in a normal polarizer, DP=1 can be obtained. Compared to the DP of such a polarizer, the degree of polarization DP of a prism optical element is much smaller. Still, considering the performance of the image sensor, its variation is a sufficiently sensible one.

Figure 27A:
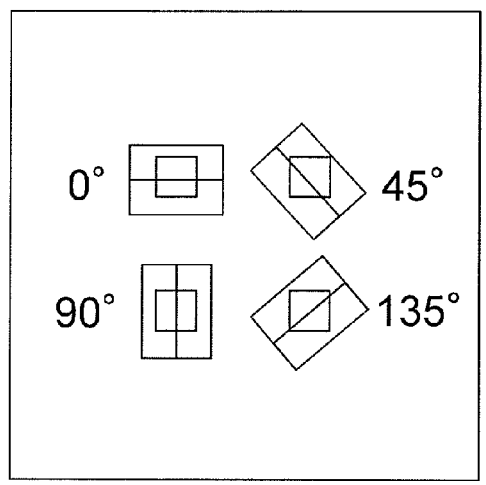
FIG. 27A shows a plan view schematically illustrating 2×2 cells including prism optical elements which are arranged to have four different azimuth angles so that their azimuth angles are different from each other by 45 degrees between each pair of adjacent pixels.
Figure 27B:
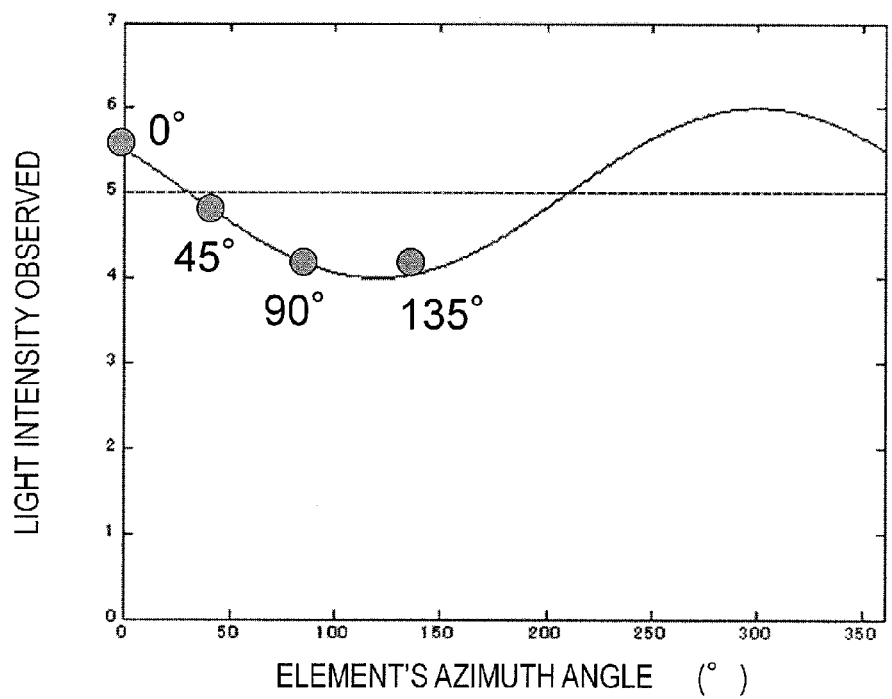
FIG. 27B shows a graph showing an exemplary relation between the light intensity at each cell shown in FIG. 27A and the polarization direction of an incoming linearly polarized light ray (i.e., the azimuth angle defined by the principal axis of the polarized light on the image capturing plane).

FIG. 27A is a plan view schematically illustrating 2×2 cells with four prism optical elements which are arranged so that their azimuth angles are different from each other by 45 degrees between each pair of adjacent pixels. FIG. 27B is a graph showing an exemplary relation between the intensities of the respective cells shown in FIG. 27A and the polarization direction of an incoming linearly polarized light ray (i.e., the azimuth angle defined by the principal axis of polarized light at the image capturing plane). If the incoming light ray is polarized, the intensities obtained at the respective photodiodes corresponding to four pixels are different from each other. By plotting those intensities on the input axis every 45 degrees, fitting can be carried out in the following manner using a sine function including an amplitude A, a phase angle B and an average value C that are all unknown numbers. The method of such optimum fitting is disclosed in. Japanese Patent Publication No. 4235252, for example.

$$I(\psi)=A \cdot \sin 2(\psi-B)+C \quad (2)$$

Based on the three unknown numbers that have been obtained through this fitting, polarization information about these 2×2 cells is obtained in the following manner.

The principal axis of the polarized light corresponds to an azimuth angle at which the intensity becomes the lowest, and therefore, is calculated by the following Equation (3):

$$PPH = \psi_{min} = B + \frac{3\pi}{4} \quad (3)$$

The degree of polarization is calculated by the following Equation (4):

$$DP = \frac{I_{max} - I_{min}}{I_{max} + I_{min}} = \frac{A}{C} \quad (4)$$

An image to be produced based on the two parameters that have been calculated in this manner, namely, the principal axis of the polarized light and the degree of polarization, will be referred to herein as a "polarization image".

Hereinafter, it will be described how to get color information when a polarization image is being captured. There are some conventional techniques for obtaining a polarization image and a normal color image at the same time in a particular wavelength range. For example, Japanese Laid-Open Patent Publication No. 2010-130655 discloses an image sensor which can obtain a color image in the visible radiation range and polarization information in the infrared range at a time. Meanwhile, techniques for obtaining color images in RGB bands and a polarization image in a B band at the same time and in real time within the visible radiation range are disclosed in Japanese Laid-Open Patent Publication No. 2009-240676, Japanese Laid-Open Patent Publication No. 2009-246770, and Japanese Laid-Open Patent Publication No. 2009-246840. According to these conventional techniques, however, a polarization filter is provided for B pixels, which have already been darkened by B (blue) filters, in order to get color information and polarization information at the same time, and therefore, the quantity of light lost is significant as mentioned above. Also, in that case, the only polarization image obtained is a B (blue) image, and no polarization images can be obtained for R and G at all.

In contrast, according to an embodiment of the present disclosure, full-color images in the RGB bands and polarization images in the RGB bands can be obtained at the same time and in real time with a sufficient quantity of light maintained. According to an embodiment of the present disclosure, the images thus obtained are much brighter than what is obtained by such a conventional polarization image sensor, with which the quantity of the light would be lost by as much as 50%, and the color information can be obtained in practice.

Figure 28:
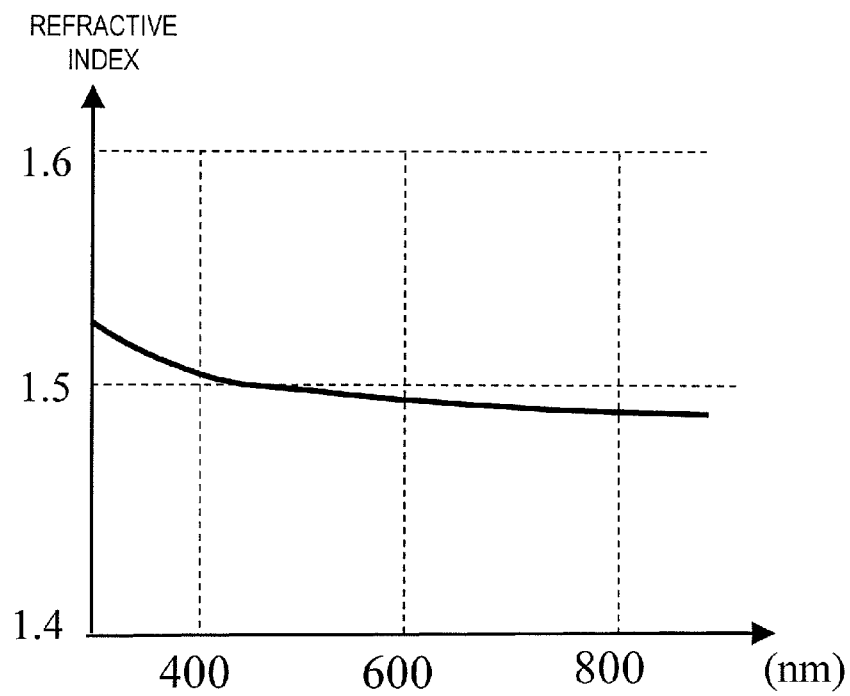
FIG. 28 shows a graph showing the wavelength dependence of the refractive index in a situation where the material is quartz glass, for example.

FIG. 28 shows the wavelength dependence of the refractive index of quartz glass. According to the present disclosure, the material of the optical elements is not particularly limited but may be any optically transparent material with a refractive index of approximately 1.4 to 1.8. As shown in FIG. 28, if the wavelength changes from a short one into a long one within the visible radiation range, the refractive index decreases to a certain degree. However, the change is not a significant one, but the refractive index n changes just slightly from about 1.52 to about 1.48 in the visible radiation range of 400 nm to 800 nm. Thus, if the prism optical elements are made of quartz glass, then the refractive index n of the optical elements will vary within the range of approximately 1.52 to 1.48 according to the wavelength of the incoming light ray. Next, it will be considered how much such a difference in refractive index affects the transmittance and the extinction ratio.

Figure 29:
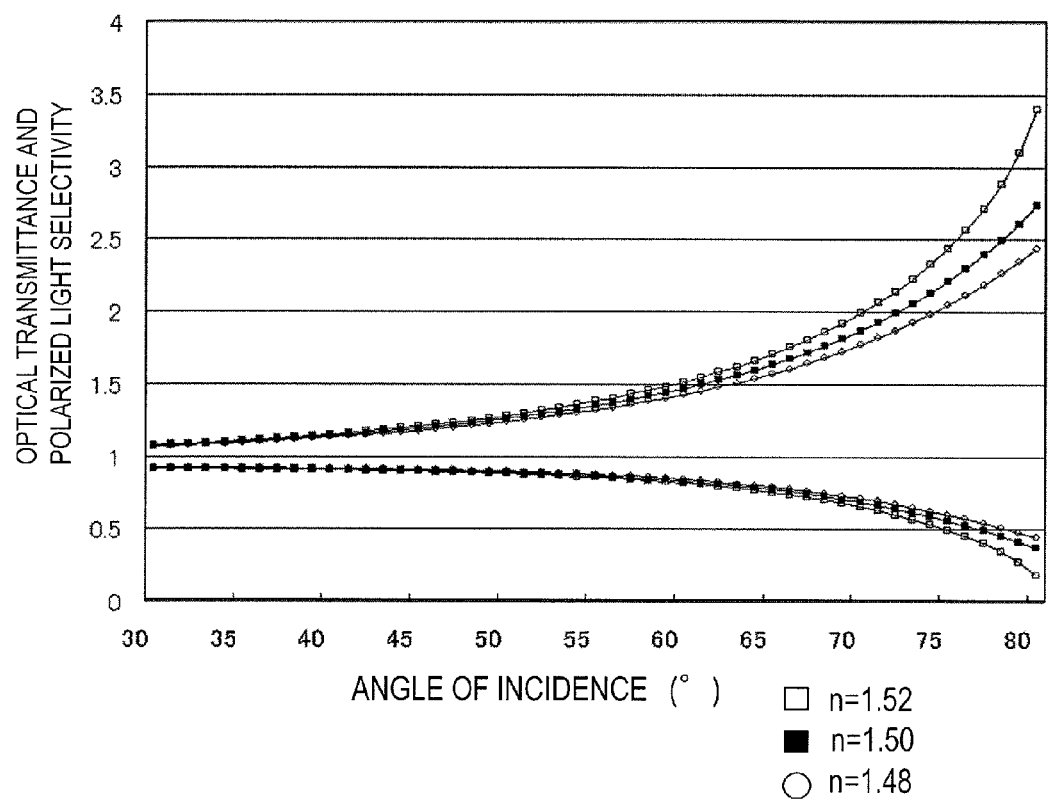
FIG. 29 shows a graph showing the integrated polarized light selectivities and optical transmittances from the time of incidence through the time of emittance in a situation where the refractive index is supposed to vary with the wavelength.

FIG. 29 is a graph showing how the extinction ratio and optical transmittance change with such a variation in refractive index taken into account. In this case, the extinction ratio and optical transmittance were calculated with their values, which varied since the light ray entered the prism optical element and until the light ray left the prism optical element, integrated together. In FIG. 29, shown are three curves associated with refractive indices n of 1.48, 1.50 and 1.52, which correspond to the color red, green and blue wavelengths, respectively, as shown in FIG. 28. When the refractive index increases from 1.48 to 1.52 (i.e., when the incoming light ray changes its colors from red into blue) at an angle of incidence of around 60 degrees, the polarized light selectivity does increase by about 1.43 to about 1.52. Also, when the refractive index increases from 1.48 to 1.52 at an angle of incidence of around 60 degrees, the optical transmittance does decrease by about 0.84 to about 0.81.

These facts reveal that the polarization image sensor of this embodiment has almost no wavelength dependence when getting color information within the visible radiation range. That is why the polarization image sensor of this embodiment not only will hardly lose the quantity of light but also can get color information easily as well. As can be seen, since the physical phenomenon used is only the refraction of light by a dielectric member and since the refractive index has little wavelength dependence, no special consideration is needed as to capturing an image in a broad range (i.e., in the entire visible radiation range), or getting color information. That is why an endoscope of the frame sequential type, in particular, can not only obtain a color image using this image sensor as it is but also obtain color-by-color polarization images (i.e., for each of RGB components), which has never been realized by anybody in the related art. To achieve the effects of the present disclosure, prism optical elements of a larger size than the pixels may also be used. It should be noted that as a polarization image sensor that uses a photonic crystal operates with polarized light only in a narrow wavelength range, the constant needs to be changed for each of RGB in order to realize a color representation. Also, to make a polarization image sensor of a wire grid type operate in the visible radiation range, a nanostructure with a wavelength of a few hundred nanometers or less needs to be made. Compared to such structures, the polarization image sensor of this embodiment can be made relatively easily.

If a light ray is supposed to be incident perpendicularly onto the image sensor at an angle of incidence $\omega 1$ of 55 to 80 degrees, then the optical transmittance will be 50% or more. As a result, polarization image sensor that can get a brighter image with a much less quantity of light lost than a conventional polarization image sensor is realized. Optionally, in order to maintain this angle of incidence $\omega 1$, a so-called "telecentric optical system" in which the incoming light ray is nearly a parallel light ray may be used, or the prism optical element of this embodiment may be arranged only in the vicinity of the center of the image sensor, or any other appropriate measure may be taken.

Now it will be described what the "full-color image" and "color polarization image" mean in this description. In the following description, an image sensor according to the present disclosure is supposed to obtain both a "full-color image" and a "color polarization image". In this case, the "full-color image" refers herein to a color image, of which the light intensity is high enough to use it in a conventional endoscope, but such full-color images may be classified into the following two types according to the method of generating such a full-color image. One of the two types is a "polarized light average full-color image", in which even if the light intensities supplied from the prism optical elements with four polarization directions are different from each other, their average value is used as the light intensity value. That is why even if an image is generated based on color rays that have been polarized by the internal body tissue, the colors can be reproduced just as intended but the resolution decreases somewhat due to the averaging. The other type is a "supposedly non-polarized light full-color image", in which the incoming light ray is supposed to be non-polarized. In that case, since the light intensities supplied from the prism optical elements with four different polarization directions are supposed to be no different from each other, a full-color image can be obtained at a resolution exactly as defined by the number of pixels. Even if the image sensor is combined with a color mosaic filter, a full-color image can also be obtained by performing the conventional mosaic interpolation processing, and therefore, the resolution does not decrease. Nevertheless, if the image received has been generated based on polarized light, the light intensities will vary in those four directions, and therefore, the colors cannot be reproduced as intended.

The "polarization average full color image" and "supposedly non-polarized full color image" are generated due to a difference in the method of processing an image signal supplied from the image sensor and have nothing to do with the configuration of the image sensor itself.

Next, the "color polarization image" refers herein to a polarization image to be observed in each of the RGB color bands falling within the visible radiation range. With the color polarization image, an analysis can be made to see how the polarization state changes in each color band, i.e., on a wavelength range basis. It should be noted that such color-by-color polarization information falling within the visible radiation range is regarded as important data particularly in the field of medicine.

Figure 30:
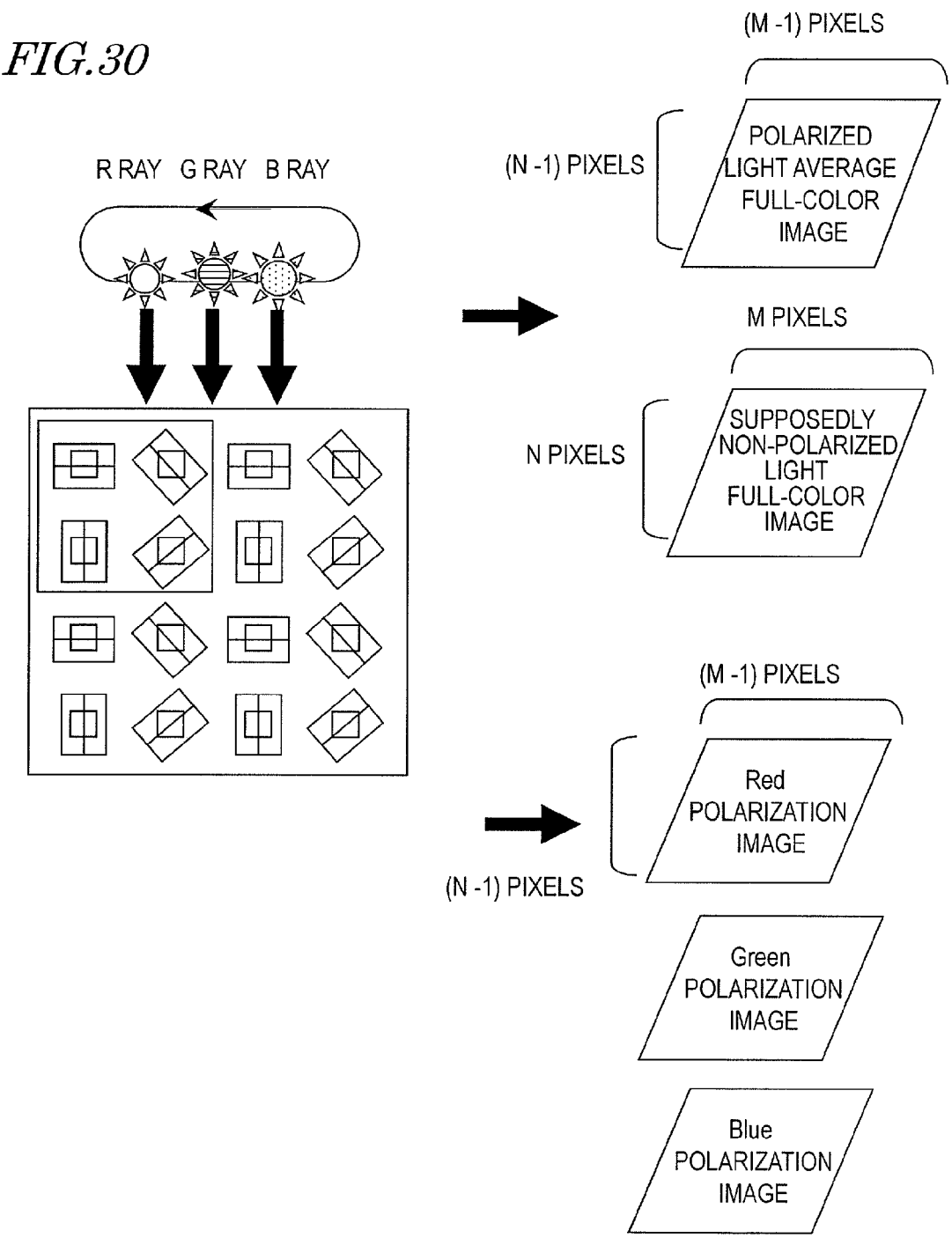
FIG. 30 illustrates how the "frame sequential" endoscope obtains color information according to the first embodiment of the present disclosure.

FIG. 30 illustrates a situation where color information is obtained by using a polarization image sensor according to the present disclosure for an endoscope of a so-called "frame sequential type". The endoscope of the frame sequential type refers herein to an endoscope which sequentially captures high-definition monochrome images as the colors of the illuminating light change in the order of R, G and B and which generates a full-color moving picture by synthesizing those monochrome images together. That is why every time the color of the illuminating light changes sequentially in the order of R, G and B, a polarization image can be obtained naturally on an RGB band basis. And by carrying out the processing of obtaining the principal axis of polarized light and the degree of polarization described above on each of those polarization images, polarization information can be obtained on a color by color basis. If the number of pixels corresponding to the number of photodiodes is M×N pixels and if the 2×2 cells are processed with the target shifted by one pixel each time, then the resolution of each of the RGB polarization images becomes (M−1)×(N−1) pixels. Consequently, the resolution hardly decreases.

Figure 31:
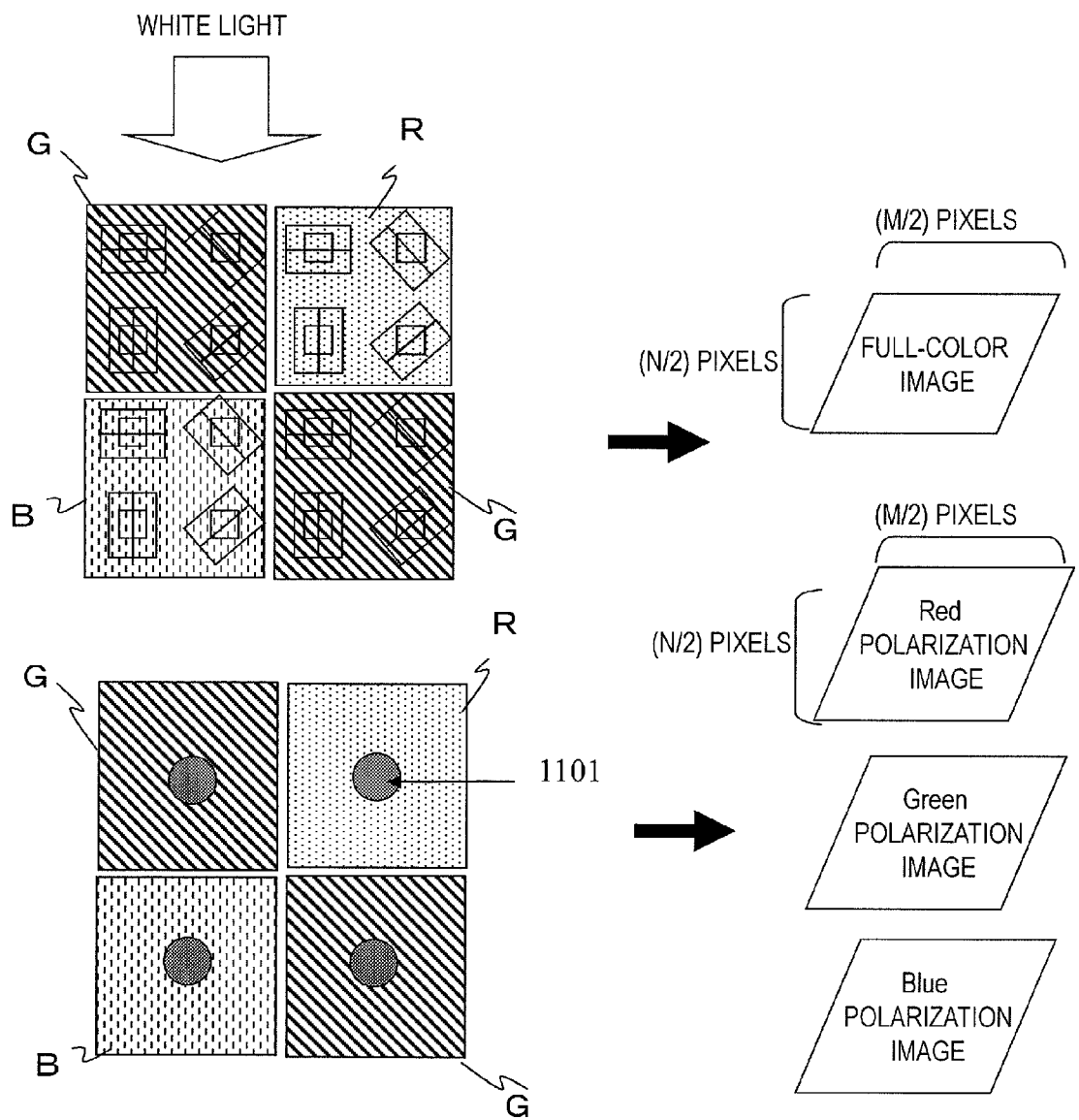
FIG. 31 illustrates how the "synchronous" endoscope may obtain color information according to the first embodiment of the present disclosure.
Figure 32:
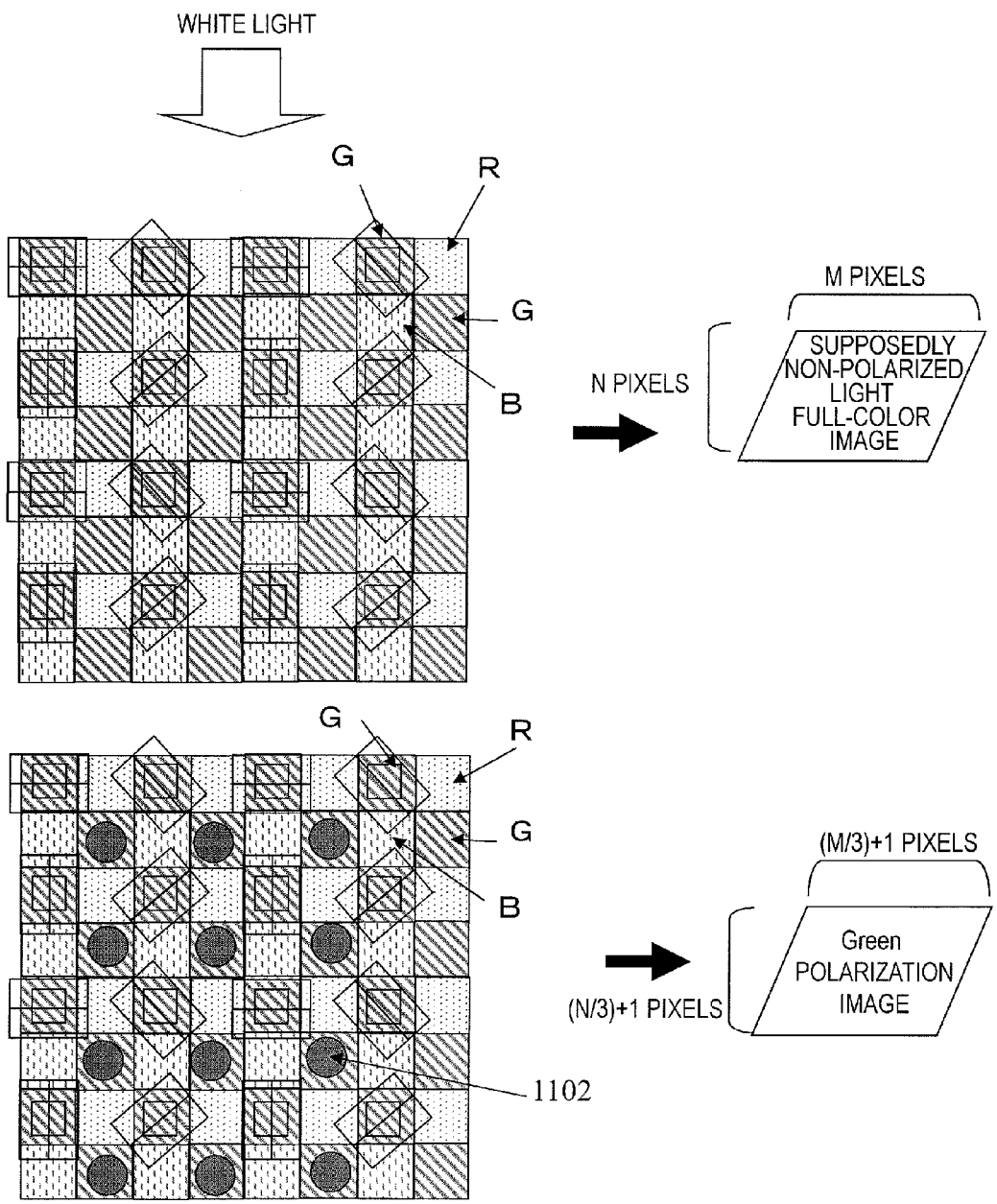
FIG. 32 illustrates how the "synchronous" endoscope may obtain a different piece of color information according to the first embodiment of the present disclosure.

FIGS. 31 and 32 show how a so-called "synchronous" endoscope carries out a color representation using the polarization image sensor of the present disclosure.

The synchronous endoscope is configured to generate a full-color image by arranging a color mosaic filter closer to the image sensor to filter white illuminating light as shown in FIGS. 31 and 32. This color mosaic filter may be allocated in one of two different ways. Specifically, FIG. 31 shows a method in which one of RGB filters in a Bayer arrangement mosaic is allocated to each set of four prism optical elements as disclosed in Japanese Patent Publication No. 4235252. As a result, as polarization images are captured in four different directions as for a single color, polarization information for that color is fixed. Nevertheless, as the color polarization images captured form a color mosaic image, that image needs to be subjected to mosaic interpolation to obtain a full-color image. As a result, a polarization image can be obtained in each of the RGB bands as in the frame sequential method. Each of the points 1101 shown in FIG. 31 indicates the pixel center of its associated polarization image. As can be seen, in the exemplary configuration shown in FIG. 31, a plurality of photodiodes that are arranged on the image capturing plane includes a plurality of photosensitive units, each of which is made up of Y photodiodes (where Y is an integer that is equal to or greater than three). In the example illustrated in FIG. 31, Y=4. Also, in the example illustrated in FIG. 31, a color mosaic filter is provided to make a single color ray (i.e., an R, G or B ray) incident on the Y photodiodes included in each photosensitive unit.

This mosaic interpolation processing is slightly different from the ordinary color light intensity interpolation. Specifically, this mosaic interpolation processing is carried out with the principal axis of polarized light and degree of polarization, which are the two different kinds of polarization information, regarded as light intensity values. Particularly, as the principal axis of polarized light is an angular value with a period of 180 degrees, an excess over 180 degrees during the interpolation calculation is corrected.

By performing this processing, both a full-color image and color polarization images which have been generated based on non-polarized returning light come to have a resolution of (M/2)×(N/2) pixels, which are one half as large as their original number of pixels M×N both vertically and horizontally alike. According to this method, a polarization image can be obtained for each of RGB components, which is beneficial.

FIG. 32 illustrates a method for allocating a set of four prism optical elements to four pixels in the same color at the four corners of each 3×3 unit area of a Bayer mosaic filter. According to this method, the resolution of a supposedly non-polarized light full-color image remains M×N pixels that the image sensor has (i.e., the resolution does not decrease), which is beneficial. Also, as for a polarization image, only pixels in the same color are used to perform polarization processing, and therefore, only G pixels can be used as shown in FIG. 32. That is why the pixel center of each polarization image becomes the center pixel of each set of 3×3 pixels of a Bayer mosaic as indicated by the point 1102. Consequently, according to this configuration, a polarization image cannot be obtained for every color of RGB. In the example illustrated in FIG. 32, a polarization image consisting of only G (green) pixels is generated but its resolution becomes ((M/3)+1)×((N/3)+1) pixels. That is to say, the decrease in resolution is relatively small. In addition, as polarized light observing pixels are separated from each other by two pixels according to this configuration, only a half of the maximum resolution may remain as the spatial frequency of the image. Consequently, a quartz LPF for use in a Bayer mosaic filter can be used, which is advantageous. In that case, since the quartz LPF destroys the polarization state due to birefringence, the quartz LPF 112 is arranged between the prism optical element and the color filter as shown in FIG. 21. Even though the polarized light observing pixels are supposed to be G pixels in the example illustrated in FIG. 32, the polarized light observing pixels may also be R pixels or B pixels, too. Also, although 3×3 pixels are supposed to be allocated to each set of four optical elements in the example illustrated in FIG. 32, any other number of pixels, e.g., 5×5 pixels, may also be allocated to it instead.

Figure 33:
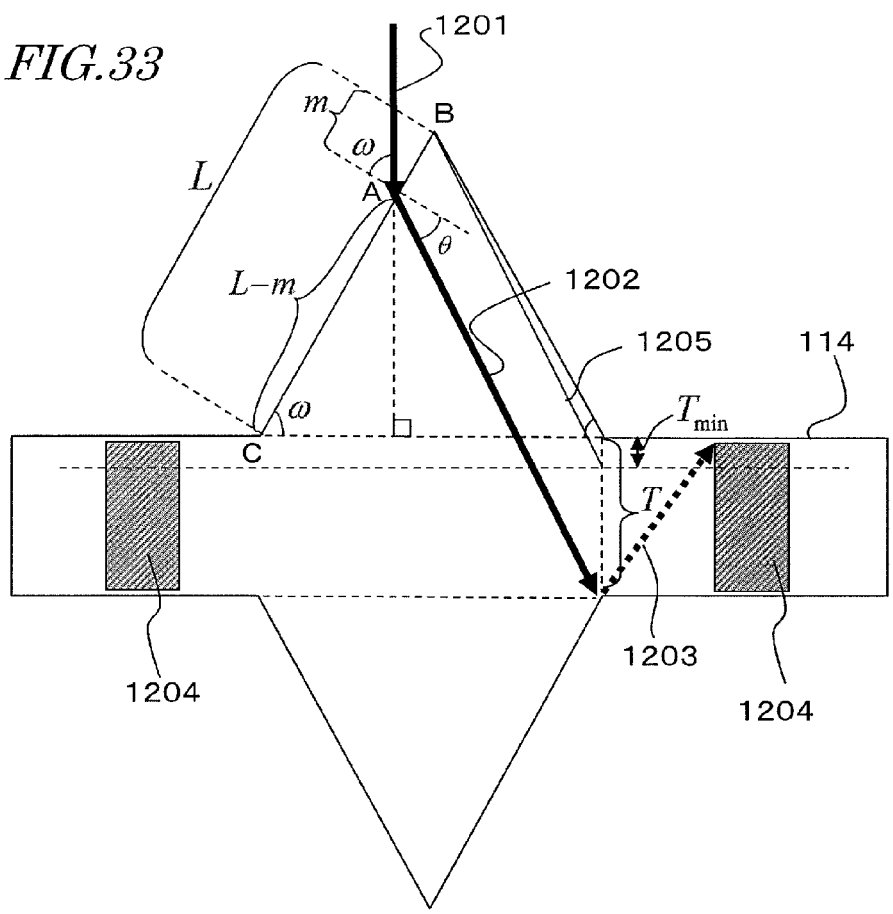
FIG. 33 shows a condition on the thickness of a flat plate portion which connects prism optical elements together.

FIG. 33 shows a condition on the thickness of the flat plate portion 114 that connects prism optical elements together. To pass the incoming light non-wastefully, the thickness T of the flat plate portion is ideally set to be zero. However, if the thickness T of the flat plate portion 114 were too small, then it would be difficult for the flat plate portion 114 to support the optical elements. On the other hand, if the thickness T of the flat plate portion 114 were too large, then the incoming light 1201 would turn into a refracted light ray 1202 which would travel through the optical element and be eventually reflected from the flat plate portion 114. The light ray 1203 that has been reflected from the flat plate portion 114 might enter other pixels. To avoid such a situation, an opaque portion 1204 may be provided between each pair of optical elements. By providing such an opaque portion 1204, the thickness T of the flat plate portion 114 can be set to be sufficiently large and the mechanical strength of the optical element array can be increased to a sufficiently high level. On the other hand, if the thickness T of the flat plate portion 114 is set to be equal to or smaller than a certain value, it is possible to prevent the light ray from entering other pixels even without providing the opaque portions 1204. Hereinafter, this point will be described.

In this example, the prism optical element is supposed to have an isosceles triangular cross section having a slope with a length L as shown in FIG. 33. Suppose an incoming light ray 1201 which has come perpendicularly to the sensor substrate has been incident at a point A on the prism optical element. In this case, the angle of incidence is supposed to be ω. Supposing the distance from a vertex B of the isosceles triangle to the point A is m, a part of the light that has been incident on the slope defined by the hypotenuse BC enters the flat plate portion 114 with the thickness T through a point between AB to be an unnecessary light ray 1203. The thickness T can be represented by the following Equation (5):

$$T = L \cdot \tan(90° - \omega + \theta) \cdot \{2\cos\omega - (1 - Mr)(\cos\omega + \sin\omega \cdot \tan(\omega - \theta))\} \quad (5)$$

$$Mr = \frac{m}{L}$$

In this case, the unnecessary light ray becomes equal to zero when the ratio Mr is equal to zero. A light ray that has been incident at the point B will travel as a light ray 1205 that is parallel to the light ray 1202. That is why the condition for preventing the incoming light from entering the flat plate portion 114 is that the thickness T is less than the following value K·L:

$$T_{min} = L \cdot \tan(90° - \omega + \theta) \cdot \{\cos\omega - \sin\omega \cdot \tan(\omega - \theta)\} \quad (6)$$

$$= K \cdot L$$

The ratios K were calculated with respect to multiple different ω. The results are shown in the following Table 1. If the angle of incidence ω is 60 degrees, the thickness T should be much smaller than the length L of the hypotenuse of the prism optical element. On the other hand, if the angle of incidence ω is around 50 degrees, the thickness T may be approximately as large as the length L of the hypotenuse of the prism optical element.

If this flat plate portion 114 is thin, it is difficult to make the optical element array. That is why the tilt angle of a hypotenuse of the prism optical element on its cross section may be defined to be less than 60 degrees. If this condition is satisfied, then no opaque portions 1204 are needed anymore.

TABLE 1

| ω(°) | K |
|---|---|
| 63 | 0.017 |
| 60 | 0.219 |
| 55 | 0.607 |
| 50 | 1.071 |

(Modified Example 1 of Embodiment 3)

Figure 34:
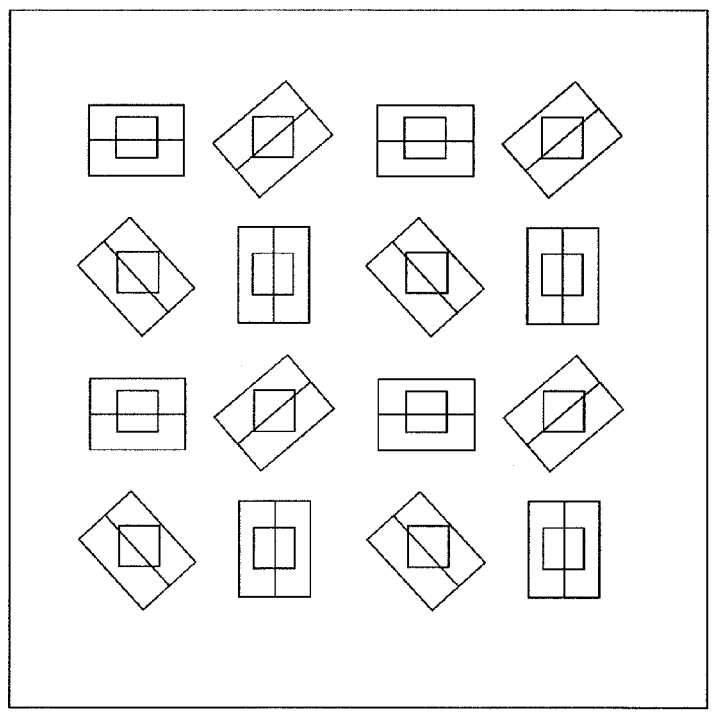
FIG. 34 illustrates a layout of prism optical elements according to a first modified example of the third embodiment, which is different from the one shown in FIG. 22.

FIG. 34 illustrates another exemplary arrangement for a prism optical element. As for which of the two exemplary arrangements shown in FIGS. 22 and 23 is more suitable than the other, it may be determined by the method of making the optical element array or the magnitude of unnecessary reflection (i.e., flare) of light from the surface of the optical element.

(Modified Example 2 of Embodiment 3)

Figure 35:
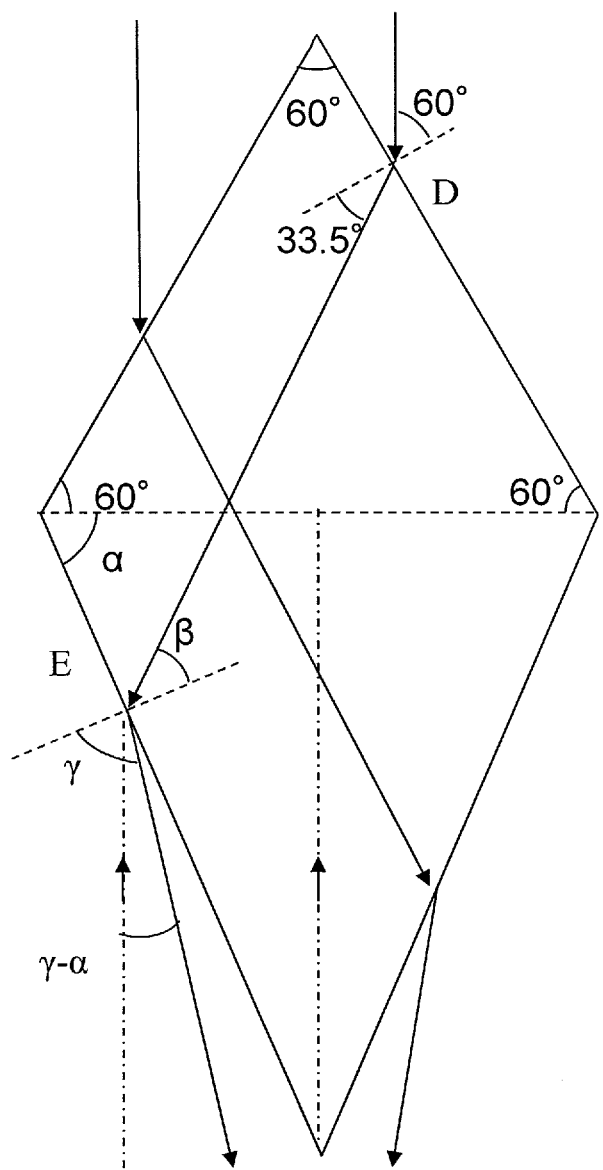
FIG. 35 illustrates a second modified example of the third embodiment in which the upper and lower prisms do not have the same shape.

FIG. 35 illustrates an example in which the upper and lower prisms do not have the same shape. In the optical element shown in FIG. 35, the angle defined by the slopes of the lower prism optical element is changed, thereby producing the effect of condensing light onto the photodiode. A light ray that has been incident at a point D on the prism optical element goes out of the prism optical element through a point E into the air. Suppose the angle of incidence at the point D is β, the angle of emittance is γ, the tilt angle defined by the slopes of the lower prism is a, and the upper prism is an equilateral triangle. Then, $$\alpha = 60° - \theta + \sin^{-1}\left(\frac{\sin\gamma}{1.5}\right) \quad (7)$$

is satisfied. In this case, if α is calculated with the γ value changed into a few other values and if the degree of condensation of the light at that time is represented by (γ−α), then the results shown in the following Table 2 are obtained:

TABLE 2

| γ(°) | α(°) | γ − α(°) |
|---|---|---|
| 70 | 63.52 | 6.48 |
| 80 | 65.77 | 14.23 |
| 90 | 66.55 | 23.45 |

As can be seen, if α=65.77 degrees, then the outgoing light ray can be condensed approximately 14.23 degrees inside with respect to a parallel light ray. As a result, the light can be condensed more efficiently onto the photodiode in the configuration shown in FIG. 21, and therefore, an even brighter image can be obtained.

(Modified Example 3 of Embodiment 3)

Figure 36:
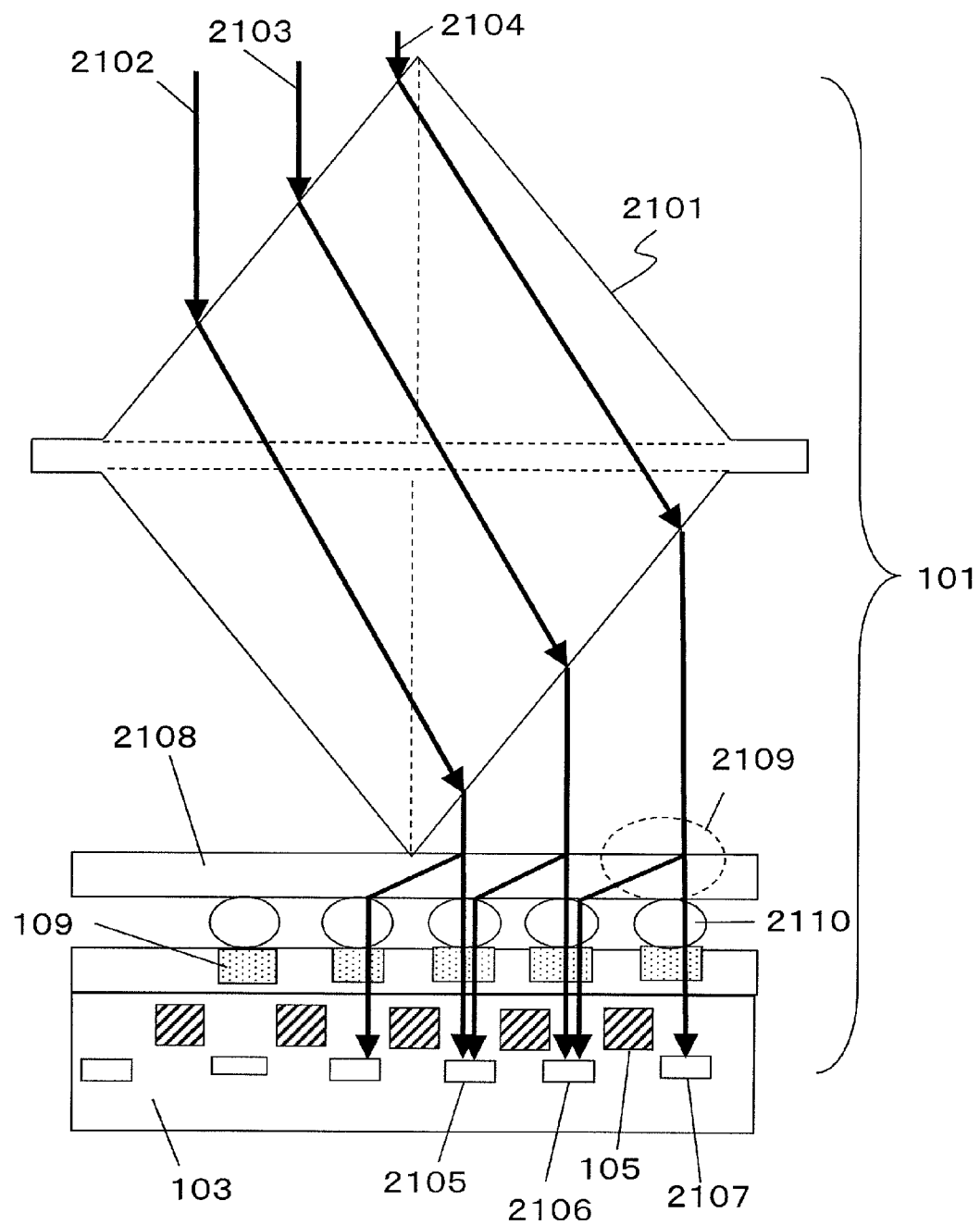
FIG. 36 illustrates a third modified example of the third embodiment according to the present disclosure.

FIG. 36 illustrates another modified example of the third embodiment. This configuration can be used effectively in a synchronous endoscope, for example. By allocating color pixels in multiple different colors to a single prism optical element, a polarization image can be generated on an RGB basis without decreasing the resolution of a normal color image. According to such a modified example, each prism optical element 2101 can be designed to have a larger size than a pixel. That is why the optical element array can be made easily.

In FIG. 36, illustration of the lens 110, the supporting member 113 and other members shown in FIG. 21 is omitted. In the example shown in FIG. 36, three incoming light rays 2102, 2103 and 2104 that have entered the prism optical element 2102 through one of its slopes are refracted to be incident on multiple different pixels (i.e., multiple different photodiodes 2105, 2106 and 2107, respectively). The color filter 109 forms part of a mosaic filter such as a Bayer filter. That is why the quartz LPF 2108 is arranged behind the prism optical element (i.e., more distant from the light source than the prism optical element is), and the light rays have their paths shifted as indicated by the reference numeral 2109 to be incident on adjacent pixels. The quartz LPF 2108 is formed by stacking multiple quarter wave plates, each of which transforms a polarized light ray into a circularly polarized light ray, and multiple quartz LPFs, each of which splits the incoming light ray into two light rays by birefringence, one upon the other.

Optionally, to condense the incoming light onto the photodiodes, micro lenses 2110 may be arranged. It should be noted that the number of photodiodes (i.e., the number of pixels in the mosaic filter) that are associated with the incident plane of a single prism optical element 2101 does not have to be three. Actually, the photodiodes are arranged to form a two-dimensional plane. Thus, any other number of photodiodes may be associated with the incident surface of a single prism optical element 2101 as long as the mosaic interpolation processing can be carried out.

The quartz LPF 2108 is an indispensable element for an image capturing system that uses a mosaic filter such as a Bayer filter. However, since the quartz LPF 2108 uses a birefringence phenomenon, multiple different polarized light rays will be incident on a single pixel in mixture, and the polarization state of the incoming light ray will change. Thus, in this example, the quartz LPF 2108 is arranged behind the prism optical element 2101 and is used after the polarization state of the incoming light has been converted into a light intensity variation.

Figure 37A:
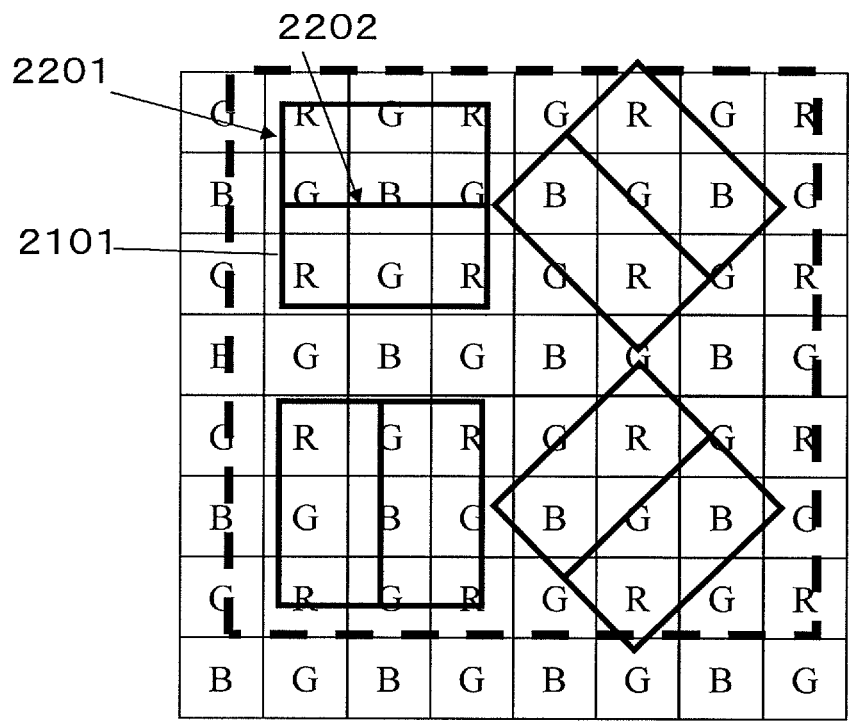
FIG. 37A shows a plan view of the structure shown in FIG. 36 as viewed from over it.

FIG. 37A is a top view of the structure shown in FIG. 36. In FIG. 37A, illustrated are four prism optical elements 2101 with mutually different azimuth angles. In an actual polarization image sensor, however, a much greater number of prism optical elements 2101 are arranged. Each slope of a single prism optical element 2101 is associated with multiple photodiodes (i.e., multiple pixels). To obtain color information, color filters are arranged to form a Bayer arrangement mosaic. More specifically, in this example, four prism optical elements with mutually different directions are associated with 7×7 pixels of the Bayer mosaic.

On a top view, each prism optical element 2101 has a square shape and covers at least every one of R, G and B pixels. The square area 2201 covered with each prism optical element 2101 is divided into two rectangular areas at an edge line 2202. In the case of an ordinary color image to be generated based on non-polarized light, there should be no variation in light intensity due to the polarized light produced by the four kinds of prism optical elements 2101. That is why an ordinary Bayer mosaic interpolation method may be taken. However, when the incoming light rays 106 are transformed into outgoing light rays 108 as shown in FIG. 21, the light rays change their positions with each other. Specifically, in the exemplary configuration shown in FIG. 21, the two light rays that have entered each prism optical element through its two slopes that are tilted in mutually opposite directions are made to be incident on a photodiode 109 associated with a single pixel. In the exemplary configuration shown in FIGS. 36 and 37A, on the other hand, the two light rays that have entered each prism optical element through its two slopes will be incident on mutually different photodiodes. As such a position change of light rays affects the light intensities of pixels, the pixel arrangement can be corrected. Such a correction can be made by an image processor to be described later, for example.

Figure 37B:
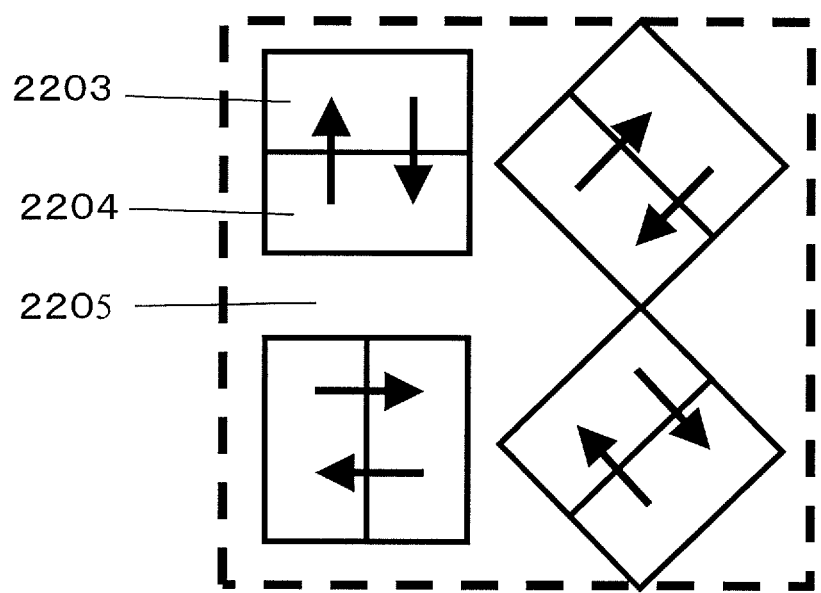
FIG. 37B illustrates how the optical element shown in FIG. 36 corrects the locations of pixels.

FIG. 37B illustrates such a pixel arrangement correction. For example, the rectangular areas 2203 and 2204 which are defined by the edge line may be changed with each other as indicated by the two arrows. The same can be said about prism optical elements with other directions. However, this correction does not have to be made on the flat plate region 2205.

Figure 38:
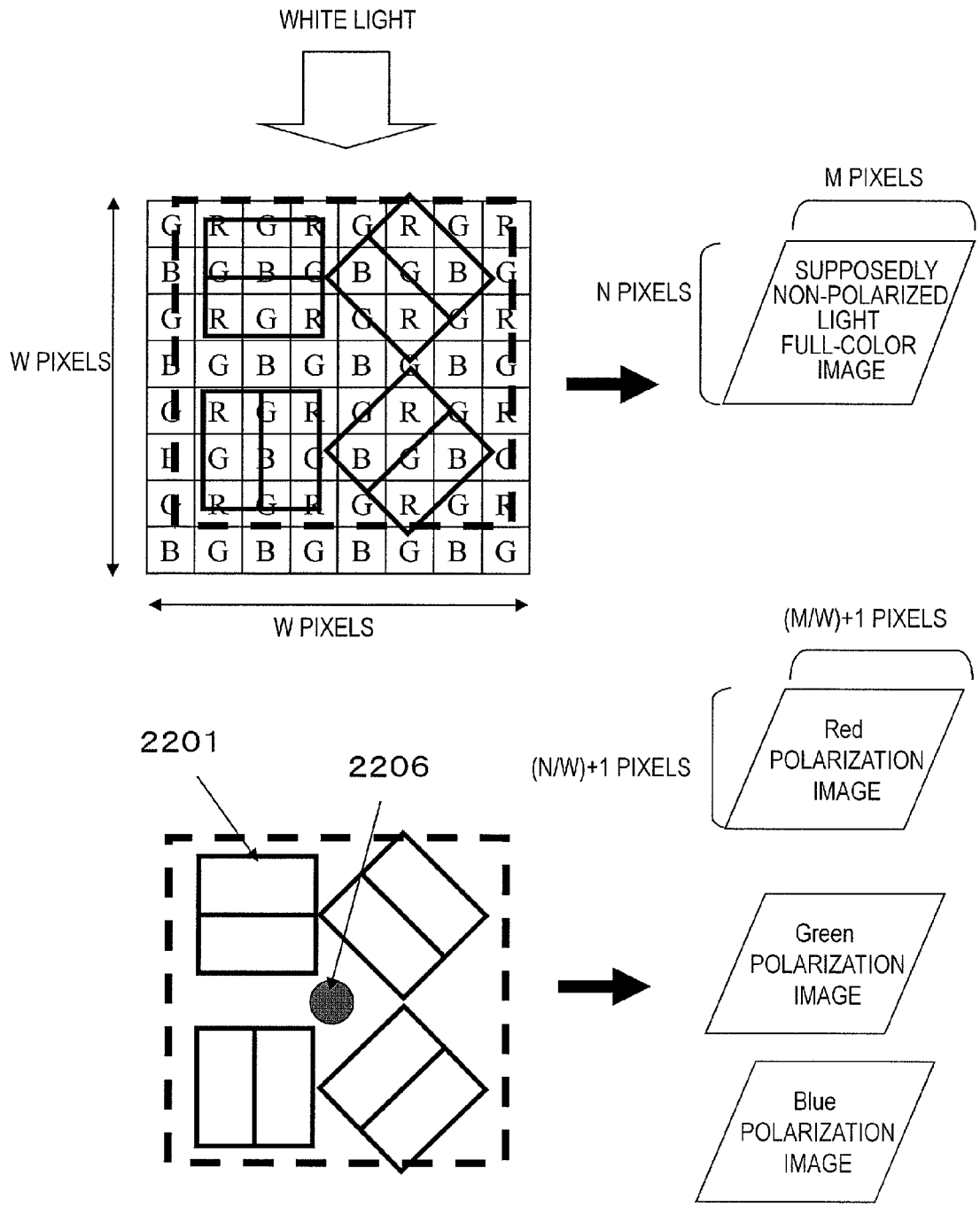
FIG. 38 shows the resolutions of a supposedly non-polarized light full-color image and a polarization image to be used when a "synchronous" endoscope as a modified example of the first embodiment of the present disclosure obtains color information.

FIG. 38 illustrates output images generated as a result of this processing and their resolutions. First of all, a supposedly non-polarized light full-color image is generated to have a resolution of M×N pixels. On the other hand, as four different kinds of prism optical elements are used as one unit, polarization images that use the center 2206 of each unit as one pixel are obtained. Supposing the number of pixels included in a single unit is W×W pixels, the resolution of a color polarization image becomes ((M/W)+1)×((N/W)+1) pixels. In FIG. 38, a single unit is drawn on the supposition that W=7.

As described above, in generating a supposedly non-polarized color image, the color image can be obtained with the original maximum resolution of the image sensor maintained. Even though the resolutions of the polarization images decrease, the polarization images can be obtained on a color by color basis. It is true that a decrease in the resolution of a polarization image is not beneficial but various artifacts such as a moiré are not produced easily because the image is not obtained at the highest spatial frequency.

(Modified Example 4 of Embodiment 3)

Figure 39:
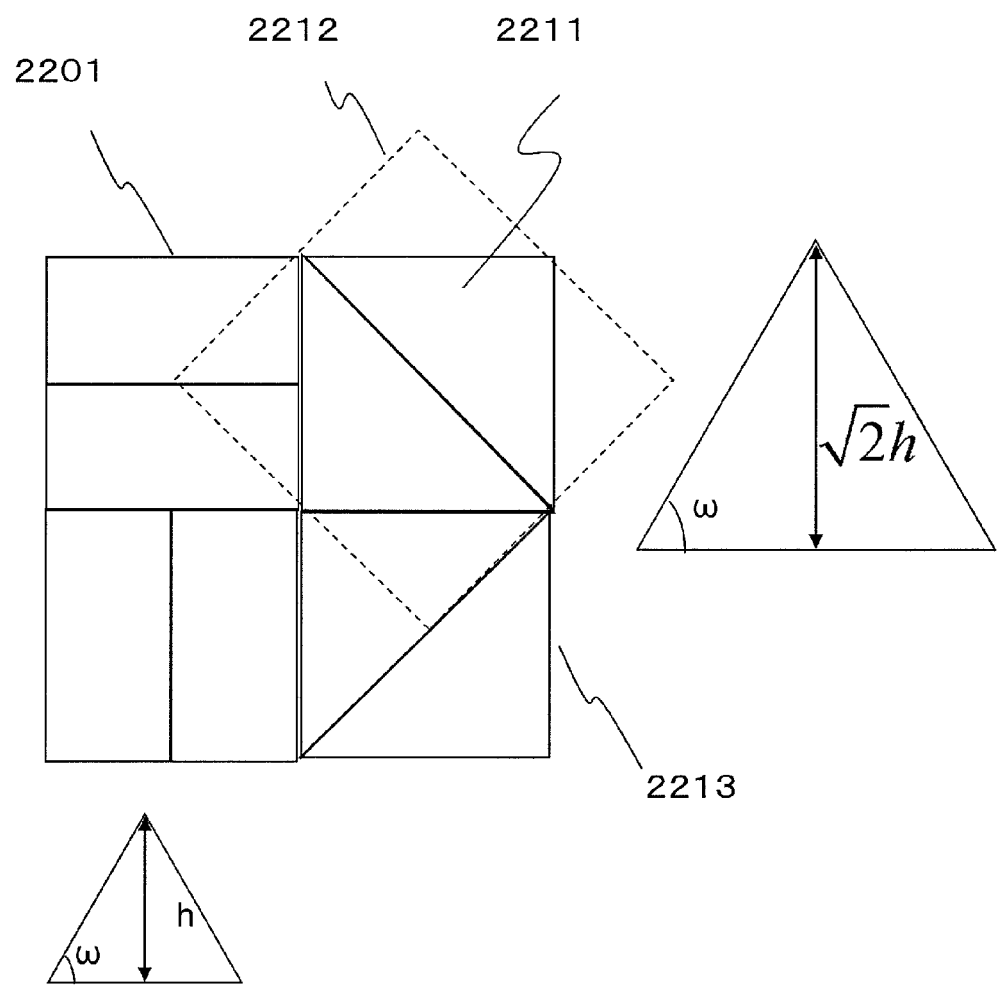
FIG. 39 illustrates a fourth modified example of the third embodiment of the present disclosure.
Figure 40:
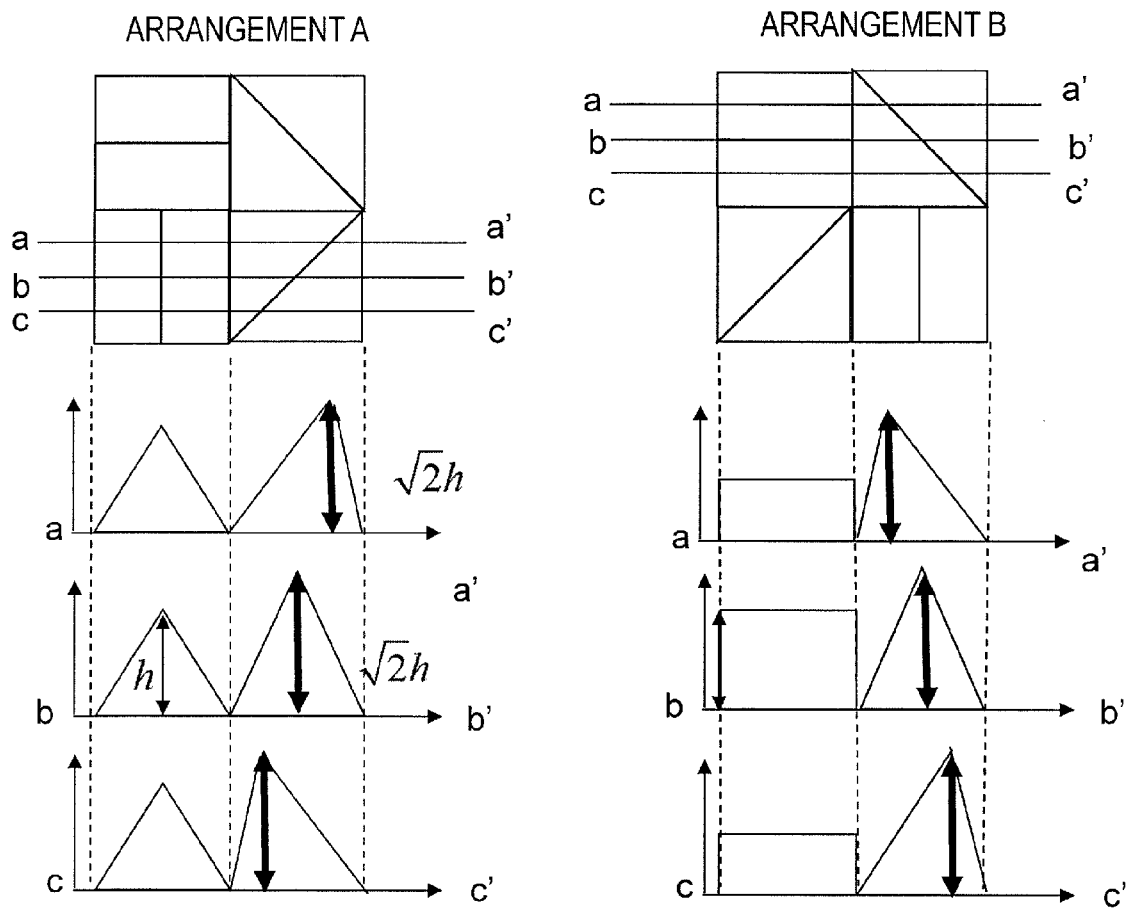
FIG. 40 illustrates cross sections of the fourth modified example of the third embodiment of the present disclosure.

FIGS. 39 and 40 illustrate a fourth modified example of the third embodiment. Up to the third modified example of the third embodiment, the square area 2201 associated with each prism optical element 2101 does not cover every color mosaic pixel but some pixels are covered with the flat plate portion 2205 that connects multiple optical elements together as shown in FIGS. 37A and 37B. In this modified example, by substantially removing such a flat plate portion 2205 from the optical element array, every pixel can be covered with a prism optical element.

FIG. 39 illustrates the planar structure of one unit consisting of four different kinds of optical elements. In this example, these four optical elements are arranged densely so as to leave no flat plate area in the square area 2201. Also, the projection areas of the prism optical element 2211 with an azimuth angle of 45 degrees and the prism optical element 2213 with an azimuth angle of 135 degrees are equal to the projection area of the optical element 2201 with an azimuth angle of 0 degrees. Thus, each optical element may be expanded with its stereoscopic shape maintained. For example, the prism optical element 2211 forms part of a prism optical element 2212 which has an azimuth angle of 45 degrees and which has a larger size than the prism optical element 2201. In this configuration, the vertex height of the prism optical element 2211 is $\sqrt{2}$ times as large as that of the prism optical element 2201 because the prism optical element 2211 has the same angle as, but a longer slope than, the prism optical element 2201.

FIG. 40 illustrates the cross-sectional shapes of two exemplary arrangements A and B of prism optical elements as viewed on three different planes a-a', b-b' and c-c, respectively.

(Embodiment 4)

Figure 41:
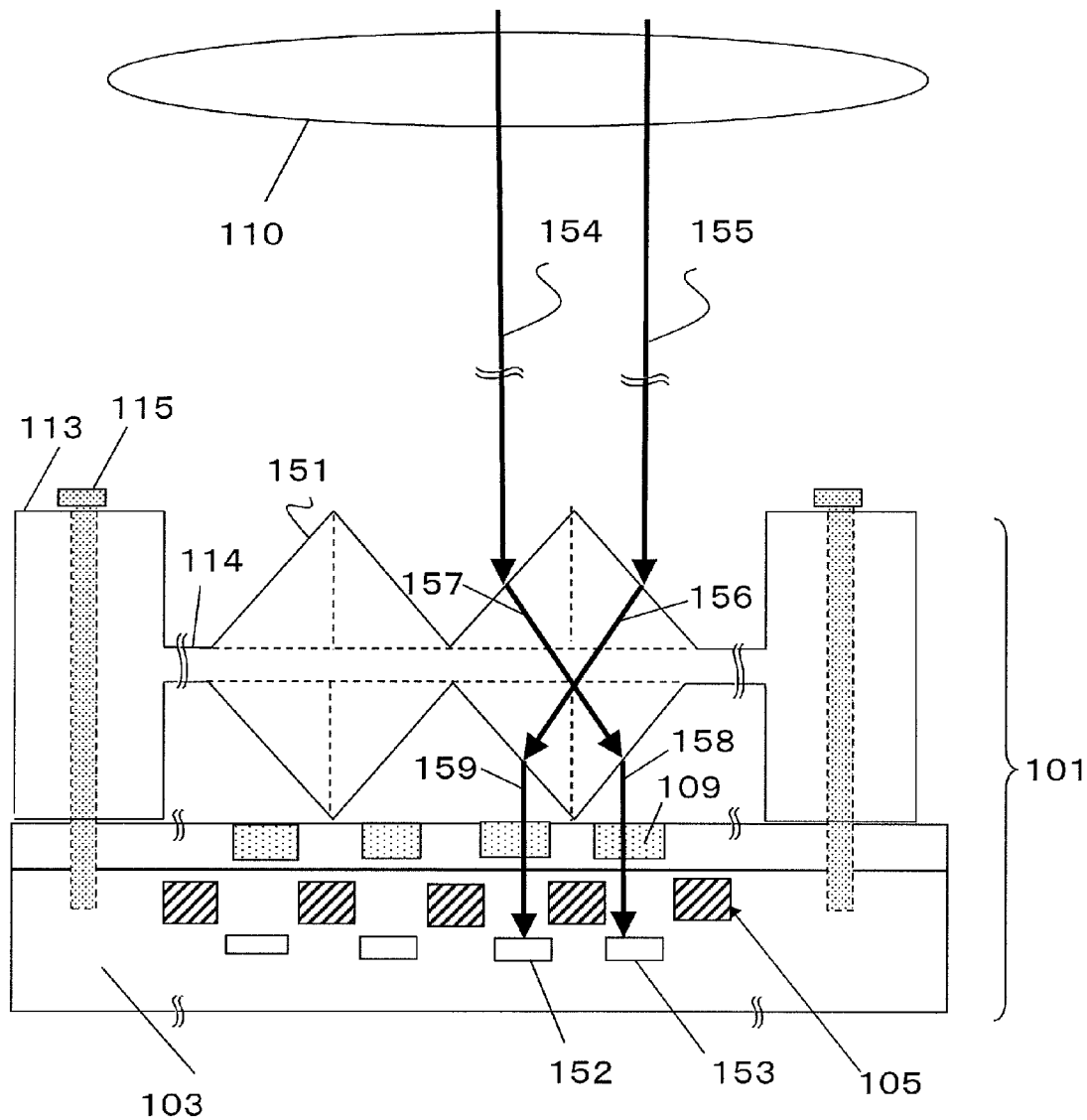
FIG. 41 shows a cross-sectional view illustrating a polarization image sensor as a fourth embodiment of the present disclosure.

FIG. 41 is a cross-sectional view illustrating the multilayer structure of a polarization image sensor as a fourth embodiment of the present disclosure. This embodiment and the embodiment illustrated in FIG. 21 are the same except prism optical elements 152 and pixel sensors 152, 153.

Each prism optical element 151 covers multiple photodiodes 152, 153, for example. The incoming light rays 154 and 155 that have been transmitted through the objective lens 110 get refracted by the slopes of the prism optical element 151 and enter the prism optical element 151 to turn into refracted light rays 156 and 157, which get further refracted by other surfaces of the prism optical element 151 to be outgoing light rays 158 and 159. The outgoing light rays 158 and 159 are transmitted through the color filters 109 to reach the photodiodes 153 and 152.

Figure 42:
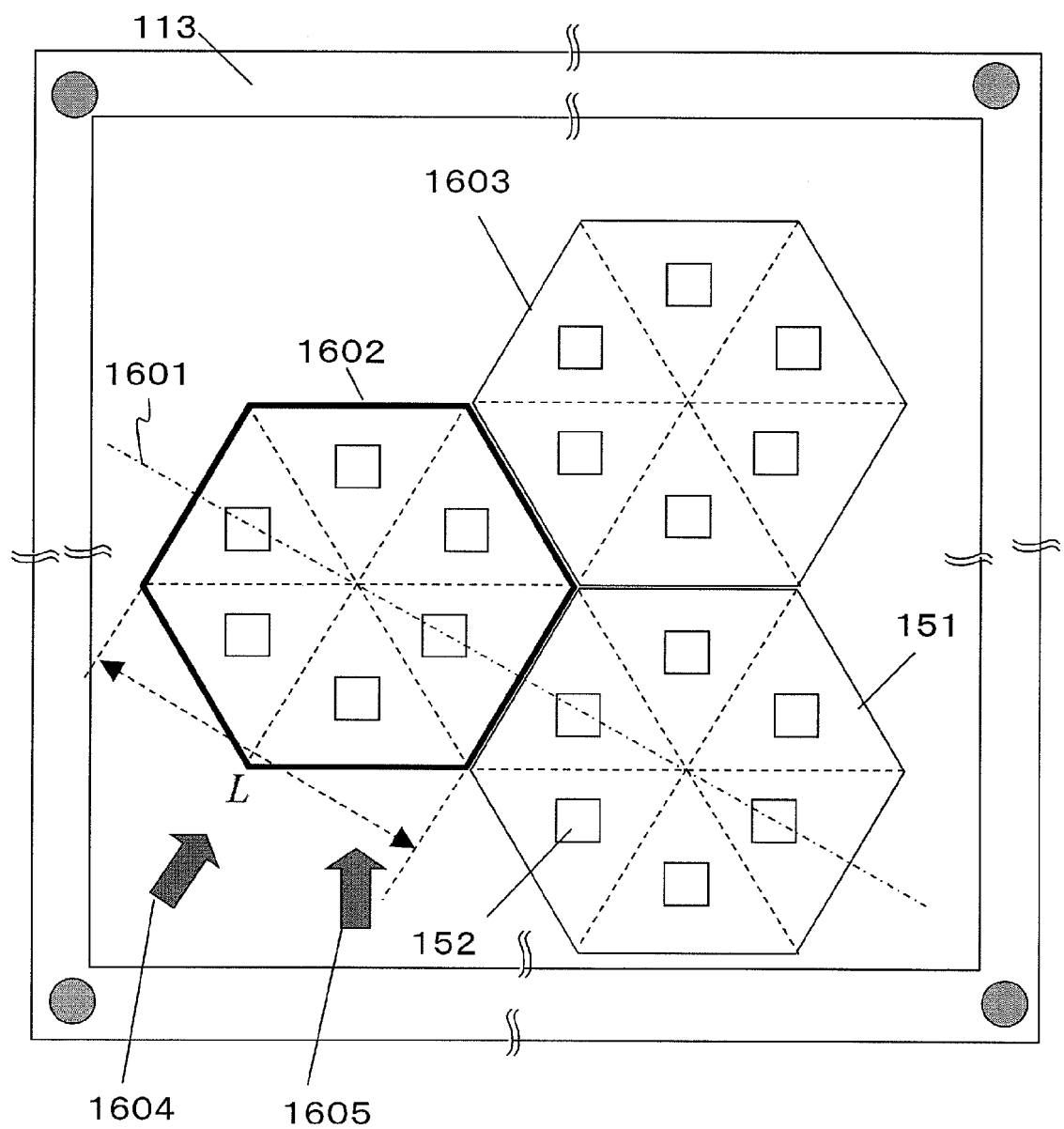
FIG. 42 shows a plan view of a polarization image sensor according to the second embodiment of the present disclosure as viewed from over the objective lens.

FIG. 42 is a plan view illustrating this polarization image sensor as viewed from over the objective lens. A cross-sectional view as viewed on the plane indicated by the dotted line 1601 is FIG. 41. In FIG. 42, illustrated are three areas 1602, 1603 and 1604, which are covered with three prism optical elements 151. As shown in FIG. 42, each prism optical element 151 has a hexagonal bottom. Accordingly, each group of photodiodes are also arranged at the vertices of the hexagon. The entire optical element array is secured to the sensor substrate with a supporting member 113 and fixing screws 115. In FIG. 42, illustrated are only three prism optical elements and eighteen photodiodes. Actually, however, a lot more optical elements and far more photodiodes are arranged there. Each and every hexagonal cell selected from this arrangement on the plane (e.g., the area 1602, 1603) has triangular slopes with three different azimuths. Consequently, by processing an image captured using such a hexagonal cell as a unit, the plane of vibration of polarized light can be estimated.

FIG. 43 illustrates a single prism optical element 151 as viewed in the directions indicated by the arrows 1604 and 1605 shown in FIG. 42. This prism optical element 151 has a shape in which upper and lower hexagonal pyramids are bonded together on their hexagonal bottom corresponding to their hexagonal planar structure. The optical element array may be made by subjecting a single transparent plate to a cutting or any other machining process.

Figure 44A:
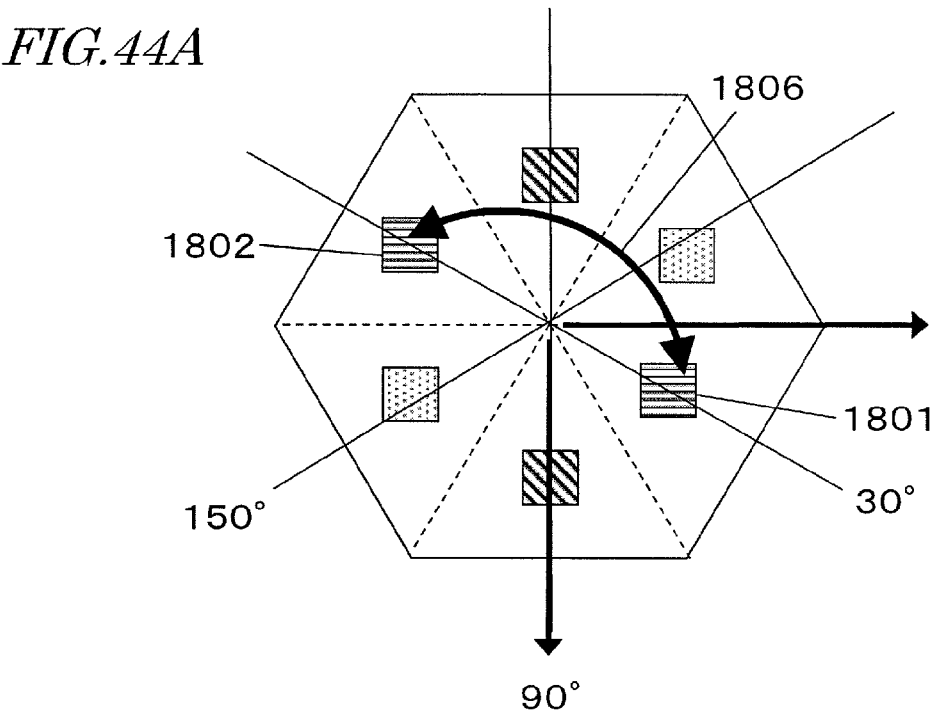
FIG. 44A illustrates a prism optical element of which the slopes are arranged in three different directions so that the directions are different from each other by 60 degrees between each pair of adjacent pixels.
Figure 44B:
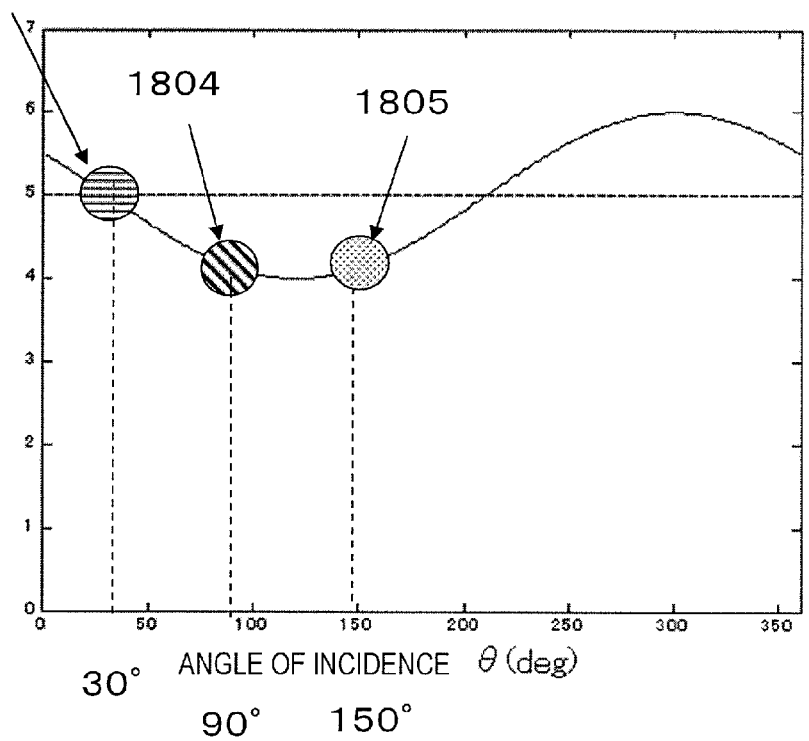
FIG. 44B shows how to perform the processing of obtaining polarization information based on signals supplied from pixels in a hexagonal cell.

FIG. 44A illustrates a prism optical element, of which the slopes are arranged in three different directions so that the azimuth angles are different from each other by 60 degrees between each pair of adjacent pixels. FIG. 44B shows how to get polarization information based on the signals supplied from pixels in such a hexagonal cell. If the incoming light is non-polarized light, the light intensities obtained by photodiodes corresponding to six pixels that are obtained by using this hexagonal cell as a processing unit are equal to each other. If the incoming light is polarized light, however, the light intensities obtained by those photodiodes will be different from each other depending on the plane of vibration of the polarized light. For example, pixels 1801 and 1802 which are located right under two slopes, to which a normal defines a direction corresponding to an azimuth angle of 30 degrees, have the same pixel value. Thus, a light intensity value 1803 is obtained by calculating the average of these two light intensity values. In the same way, obtained are the light intensity value 1804 of pixels, which are located right under two slopes, to which a normal defines a direction corresponding to an azimuth angle of 90 degrees, and the light intensity value 1805 of pixels, which are located right under two slopes, to which a normal defines a direction corresponding to an azimuth angle of 150 degrees. On the graph shown in FIG. 44B, these light intensity values are plotted. In this case, fitting can be made with a sinusoidal function including the three unknown numbers A, B and C of Equation (1). Three equations are obtained for those three unknown numbers.

Next, it will be described how to get color information.

Figure 45:
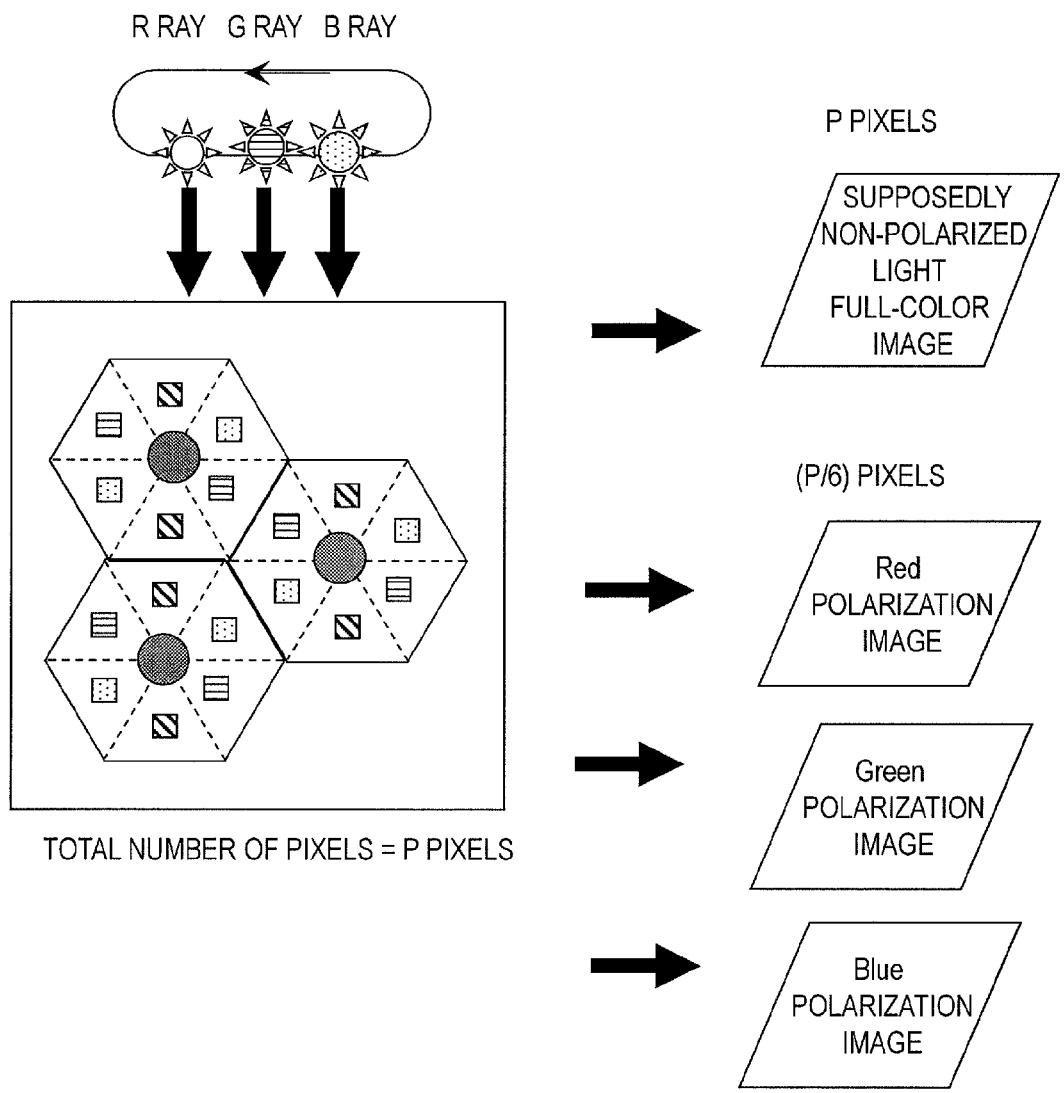
FIG. 45 shows how to obtain color information using a "frame sequential" endoscope according to the second embodiment of the present disclosure.

FIG. 45 illustrates how to get color information by using the polarization image sensor of this embodiment in an endoscope of the so-called "frame sequential type". By carrying out the processing described above on each of the RGB bands, color-by-color polarization information can be obtained. In this case, a polarization image is generated by using each of those hexagonal areas 1602 and 1603 as a pixel. That is why if the total number of pixels of the sensor substrate is P, the overall resolution decreases to (P/6) pixels. However, if an ordinary full-color image is generated based on non-polarized returning light, the resolution does not decrease and those P pixels can be used effectively.

It should be noted that the incoming light rays 154 and 155 interchange their paths with each other to be eventually incident on the photodiodes 153 and 152, respectively, as shown in FIG. 41. That is why in order to generate a high resolution image (i.e., to generate a color image under non-polarized light, for example), the pixel values of the pixels 1801 and 1802, which are located symmetrically with respect to the center of the hexagonal area shown in FIG. 44A, are changed with each other as indicated by the arrow 1806.

Figure 46:
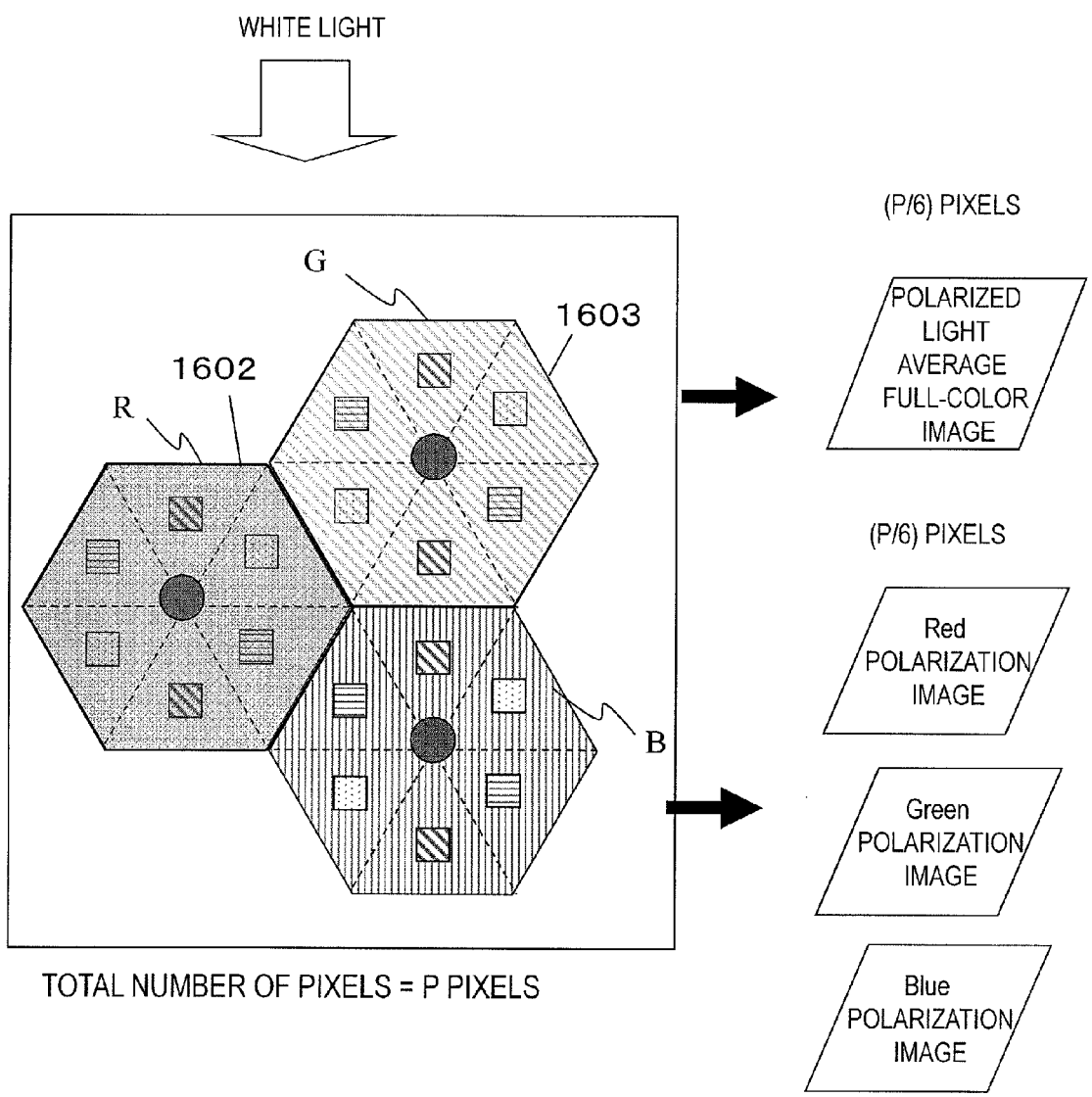
FIG. 46 shows how to obtain color information using a "synchronous" endoscope according to the second embodiment of the present disclosure.

FIG. 46 illustrates how to make a color representation using the polarization image sensor of the present disclosure in a so-called "synchronous" endoscope. As shown in FIG. 46, in the synchronous endoscope, the illumination is white light and a color mosaic filter is arranged closer to the image sensor. In the example illustrated in FIG. 46, one of the three colors of RGB of the color mosaic filter is allocated to each of the hexagonal areas 1602, 1603, etc. which are covered with the prism optical elements. Then, the resolutions of resultant color polarization images and ordinary full-color image both decrease to (P/6) pixels.

(Embodiment 5)

Figure 47:
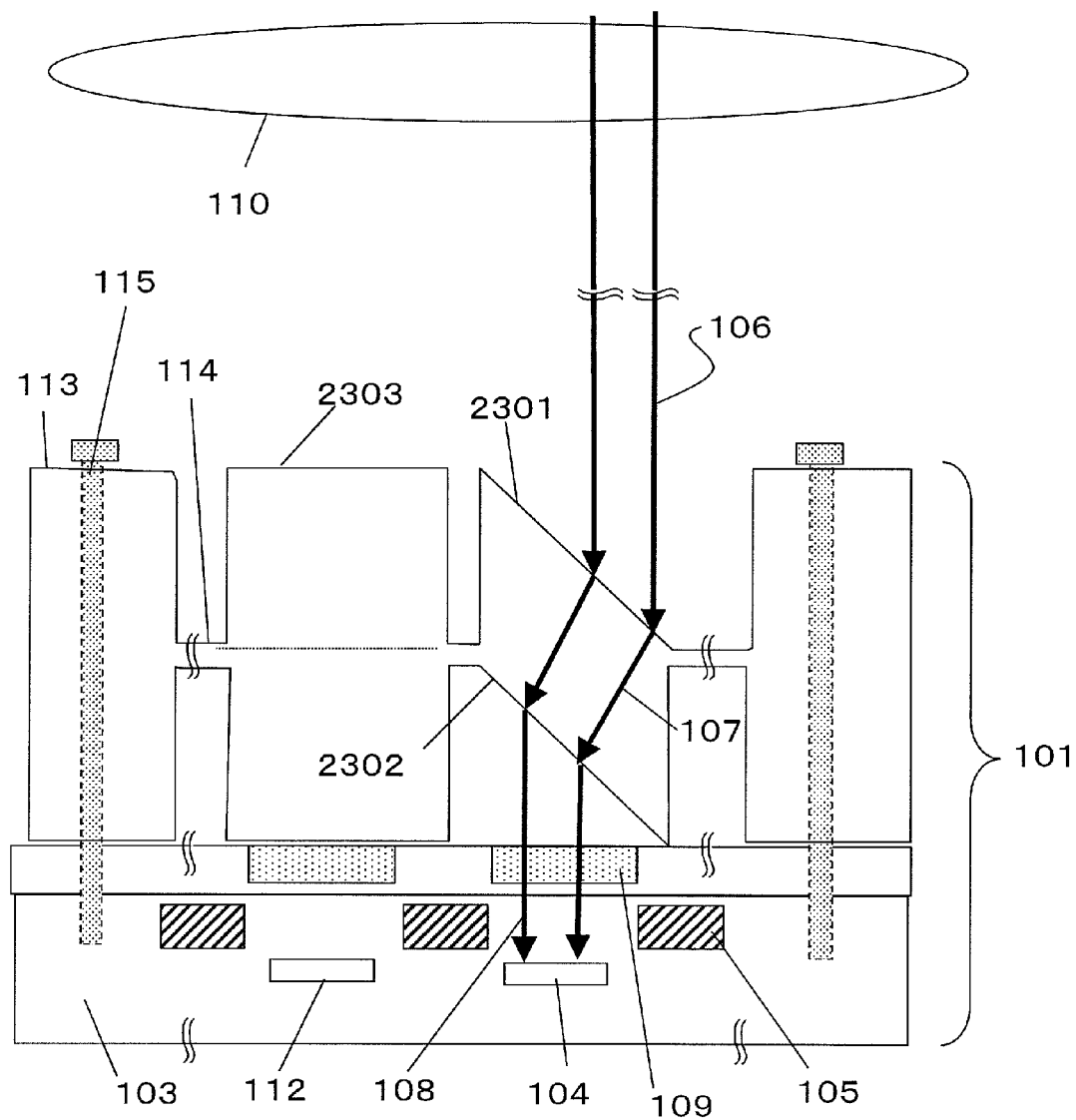
FIG. 47 shows a cross-sectional view illustrating a fifth embodiment of the present disclosure.

FIG. 47 illustrates an exemplary cross-sectional structure for a polarization image sensor as a fifth embodiment of the present disclosure. The difference between this and third embodiments lies in the cross-sectional shape of the optical elements. Specifically, the optical element 2303 of this embodiment has first and second surfaces 2301 and 2302 which are tilted and has a parallelogram cross-sectional shape.

(Embodiment 6)

Figure 48:
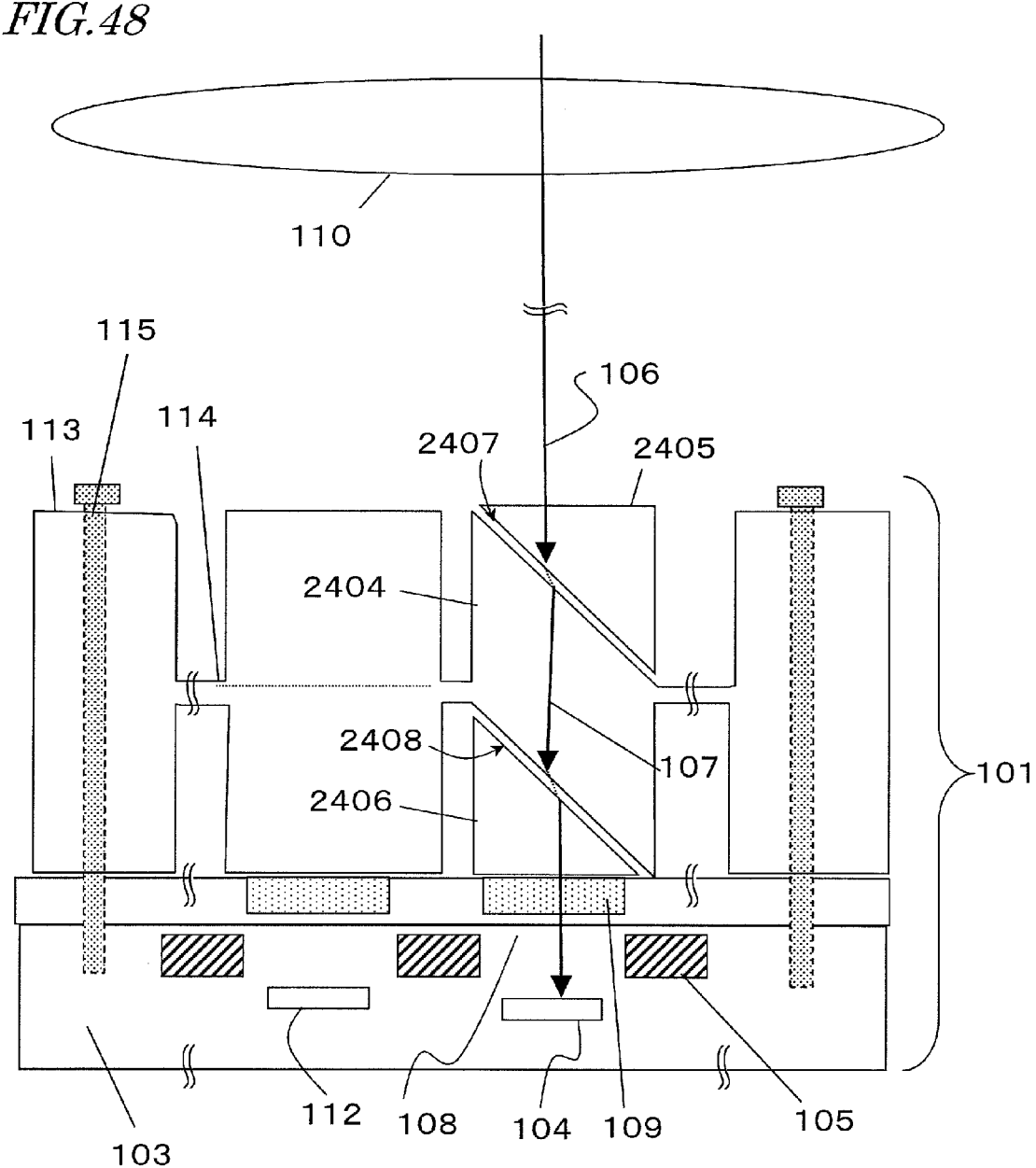
FIG. 48 shows a cross-sectional view illustrating a sixth embodiment of the present disclosure.

FIG. 48 illustrates an exemplary cross-sectional structure for a polarization image sensor as a sixth embodiment of the present disclosure. The difference between this and fifth embodiments lies in arranging elements 2405 and 2406 with a right triangular cross section over and under the optical element 2404. Air layers 2407 and 2408 are left between the optical element 2404 and the element 2405 and between the optical element 2404 and the element 2406, respectively. By adopting such a configuration, the number of times of refraction and transmission increases, and therefore, the polarized light selectivity can be increased, which is beneficial. Also, as shown in FIG. 48, if the upper surface of the element 2405 is flat and parallel to the image capturing plane, then the entire upper surface of the optical element array will be generally flat, thus making the optical elements almost dust free and well protected.

(Embodiment 7)

Figure 49:
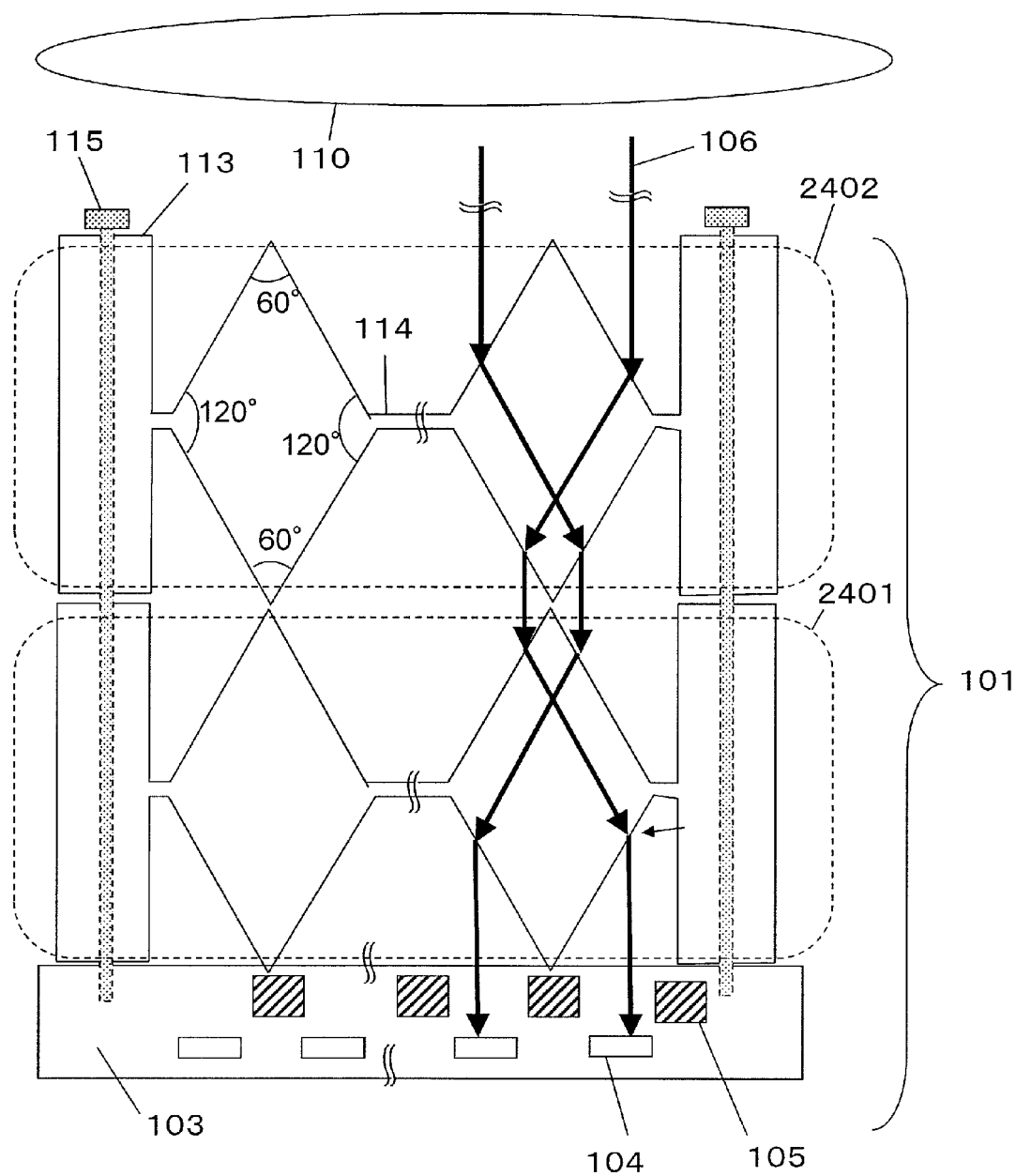
FIG. 49 shows a cross-sectional view illustrating a seventh embodiment of the present disclosure.

FIG. 49 illustrates an exemplary cross-sectional structure for a polarization image sensor as a seventh embodiment of the present disclosure. In this embodiment, optical elements are stacked one upon the other. In other words, the optical element array of this embodiment has a double layer structure. By adopting such a configuration, the incoming light will be refracted more than twice, thus increasing the polarized light selectivity. In addition, as the incoming light rays cross each other twice, there is no need to perform the pixel exchange processing. The number of layers stacked in the optical element array does not have to be two but may also be an odd number. Optionally, similar elements to the elements 2405 and 2406 shown in FIG. 48 may be arranged in the gap between the adjacent ones of the optical elements stacked in the array.

(Embodiment 8)

Figure 50:
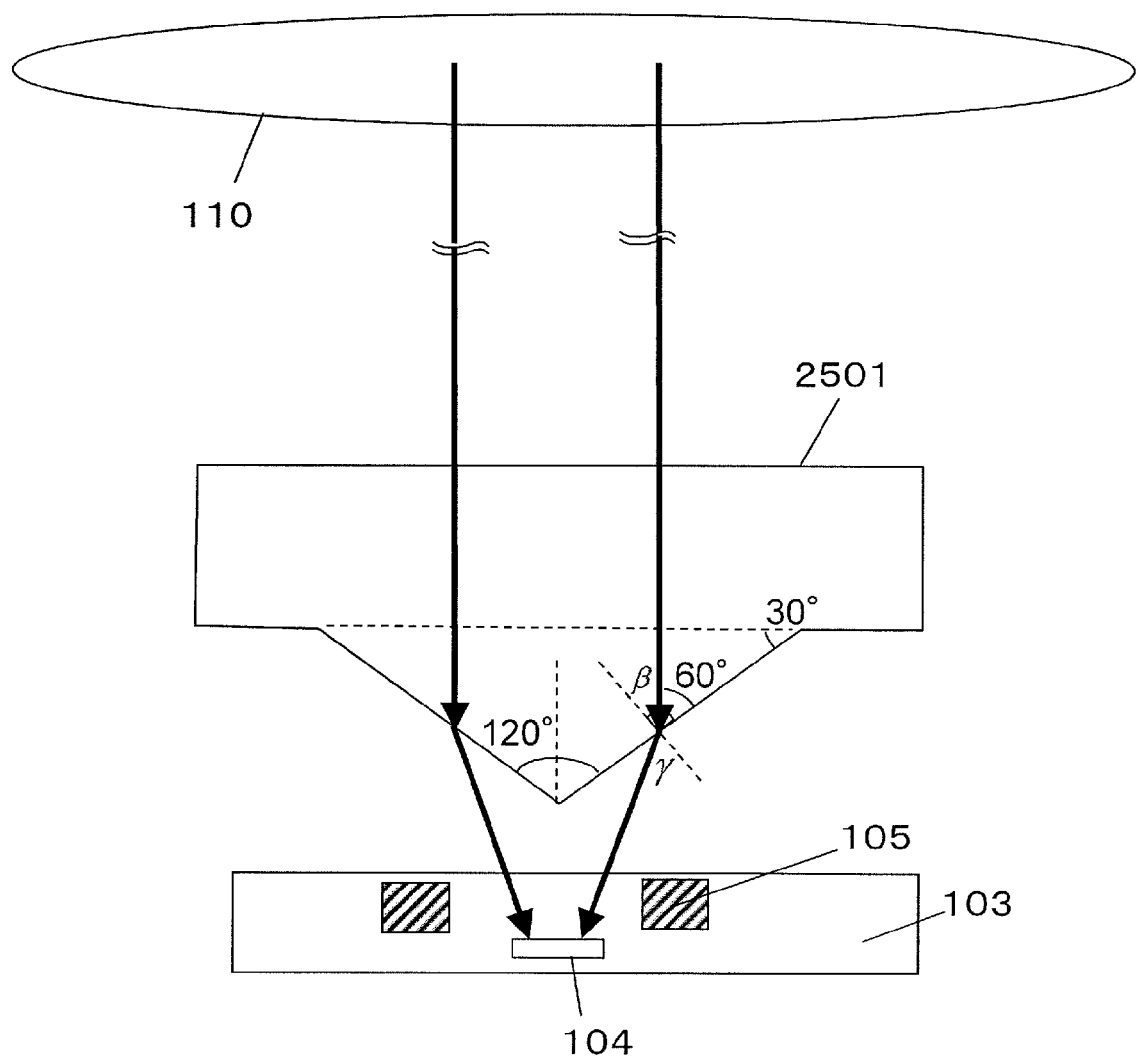
FIG. 50 shows a cross-sectional view illustrating an eighth embodiment of the present disclosure.

FIG. 50 illustrates an exemplary cross-sectional structure for a polarization image sensor as an eighth embodiment of the present disclosure. Even though the cross-sectional shape of its characteristic optical element 2501 is illustrated in FIG. 50, illustration of the other parts is omitted for the sake of simplicity. The light incoming side of the optical element 2501 has a flat surface. Sloped surfaces that form a prism are present on only the light outgoing side of the optical element 2501. When $\beta=30$ degrees, $\gamma=48.6$ degrees. If such an optical element is adopted, the incoming light ray gets refracted only once and the polarized light selectivity decreases slightly. However, the flat plate portion that connects multiple optical elements together can be thickened. In addition, if the optical element array is made by machining a transparent plate, the machining process needs to be performed on only one side, and therefore, such an array can be made easily.

(Embodiment 9)

Figure 51:
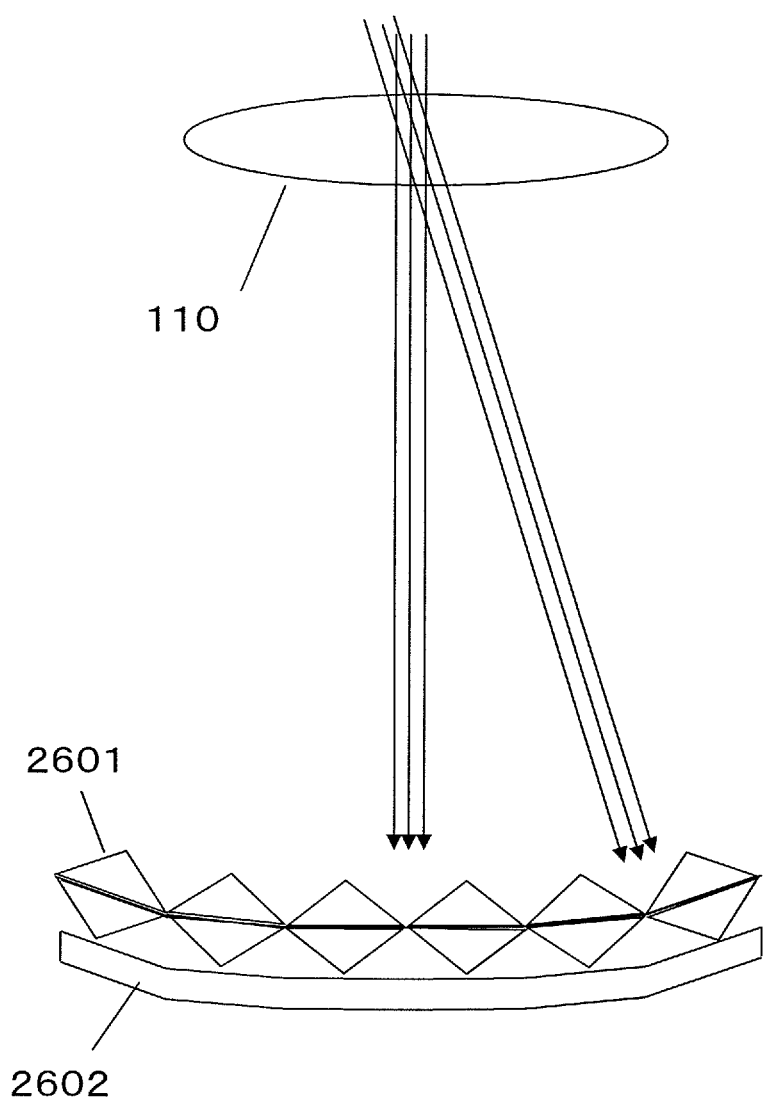
FIG. 51 shows a cross-sectional view illustrating a ninth embodiment of the present disclosure.

FIG. 51 illustrates an exemplary cross-sectional structure for a polarization image sensor as a ninth embodiment of the present disclosure. In this embodiment, the basic configuration is unchanged from that of the third embodiment described above, but the sensor substrate 2602 with the image sensor, as well as the optical element array 2601, is bent inward. With such a configuration adopted, the light rays that have come through the objective lens 110 are incident on the optical elements parallel, not obliquely. Thus, when this polarization image sensor is applied to an endoscope that needs wide-angle shooting, for example, a high-definition polarization image can be obtained in a broad range. It should be noted that the configuration of this embodiment is applicable to any of the third through eighth embodiments described above.

Hereinafter, an endoscope with a polarization image sensor according to any of the first through ninth embodiments described above will be described.

FIG. 52 illustrates how a polarization image sensor according to the present disclosure may be applied to an endoscope to perform the function of separating light scattered from the surface of an organ's mucosa from light scattered from the depth. Recently, in the field of digestive organ endoscopes, NBI (narrow band imaging) endoscope technologies have become more and more popular. When inspection is carried out using a conventional endoscope, white light with a broad spectrum width tends to decrease the contrast ratio of blood vessel and other microscopic pattern on the mucosa surface layer, which are important factors in making a diagnosis. To overcome such a problem of a decreased contrast ratio, the NBI endoscope uses narrow band light as illuminating light, thereby displaying the capillary blood vessel and microscopic pattern on the mucosa surface layer with the difference in their color tone emphasized. If the NBI endoscope is adopted, however, the illuminating light becomes narrow band color light, and therefore, the images darkens and the colors of the object cannot be reproduced accurately.

In contrast, the polarization image sensor of the present disclosure can not only display a bright image but also reproduce the colors of the object accurately, and therefore, can be used effectively in the field of endoscopes.

FIG. 52(A) illustrates the illuminating light emitting side. The endoscope 3001 includes an objective lens 3002 and a linearly polarized illuminating light lens 3003. The objective lens 3002 is equivalent to the objective lens 100 of the embodiments described above. Although not shown in FIG. 52(A), a polarization image sensor according to the present disclosure is arranged behind the objective lens 3002. The linearly polarized illuminating light 3004 is white light. In this example, the endoscope operates on the so-called synchronous method. That is why the embodiments of the polarization image sensor that adopt the synchronous method are applicable. Naturally, the image sensor of the present disclosure is also applicable to an endoscope that operates on the frame sequential method. The linearly polarized illuminating light irradiates the mucosa 3005 on the surface of the target organ.

FIG. 52(B) illustrates a situation where the light that has irradiated the object has returned and imaged. The light that has returned from a relatively shallow portion 3006 of the object remains linearly polarized light, but the light that has returned from a deep portion has gotten scattered and become non-polarized light. That is to say, even though polarized reflected light components and non-polarized reflected light components are in mixture, the polarized light components can be separated and blood vessel and microscopic mucosa pattern in the vicinity of the surface layer can be displayed with their contrast emphasized by adopting this polarization image sensor.

Figure 53:
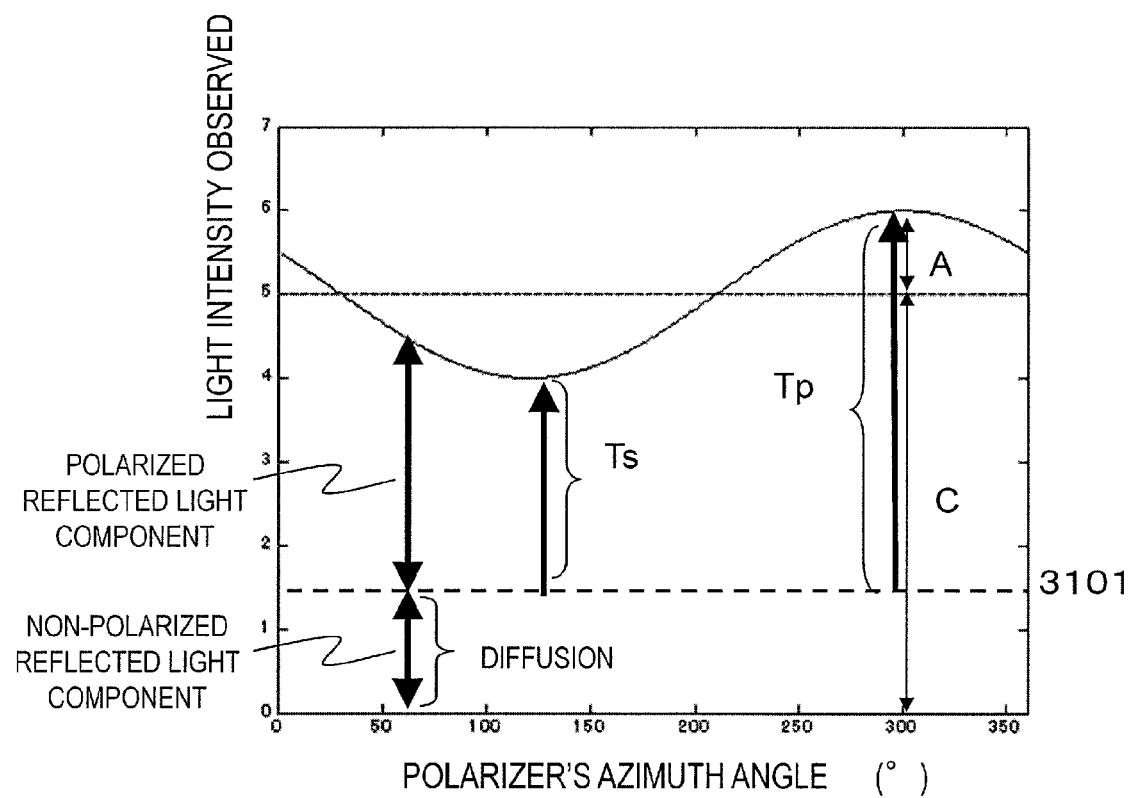
FIG. 53 shows a graph showing how the light intensity varies due to the light reflected from an organ's mucosa.

FIG. 53 is a graph showing how the light intensity of an image that has been captured and subjected to a sine fitting process with the polarization image sensor of the present disclosure varies with the azimuth angle of a polarizer. In the graph shown in FIG. 53, only one of the three primary colors of RGB is shown as an example. Although the non-polarized reflected light component diffuse becomes a constant value irrespective of the azimuth angle of the polarizer, the polarized reflected light component does vary according to the azimuth angle of the polarizer. Nevertheless, as the polarized reflected light component does not vary with the maximum amplitude, the boundary line 3101 on which those two kinds of components are separated from each other may be determined in the following procedure.

As can be seen easily from FIGS. 24 and 25, the polarization image sensor of the present disclosure receives P- and S-polarized light rays as a combination of incoming light rays and as a combination of outgoing light rays at the maximum light intensity point and at the minimum light intensity point, respectively. And as can be seen from FIG. 26, this ratio is known as the extinction ratio Kratio. For example, at an angle of incidence of 60 degrees, the extinction ratio Kratio=1.5. That is to say, if this angle of incidence is adopted, $$Kratio = \frac{T_P}{T_S} = 1.5 \tag{8}$$

is satisfied. The polarized light selectivity can be represented by the following Equation (9) using the amplitude A and average C that are already known through the sine fitting process and the unknown number diffuse:

$$Kratio = \frac{C + A - \text{diffuse}}{C - A - \text{diffuse}} \tag{9}$$

Consequently, the boundary line 3101 can be defined and the components can be separated from each other by the following Equation (10):

$$\text{diffuse} = C - \left(\frac{Kratio + 1}{Kratio - 1}\right) A \tag{10}$$

Figure 54:
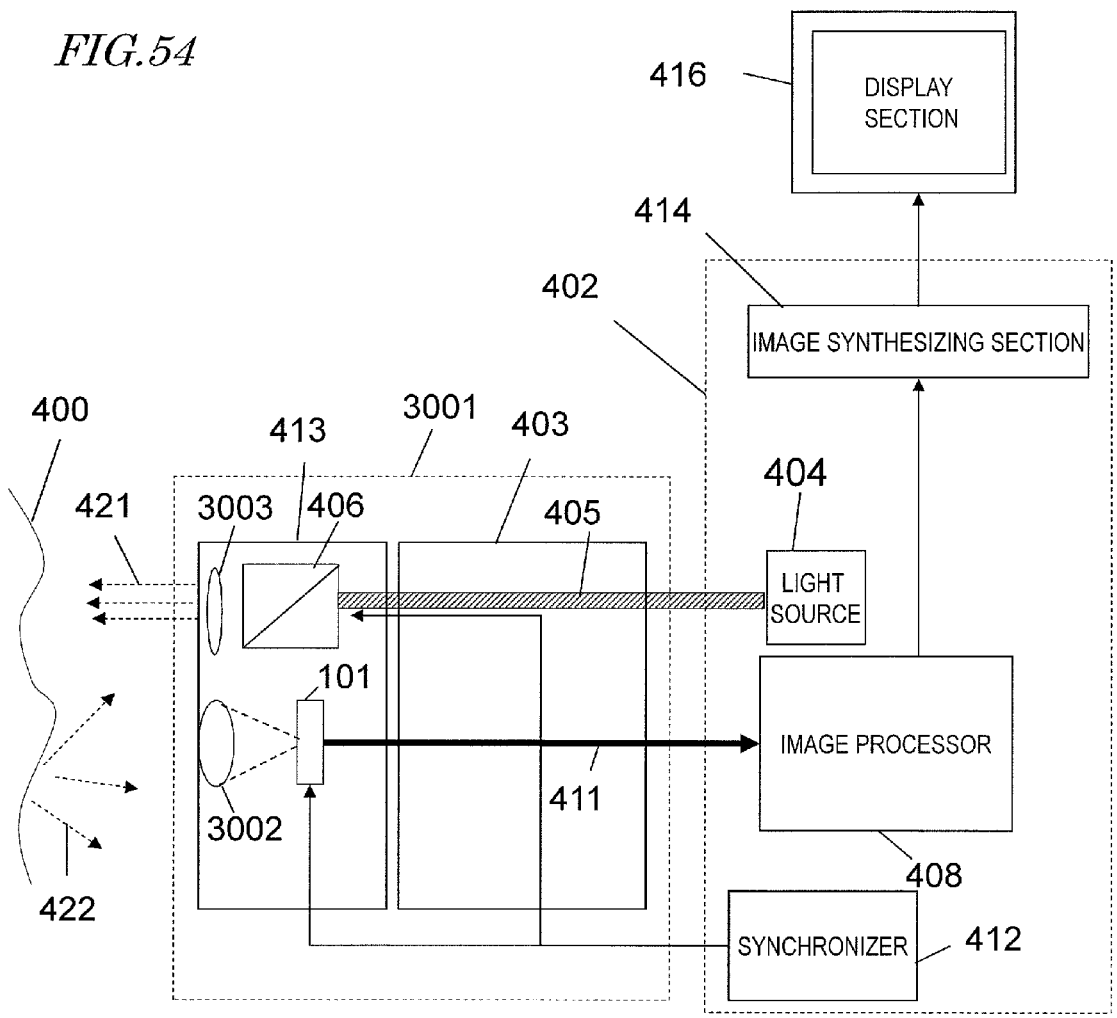
FIG. 54 illustrates schematically an overall configuration for an embodiment of a system including an endoscope according to the present disclosure.

FIG. 54 schematically illustrates an overall configuration for a system including an endoscope according to the present disclosure.

This system includes an endoscope 3001 and a controller 402. The endoscope 3001 includes a tip portion 413 with an image sensor 101 and an inserting portion 403 with a light guide 405 and a video signal line 411. As shown in FIG. 54, the inserting portion 403 of the endoscope 3001 has a structure that is elongated horizontally and that can be bent flexibly. Even when bent, the light guide 405 can also propagate light.

The controller 402 includes a light source 404 and an image processor 408. The white non-polarized light that has been emitted from the light source 404 is guided through the light guide 405 to a plane of polarization control element 406 of the tip portion 413 to be linearly polarized light 421 that irradiates the object. The plane of polarization control element 406 may be made up of a polarizer and a liquid crystal element and can transform the non-polarized light into linearly polarized light with an arbitrary plane of polarization using a voltage.

The plane of polarization control element 406 is a device that can rotate the plane of polarization using a liquid crystal material. The plane of polarization control element 406 may be implemented as a voltage application type liquid crystal device that includes a ferroelectric liquid crystal material, a polarization film and a quarter-wave plate in combination. The polarized illumination is cast toward the object through an illuminating lens 3003.

The synchronizer 412 gives the plane of polarization control element 406 a signal instructing to rotate the plane of polarization, thereby getting the plane of polarization of the light rotated. At the same time, the synchronizer 412 sends a shooting start signal to the image sensor 101, thereby getting video. The synchronizer 412 performs this series of processing steps a number of times. Optionally, the plane of polarization control element 406 may be a polarizer which produces linearly polarized illumination with a constant plane. In that case, the shooting session will be performed only once.

The light 422 returning from the object is transmitted through a shooting objective lens 3002 and then produces an image on the image sensor 101, which may be one of the embodiments of the polarization image sensor according to the present disclosure. The video signal representing the image captured is transmitted through the video signal line 411 to reach the image processor 408, which obtains the image information and polarization information described above based on the signal supplied from the polarization image sensor 101. And based on the output of the image processor 408, the image synthesizing section 414 gets an image, representing the surface topography of the object, presented on the display section 416.

As already described for respective embodiments, the flexible endoscope described above is applicable to both a frame sequential illumination and a synchronous illumination. Furthermore, the present disclosure is naturally applicable to not just flexible endoscopes but also surgical rigid endoscopes, industrial endoscopes, capsule endoscopes and any other kinds of endoscopes as well. Since some illumination is always used for an endoscope, lack of illumination would decrease the sensitivity of color light intensity information in any situation where such an endoscope is used. Thus, the present disclosure is applicable to each and every one of those other endoscopes.

As described above, the polarization optical elements for use in a polarization image sensor according to an embodiment of the present disclosure do not have high extinction ratio but the illuminating light can still be designed freely when the polarization image sensor is used in an endoscope, for example. Consequently, if linearly polarized light could be used as illuminating light, the component separating process can be carried out as well as with conventional polarizers.

The polarization image sensor of the present disclosure can obtain both color information and polarization information at the same time and as bight images with high sensitivity, which has never been realized by anybody in the related art. In addition, since the polarization image sensor of the present disclosure is versatile enough to be applied to both the frame sequential method and the synchronous method, which are the two major fields of endoscope technologies, the present disclosure can be used effectively to display capillary blood vessel and microscopic mucosa patterns on the mucosa surface layer with the difference in their color tone emphasized. Examples of endoscope-related applications that use some polarization images should also include sensing the microgeometry or surface micro-structure of the organ walls and enhancing the contrast of underwater scattered image in a capsule endoscope, besides such observation into the object's organ mucosa. That is to say, the industrial applicability of the present disclosure should further expand from now on.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A polarization image sensor comprising:
   a plurality of photodiodes which are arranged on an image capturing plane and each of which converts light into an electrical signal;
   a color mosaic filter in which color filters in multiple different colors are arranged so as to face the photodiodes;
   an optical low-pass filter which covers the color mosaic filter; and
   a plurality of polarization optical elements which are located closer to a light source than the optical low-pass filter,
   wherein each of the polarization optical elements covers an associated one of the photodiodes and makes light which is polarized in a predetermined direction in a plane that is parallel to the image capturing plane incident onto the optical low-pass filter,
   wherein the color mosaic filter has a structure in which a plurality of color filters in multiple different colors are arranged two-dimensionally, the color filters being arranged so that light that has passed through a plurality of polarization optical elements is transmitted through an associated one of the color filters in a single color, each said color filter covering a plurality of photodiodes, and
   wherein the optical low-pass filter is configured to shift at least a part of a light ray that has been transmitted through each of the polarization optical elements parallel to the image capturing plane by at least the arrangement pitch of the color filters in the color mosaic filter.

2. The polarization image sensor of claim 1, wherein one period of the two-dimensional arrangements of the polarization optical elements and the photodiodes has a spatial frequency which is an integral number of times as high as the cutoff frequency of the optical low-pass filter.

3. The polarization image sensor of claim 1, wherein the optical low-pass filter has a uniform optical property in a plane that is parallel to the image capturing plane.

4. The polarization image sensor of claim 1, wherein the optical low-pass filter includes:
   a first quarter wave plate;
   a first birefringent low-pass filter layer;
   a second quarter wave plate; and
   a second birefringent low-pass filter layer, which are stacked in this order so that the first quarter wave plate is closer to the light source than any other member of the optical low-pass filter.

5. The polarization image sensor of claim 4, wherein the optical low-pass filter further includes, between the second birefringent low-pass filter layer and the color mosaic filter,
 a third quarter wave plate, and
 a third birefringent low-pass filter layer, which are stacked in this order.

6. The polarization image sensor of claim 1, wherein the polarization optical elements form an array of polarizers in which a plurality of basic units, each being comprised of four polarization optical elements, are arranged in columns and rows, the four polarization optical elements included in each said basic unit having mutually different polarized light transmission axis directions, and
 wherein the basic units are arranged so that a color filter in a single color in the color mosaic filter is covered with a single basic unit.

7. The polarization image sensor of claim 6, wherein four of the basic units which are arranged in two columns and two rows cover four of the color filters which are arranged in two columns and two rows in the color mosaic filter.

8. The polarization image sensor of claim 7, wherein the four color filters that are arranged in two columns and two rows in the color mosaic filter form a Bayer arrangement.

9. A polarization image sensor comprising:
 a plurality of photodiodes which are arranged on an image capturing plane and each of which converts light into an electrical signal;
 a color mosaic filter in which color filters in multiple different colors are arranged so as to face the photodiodes;
 an optical low-pass filter which is located closer to a light source than the color mosaic filter; and
 a plurality of polarization optical elements which are located closer to the light source than the optical low-pass filter,
 wherein each of the polarization optical elements covers associated ones of the photodiodes and makes light which is polarized in a predetermined direction in a plane that is parallel to the image capturing plane incident onto the optical low-pass filter, and
 wherein the color mosaic filter has a structure in which a plurality of color filters in multiple different colors are arranged two-dimensionally, the color filters being arranged so that light that has passed through each said polarization optical element is transmitted through associated ones of the color filters in multiple different colors,
 wherein the optical low-pass filter includes:
 a first quarter wave plate;
 a first birefringent low-pass filter;
 a second quarter wave plate; and
 a second birefringent low-pass filter, which are stacked in this order so that the first quarter wave plate is closer to the light source than any other member of the optical low-pass filter, and
 wherein the first quarter wave plate has a pattern in which the directions of slow and fast axes are adjusted so as to change the polarization state of light that has been transmitted through each of the polarization optical elements into the polarization state of circularly polarized light.

10. The polarization image sensor of claim 9, wherein the color mosaic filter has a structure in which basic units with a Bayer arrangement are arranged two-dimensionally so that one photodiode is associated with one color filter, and
 wherein the polarization optical elements have
 a first striped array in which two kinds of polarization optical elements, of which the polarized light transmission axes are different from each other by 90 degrees, are alternately arranged in one direction, and
 a second striped array in which two kinds of polarization optical elements, of which the polarized light transmission axes are different from each other by 90 degrees, are alternately arranged in one direction, the polarized light transmission axes of the polarization optical elements in the second striped array intersecting at an angle of 45 degrees with the polarized light transmission axes of the polarization optical elements in the first striped array.

11. The polarization image sensor of claim 10, wherein the first quarter wave plate has
 a first set of striped portions which faces the first striped array of the polarization optical elements, and
 a second set of striped portions which faces the second striped array of the polarization optical elements, and
 wherein the slow and fast axes of the first and second sets of striped portions intersect with each other at an angle of 45 degrees.

* * * * *